United States Patent
Brown et al.

(10) Patent No.: US 7,375,100 B2
(45) Date of Patent: May 20, 2008

(54) 2-AMINO-PYRIDINE DERIVATIVES USEFUL FOR THE TREATMENT OF DISEASES

(75) Inventors: Alan Daniel Brown, Sandwich (GB); Charlotte Alice Louise Lane, Sandwich (GB); Russell Andrew Lewthwaite, Sandwich (GB)

(73) Assignee: Pfizer Inc, New York, NY (US)

( * ) Notice: Subject to any disclaimer, the term of this patent is extended or adjusted under 35 U.S.C. 154(b) by 318 days.

(21) Appl. No.: 10/860,772

(22) Filed: Jun. 3, 2004

(65) Prior Publication Data

US 2005/0014763 A1 Jan. 20, 2005

Related U.S. Application Data

(60) Provisional application No. 60/527,624, filed on Dec. 5, 2003.

(30) Foreign Application Priority Data

Jun. 4, 2003 (GB) .................. 0312832.9

(51) Int. Cl.
*A61K 31/55* (2006.01)
*A61K 31/44* (2006.01)
*A61K 31/496* (2006.01)
*C07D 213/73* (2006.01)
*C07D 223/16* (2006.01)

(52) U.S. Cl. .................. 514/213.01; 514/253.01; 514/352; 540/593; 544/360; 546/309; 546/146; 546/194; 546/265; 546/277.1; 546/280.1; 546/282.1

(58) Field of Classification Search .............. None
See application file for complete search history.

(56) References Cited

U.S. PATENT DOCUMENTS

| 4,358,455 A | 11/1982 | Atkinson et al. ........... 424/263 |
| 4,863,939 A | 9/1989 | Lindel et al. ............... 514/357 |
| 5,714,506 A | 2/1998 | Fisher et al. ............... 514/352 |
| 5,977,124 A | 11/1999 | Dow .......................... 514/272 |
| 7,067,541 B2 * | 6/2006 | Brown et al. ............... 514/352 |

FOREIGN PATENT DOCUMENTS

| EP | 0887079 | 12/1998 |
| EP | 0827746 | 4/2002 |
| EP | 0842924 | 8/2003 |
| EP | 1078924 | 10/2004 |
| WO | WO9529259 | 11/1995 |
| WO | WO9635671 | 11/1996 |
| WO | WO0142193 | 6/2001 |
| WO | WO03042164 | 5/2003 |

OTHER PUBLICATIONS

Barnes, P. J. Chest, 1997, 111:2, pp. 17S-26S.
Bryan, S.A. et al., Expert Opinion on Investigational Drugs, 2000, 9:1, p. 25-42.

* cited by examiner

*Primary Examiner*—Emily Bernhardt
(74) *Attorney, Agent, or Firm*—Gregg C. Benson; Robert T. Ronau

(57) ABSTRACT

The invention relates to compounds of formula (1)

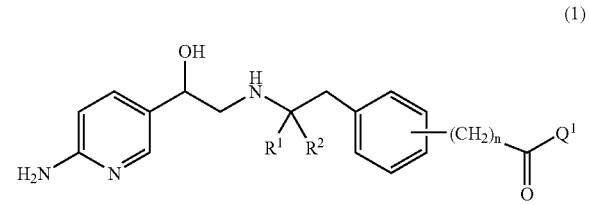

and to processes for the preparation of, intermediates used in the preparation of, compositions containing and the uses of, such derivatives. The compounds according to the present invention are useful in numerous diseases, disorders and conditions, in particular inflammatory, allergic and respiratory diseases, disorders and conditions.

39 Claims, No Drawings

2-AMINO-PYRIDINE DERIVATIVES USEFUL FOR THE TREATMENT OF DISEASES

This invention relates to β2 agonists of general formula (1):

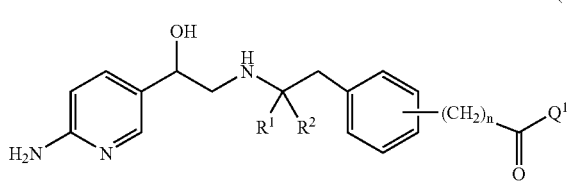

in which $R^1$, $R^2$, n and $Q^1$ have the meanings indicated below, and to processes for the preparation of, intermediates used in the preparation of, compositions containing and the uses of, such derivatives.

Adrenoceptors are members of the large G-protein coupled receptor super-family. The adrenoceptor subfamily is itself divided into the α and β subfamilies with the β sub-family being composed of at least 3 receptor sub-types: β1, β2 and β3. These receptors exhibit differential expression patterns in tissues of various systems and organs of mammals. β2 adrenergic (β2) receptors are mainly expressed in smooth muscle cells (e.g. vascular, bronchial, uterine or intestinal smooth muscles), whereas β3 adrenergic receptors are mainly expressed in fat tissues (therefore β3 agonists could potentially be useful in the treatment of obesity and diabetes) and β1 adrenergic receptors are mainly expressed in cardiac tissues (therefore β1 agonists are mainly used as cardiac stimulants).

The pathophysiology and treatments of airway diseases have been extensively reviewed in the literature (for reference see Barnes, P. J. Chest, 1997, 111:2, pp 17S-26S and Bryan, S. A. et al, Expert Opinion on investigational drugs, 2000, 9:1, pp25-42) and therefore only a brief summary will be included here to provide some background information.

Glucocorticosteroids, anti-leukotrienes, theophylline, cromones, anti-cholinergics and β2 agonists constitute drug classes that are currently used to treat allergic and non-allergic airways diseases such as asthma and chronic obstructive airways disease (COPD). Treatment guidelines for these diseases include both short and long acting inhaled β2 agonists. Short acting, rapid onset β2 agonists are used for "rescue" bronchodilation, whereas, long-acting forms provide sustained relief and are used as maintenance therapy.

Bronchodilation is mediated via agonism of the β2 adrenoceptor expressed on airway smooth muscle cells, which results in relaxation and hence bronchodilation. Thus, as functional antagonists, β2 agonists can prevent and reverse the effects of all bronchoconstrictor substances, including leukotriene D4 (LTD4), acetylcholine, bradykinin, prostaglandins, histamine and endothelins. Because β2 receptors are so widely distributed in the airway, β2 agonists may also affect other types of cells that play a role in asthma. For example, it has been reported that β2 agonists may stabilize mast cells. The inhibition of the release of bronchoconstrictor substances may be how β2 agonists block the bronchoconstriction induced by allergens, exercise and cold air. Furthermore, β2 agonists inhibit cholinergic neurotransmission in the human airway, which can result in reduced cholinergic-reflex bronchoconstriction.

In addition to the airways, it has also been established that β2 adrenoceptors are also expressed in other organs and tissues and thus β2 agonists, such as those described in the present invention, may have application in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

However, numerous β2 agonists are limited in their use due to their low selectivity or adverse side-effects driven by high systemic exposure and mainly mediated through action at β2 adrenoreceptors expressed outside the airways (muscle tremor, tachycardia, palpitations, restlessness). Therefore there is a need for improved agents in this class.

Accordingly, there is still a need for novel β2 agonists that would have an appropriate pharmacological profile, for example in terms of potency, selectivity and/or pharmacodynamic properties. In this context, the present invention relates to novel β2 agonists.

Various 2-amino-pyridine derivatives have already been synthesised. For example, the U.S. Pat. No. 4,358,455 discloses compounds having a random activity either as beta-adrenergic stimulants or as beta-adrenergic blockers, of formula:

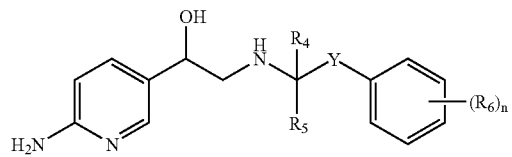

wherein $R_4$ and $R_5$ are independently selected from H and $(C_1-C_3)$alkyl; Y may namely be a methylene group, $R_6$ is selected from H, OH, alkoxy, methylenedioxy, halo or alkyl; and n is equal to 1 or 2.

Another example concerns the patent application WO 95/29259 that discloses selective β3 agonists (with little β1 and β2 activity) of formula:

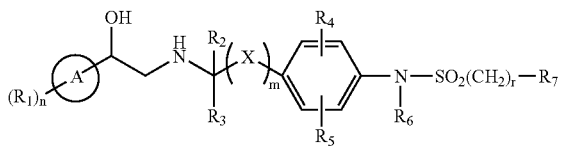

wherein A may be a 6-membered heterocyclic ring with from 1 to 4 heteroatoms selected from O, S and N; $R_1$ may be amino and n may be equal to 1; $R_2$, $R_3$ may be independently H or $(C_1-C_{10})$alkyl; m is 0 or 1, and X may be a methylene group; $R_4$, $R_5$ may be H; $R_6$ is H or $(C_1-C_{10})$alkyl; r is 0 to 3 and $R_7$ may be a phenyl 0 to 5 times substituted by numerous substituents (OH, oxo, Hal, CN etc . . . ).

Other 2-amino-pyridine derivatives are also disclosed in U.S. Pat. No. 5,714,506 as selective β3 agonists They are more specifically of formula:

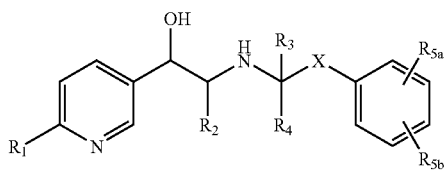

wherein $R_1$ may be amino; $R_2$ is H or $(C_1\text{-}C_6)$alkyl; $R_3$ and $R_4$ may be independently H or $(C_1\text{-}C_{12})$alkyl; X may be a $-(CH_2)_n-$ group with n selected from 1, 2 and 3; and $R_{5a}$ and $R_{5b}$ may be chosen from $-CONR_2R_2$, $-O-CH_2-CONR_2R_2$, aryl, $-CH_2$-alkoxy, $-CH_2-CONR_2R_2$ wherein $R_2$ is H or $(C_1\text{-}C_6)$ alkyl.

However, none of the 2-amino-pyridine derivatives synthesised so far have shown a selective β2 agonist activity, allowing them to be used as efficient drugs in the treatment of the β2-mediated diseases and/or conditions, in particular allergic and non-allergic airways diseases or other diseases such as those previously cited.

The invention relates to the compounds of general formula (1):

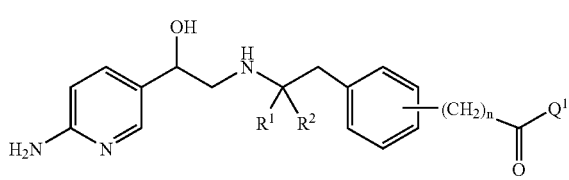

(1)

wherein the $(CH_2)_n-C(=O)Q^1$ group is in the meta or para position, $R^1$ and $R^2$ are independently selected from H and $C_1\text{-}C_4$ alkyl, n is 0, 1 or 2 and $Q^1$ is a group selected from:

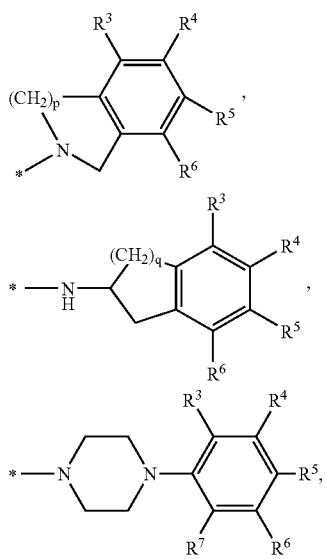

and a group *—NR-$Q^2$-A, wherein p is 1, 2 or 3, q is 1 or 2, $Q^2$ is a direct bond or a $C_1\text{-}C_4$ alkylene optionally substituted by OH, R is H, $C_1\text{-}C_4$ alkyl or phenyl optionally substituted by OH, and A is $C_3\text{-}C_7$ cycloalkyl, said cycloalkyl being optionally bridged by one or more carbon atoms, preferably 1 or 2 carbon atoms, tetrahydropyranyl, piperidinyl, tetrahydrothiopyranyl, pyridyl or a group selected from:

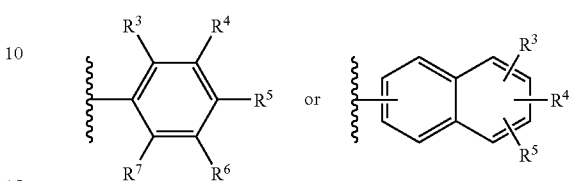

wherein $R^3$, $R^4$, $R^5$, $R^6$ and $R^7$ are the same or different and are each independently selected from H, $C_1\text{-}C_4$ alkyl, $OR^9$, $SR^9$, halo, $CF_3$, $OCF_3$, $(CH_2)_m COOR^9$, $SO_2NR^8R^9$, $CONR^8R^9$, $NR^8R^9$, $NHCOR^8$, $SO_2(C_1\text{-}C_4)$alkyl and phenyl optionally substituted by hydroxy or hydroxy$(C_1\text{-}C_4)$alkyl;

wherein m is an integer selected from 0, 1, and 2 and $R^8$ and $R^9$ are the same or different and are independently selected from H or $C_1\text{-}C_4$ alkyl and the * represent the attachment point to the carbonyl group;

or, if appropriate, their pharmaceutically acceptable salts and/or isomers, tautomers, solvates or isotopic variations thereof.

The compounds of the invention are selective agonists of the β2 receptors, that are particularly useful for the treatment of β2-mediated diseases and/or conditions, by showing excellent potency, in particular when administered via the inhalation route.

Preferably, the term "selective" means that the compounds of formula (1) show an agonist potency for the β2 receptor, which is at least about 50-fold higher as for the β3 receptor and at least about 500-fold higher as for the β1 receptor.

Preferably, the compounds of formula (1) show an agonist potency for the β2 receptor, which is less than 10 nM as measured by the cell-based assay described herein.

In the here above general formula (1), $C_1\text{-}C_4$ alkyl and $C_1\text{-}C_4$ alkylene denote a straight-chain or branched group containing 1, 2, 3 or 4 carbon atoms. This also applies if they carry substituents or occur as substituents of other radicals, for example in hydroxy$(C_1\text{-}C_4)$alkyl, O—$(C_1\text{-}C_4)$alkyl radicals, S—$(C_1\text{-}C_4)$alkyl radicals etc . . . . Examples of suitable $(C_1\text{-}C_4)$alkyl radicals are methyl, ethyl, n-propyl, iso-propyl, n-butyl, iso-butyl, sec-butyl, tert-butyl . . . hydroxy$(C_1\text{-}C_4)$ alkyl radicals are alkyl radicals substituted by a hydroxy (OH) substitutent. According to a preferred embodiment of said invention, such radicals contain one hydroxy substituent that can be located at any position on the alkyl radical. Examples of suitable hydroxy$(C_1\text{-}C_4)$alkyl radicals are hydroxymethyl, 1-hydroxyethyl, 2-hydroxyethyl etc . . . .

The term "$C_3\text{-}C_7$ cycloalkyl", includes cyclopropyl, cyclobutyl, cyclopentyl, cyclohexyl and cycloheptyl. A preferred cycloalkyl group is cyclohexyl.

The $C_3\text{-}C_7$ cycloalkyl wherein 2 carbon atoms or more are optionally bridged by one or more carbon atoms include adamantanyl, bicyclo[3.1.1]heptane, bicyclo[2.2.1]heptane, bicyclo[2.2.2]octane.

Finally, halo denotes a halogen atom selected from the group consisting of fluoro, chloro, bromo and iodo in particular fluoro or chloro.

In the following, the free bond on the phenyl group such as in the structure below:

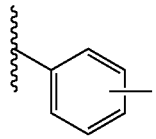

means that the phenyl can be substituted in the meta or para position.

The 2-amino-pyridine derivatives of the formula (1) can be prepared using conventional procedures such as by the following illustrative methods in which $R^1$, $R^2$, $Q^1$ and n are as previously defined for the 2-amino-pyridine derivatives of the formula (1) unless otherwise stated.

The 2-amino-pyridine derivatives of the formula (1) may be prepared by removal of the protecting group(s) "Prot" from the compound of formula (2):

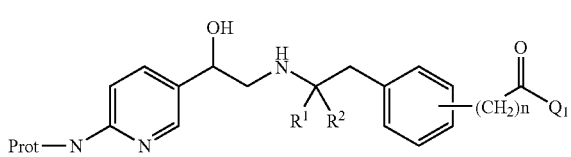

(2)

wherein $R^1$, $R^2$, $Q^1$ and n are as previously described for the 2-amino-pyridine derivatives of formula (1) and Prot is a suitable protecting group (or 2 suitable protecting groups) for the amino-pyridine, which include but is not limited to tert-butoxycarbonyl, acyl or 2,5-dimethyl pyrrole, by methods well known to those skilled in the art such as standard methodology for cleaving nitrogen protecting groups as found in textbooks (e.g. T. W. GREENE, *Protective Groups in Organic Synthesis*, A. Wiley-Interscience Publication, 1981).

The compound of formula (2) may be prepared by coupling an acid of formula (3):

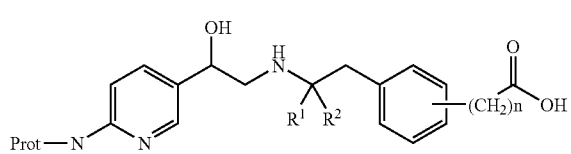

(3)

wherein Prot, $R^1$, $R^2$ and n are as previously defined, with an amine of formula NRH-$Q^2$-A (4.1),

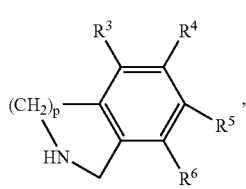

(4.2)

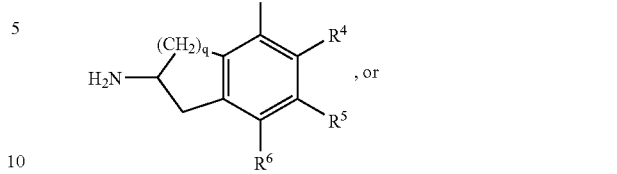

(4.3)

, or (4.4)

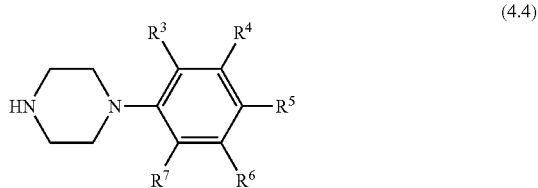

wherein p, q, $R^3$, $R^4$, $R^5$, $R^6$ and $R^7$ are as previously defined.

The coupling of the acid (3) to the amine (4.1), (4.2), (4.3) or (4.4) s generally carried out in an excess of said amine, with a conventional coupling agent (e.g. 1-(3-dimethylaminopropyl)-3-ethylcarbodiimide hydrochloride or N,N'-dicyclohexylcarbodiimide), optionally in the presence of a catalyst (e.g. 1-hydroxybenzotriazole hydrate or 1-hydroxy-7-azabenzotriazole), and optionally in the presence of a tertiary amine base (e.g. N-methylmorpholine, triethylamine or N,N-diisopropylethylamine). The reaction may be undertaken in a suitable solvent such as pyridine, N,N-dimethylformamide, tetrahydrofuran, dimethylsulfoxide, dichloromethane or ethyl acetate, and at temperature comprised between 10° C. and 40° C. (room temperature).

Said (4.1), (4.2), (4.3) or (4.4), is either commercially available or may be prepared by conventional methods well-known to the one skilled in the art (e.g. acylation, sulfonylation, reduction, oxidation, alkylation, protection, deprotection etc . . . ) from commercially available material.

The acid of formula (3) may be prepared from the corresponding ester of formula (5):

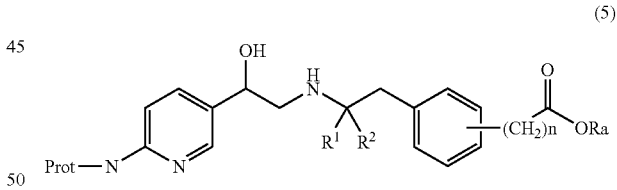

(5)

wherein Prot, $R^1$, $R^2$, Ra and n are as previously defined according to any method well-known to the one skilled in the art to prepare an acid from an ester.

In a typical procedure, the hydrolysis of the ester to give an acid is undertaken according to any method well known to the man skilled in the art to prepare an acid from an ester, without modifying the rest of the molecule. For example, the ester may be hydrolysed by treatment with aqueous acid or base (e.g. hydrogen chloride, potassium hydroxide, sodium hydroxide or lithium hydroxide), optionally in the presence of a co-solvent (e.g. tetrahydrofuran/1,4-dioxan), at a temperature comprised between 20° C. and 100° C., for a period of 1 to 40 hours.

The ester of formula (5) may be prepared according to different routes depending on the choice of $R^1$ and $R^2$.

If R¹ is hydrogen, R² is (C₁-C₄)alkyl and n is different from 0, then the ester of formula (5) may be prepared by reaction of an amine of formula (6):

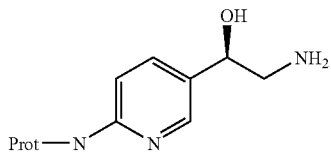

with an excess of a ketone of formula (7):

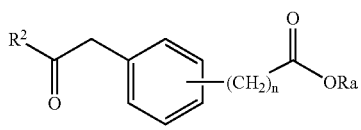

wherein Prot, R², Ra and n are as previously defined, to form an intermediate compound, which is reduced by a suitable reducing agent (e.g. sodium cyanoborohydride of formula NaCN(BH)₃ or sodium triacetoxyborohydride of formula Na(OAc)₃BH), optionally in the presence of acetic acid. The reaction is generally performed in a suitable solvent such as tetrahydrofuran or dichloromethane, at a temperature comprised between 20° C. and 80° C. for 3 to 72 hours, giving the compound of formula (5) as a mixture of diastereomers. According to another alternative, the reduction may be carried out in the presence of a drying agent such as molecular sieves or magnesium sulfate.

The amine of formula (6) may be prepared starting from a 2-amino-5-bromo-pyridine as described in EP 1 078 924 or WO 99/32475.

Alternatively, the ester of formula (5) may be prepared according to scheme 1 as follows:

wherein n, Ra and Prot are as previously defined, and Rb and Rc represent any suitable substituents so that HNRbRc is a chiral amine (for example, Rb may be hydrogen and Rc may be a α-methylbenzyl group) and the bonds between N and Rb and N and Rc can be easily cleaved to give the free amine of formula (9).

In a typical procedure, the ketone of formula (7) is reacted with a suitable chiral non-racemic amine HNRbRc (e.g. α-methylbenzylamine or any other commercially available chiral non-racemic amine) to form a chiral intermediate, which is reduced by a suitable reducing agent (e.g. sodium cyanoborohydride of formula NaCN(BH)₃ or sodium triacetoxyborohydride of formula Na(OAc)₃BH) optionally in the presence of sodium acetate or acetic acid, and also optionally in the presence of a drying agent (e.g. molecular sieves, magnesium sulfate) as previously described. The resulting product is then converted to the hydrochloride salt and selectively crystallised from a suitable solvent or mixture of solvents (e.g. isopropanol, ethanol, methanol, diisopropyl ether or diisopropyl ether/methanol) to give the diastereomerically pure product of formula (8), or its enantiomer, if the opposite enantiomer of the amine HNRbRc is used.

The protected amine of formula (8) is then cleaved to give the corresponding free amine of formula (9) using standard methodology for cleaving nitrogen protecting groups, such as that found in the text book (see for example T. W. Greene, *Protective Groups in Organic Synthesis*, A. Wiley-Interscience Publication, 1981). When a α-methylbenzylamine is used, then the cleavage may be performed using ammonium formate and palladium hydroxide on carbon of formula Pd(OH)₂/C as catalyst.

Said amine of formula (9) is then reacted with an epoxide of formula (10) in a suitable solvent or mixture of solvents (e.g. dimethyl sulfoxide/toluene), at a temperature com- Scheme 1

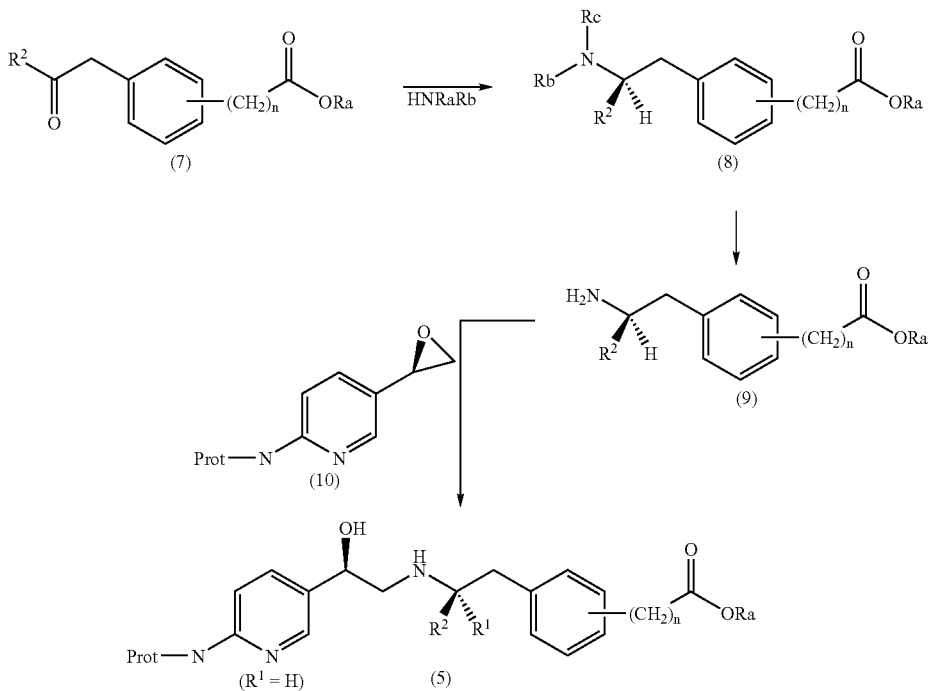

prised between 20° C. and 80° C. and optionally in the presence of a catalyst for 8 to 40 hours, to give the ester of formula (5).

The epoxide of formula (10) may be prepared starting from starting from a 2-amino-5-bromo-pyridine as described in EP 1 078 924 or WO 99/32475.

The ketone of formula (7) described above may be prepared by enolate arylation of an aryl halide of formula (11):

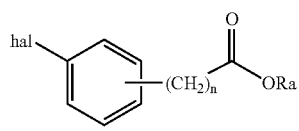
(11)

wherein Ra and n are as previously defined and halo represents an halogen atom, which includes, but is not limited to, fluoro, chloro and bromo.

In a typical procedure, the aryl halide of formula (11) is reacted with a tin enolate generated in situ by treatment of a vinyl acetate (e.g. isoprenyl acetate with tri-n-butyltin methoxide of formula $Bu_3SnOMe$) in the presence of a suitable palladium catalyst (palladium acetate/tri-ortho-tolylphosphine of formula $Pd(OAc)_2/P(o-Tol)_3$) in a non-polar solvent (e.g. toluene, benzene, hexane). Preferably, the reaction is carried out at a temperature comprised between 80° C. and 110° C. for 6 to 16 hours.

The aryl halide of formula (11) may be prepared by esterification of the corresponding acid of formula (12):

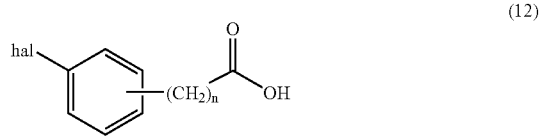
(12)

wherein halo is as previously defined, according to any method well-known to the one skilled in the art to prepare an ester from an acid, without modifying the rest of the molecule.

In a typical procedure, the acid of formula (12) is reacted with an alcoholic solvent of formula RaOH, wherein Ra is as previously defined, in the presence of an acid such as hydrogen chloride at a temperature between 10° C. and 40° C. (room temperature) for 8 to 16 hours.

According to another alternative, the acid of formula (12) is reacted with a bromoalkyl of formula RaBr in the presence of a suitable base such as cesium carbonate, in a suitable organic solvent (e.g. N,N-dimethylformamide, tetrahydrofuran) at a temperature and for a time as here above mentioned.

The acid of formula (12) is either a commercial product or it may be prepared by conventional procedures well-known to the man skilled in the art.

If $R_1$ and $R^2$ are both different from hydrogen and n is different from 0, then the ester of formula (5) may be prepared according to scheme 2 as follows:

Scheme 2

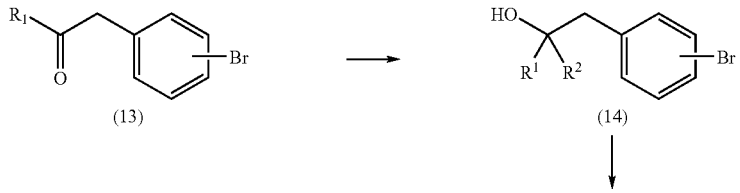

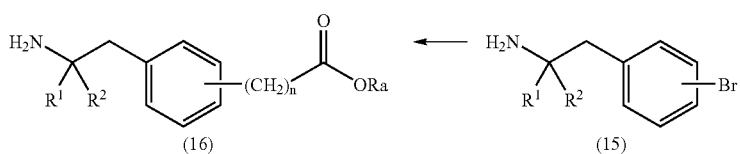

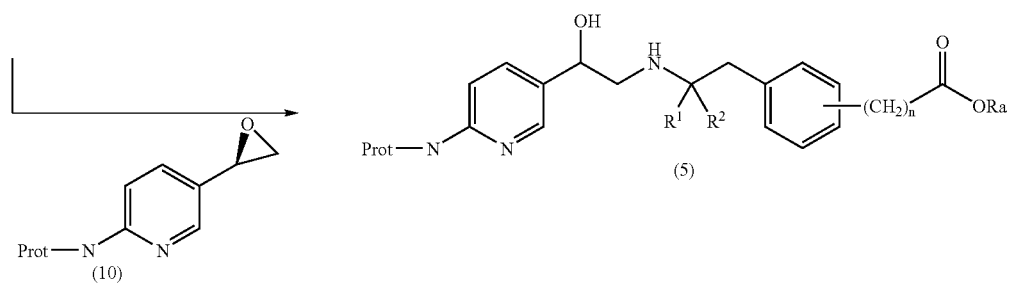

wherein $R^1$, $R^2$, Ra and Prot' are as previously defined.

In a typical procedure, the halo ketone of formula (13) is reacted with an "activated" alkyl (organometallic alkyl such as $R^2MgBr$, $R^2MgCl$ or $R^2Li$) to give the corresponding tertiary alcohol of formula (14). This organometallic addition is generally undertaken in a suitable solvent such as tetrahydrofuran, ether, cyclohexane or 1,4-dioxane, at a temperature comprised between 10° C. and 40° C. (room temperature) for 1 to 24 hours Said tertiary alcohol of formula (14) is then treated with an alkyl nitrile (e.g. acetonitrile, chloroacetonitrile) in the presence of an acid (e.g. sulphuric acid, acetic acid) to give a protected intermediate which in turn cleaved using standard methodology for cleaving nitrogen protecting group such as those mentioned in textbooks, to give the amine of formula (15).

The amine of formula (15) is then converted to the boronic acid ester by treatment with a suitable boron source (e.g. pinacolborane, bis(pinacolato)diboron) in the presence of a suitable palladium catalyst (e.g. palladium(II)acetate/tri-ortho-tolylphosphine of formula $Pd(OAc)_2/P(o-tol)_3$ or (diphenylphosphino) ferrocenyl palladium(II)chloride of formula $dppfPdCl_2$). The reaction is generally undertaken in a suitable solvent such as dimethyl sulfoxide or toluene, optionally in the presence of a base (e.g. potassium acetate), at a temperature comprised between 60° C. and 110° C. for a period of 4 to 24 hours. The intermediate boronic acid ester is then coupled with ethylbromoacetate in the presence of a suitable palladium catalyst (e.g. tetrakis(triphenylphosphine) palladium(0) of formula $Pd(PPh_3)_4$, palladium(II) acetate/tri-ortho-tolylphosphine of formula $Pd(OAc)_2/P(o-tol)_3$ or (diphenylphosphino)ferrocenyl palladium(II) chloride of formula $dppfPdCl_2$) to give the compound of formula (16).

The compound of formula (5) is finally obtained by reaction of the compound of formula (16) with the epoxide of formula (10) as previously described.

The compound of formula (13) is either commercial or it may be easily prepared from commercial compounds by conventional procedures well known to the one skilled in the art.

Alternatively the amine of formula (16) may be prepared according to scheme 3 as follows:

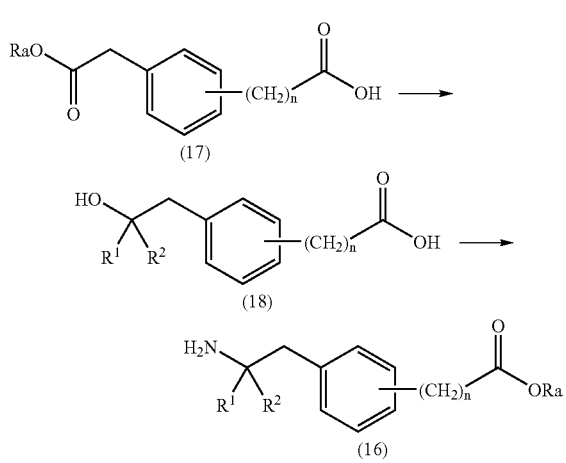

wherein $R^1$, $R^2$ and Ra are as previously defined.

In a typical procedure, the ester of formula (17) is reacted with an "activated" alkyl (organometallic alkyl such as $R^2MgBr$, $R^2MgCl$ or $R^2Li$) to give the corresponding tertiary alcohol of formula (18) using the method described above.

Said tertiary alcohol of formula (17) is then treated with an alkyl nitrile (e.g. acetonitrile, chloroacetonitrile) in the presence of an acid (e.g. sulphuric acid, acetic acid) to give a protected intermediate which is in turn cleaved using standard methodology for cleaving nitrogen protecting group such as those mentioned in textbooks. The resulting aminoacid is then esterified using the method described herein to give the amine of formula (16).

The compound of formula (17) is either commercial or it may be easily prepared from commercial compounds by conventional procedures well known to the one skilled in the art.

If n is equal to 0, then the amine of formula (16) may be prepared according to the following scheme:

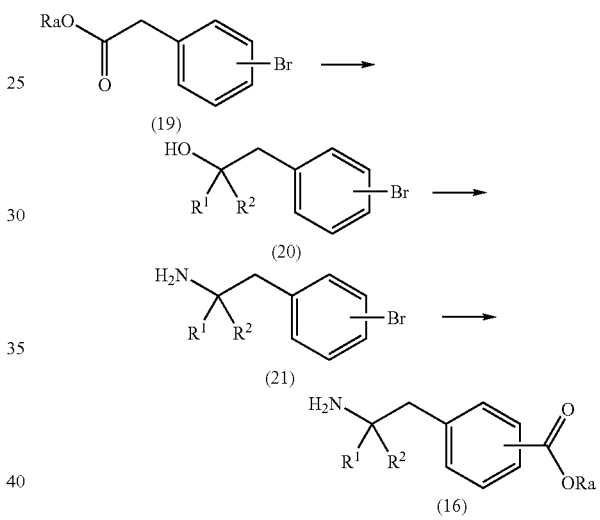

wherein $R^1$, $R^2$ and Ra are as previously defined.

In a typical procedure, the ester of formula (19) is reacted with an "activated" alkyl (organometallic alkyl such as $R^2MgBr$, $R^2MgCl$ or $R^2Li$) to give the corresponding tertiary alcohol of formula (20) using the method described above.

Said tertiary alcohol of formula (20) is then treated with an alkyl nitrile (e.g. acetonitrile, chloroacetonitrile) in the presence of an acid (e.g. sulphuric acid, acetic acid) to give a protected intermediate which is in turn cleaved using standard methodology for cleaving nitrogen protecting group such as those mentioned in textbooks to give the bromo amine (21).

The resulting bromo amine (21) is treated with a suitable palladium catalyst (e.g. [1,1'-bis(diphenylphosphino)ferrocene]dichloropalladium(II)) under an atmosphere of carbon monoxide using RaOH as solvent (e.g. MeOH, EtOH) at elevated temperature (100° C.) and pressure (100 psi) to give the ester of formula (16).

The compound of formula (19) is either commercial or it may be easily prepared from commercial compounds by conventional procedures well known to the one skilled in the art.

Alternatively, where both $R^1$ and $R^2$ are H, the amine of formula (16) may be prepared according to scheme 5 as follows:

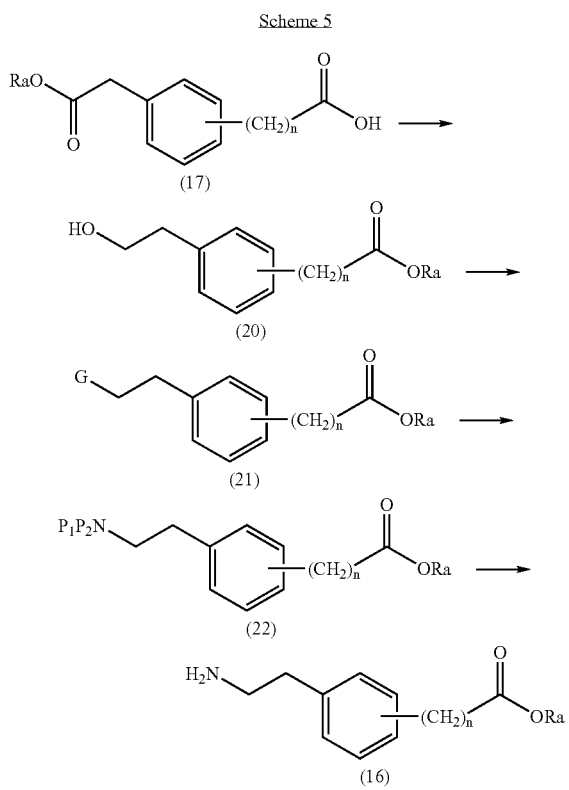

wherein Ra is as previously defined.

In a typical procedure, the ester of formula (17) is reduced with an a reducing agent (such as $LiAlH_3$) to give the corresponding primary alcohol of formula (20) using the method described above.

Said tertiary alcohol of formula (20) is then treated to yield an activating group (G) (halogen, mesylate, tosylate) using standard methodology for alcohol activation such as those mentioned in textbooks. The resulting activating group is then displaced by a nitrogen containing group (such as azide, phthalamide) using standard methodology for nucleophilic displacements such as those mentioned in textbooks. The amine is then liberated by hydrolysis (hydroxide, hydrazine) or reduction (hydrogenation, reducing agents such as LiAlH4) of the nitrogen containing group to give the amine of formula (16).

All of the above reactions and the preparations of novel starting materials used in the preceding methods are conventional and appropriate reagents and reaction conditions for their performance or preparation as well as procedures for isolating the desired products will be well-known to those skilled in the art with reference to literature precedents and the examples and preparations hereto.

For some of the steps of the here above described process of preparation of the 2-amino-pyridine derivatives of formula (1), it can be necessary to protect the potential reactive functions that are not wished to react, and to cleave said protecting groups in consequence. In such a case, any compatible protecting radical can be used. In particular methods of protection and deprotection such as those described by T. W. GREENE (*Protective Groups in Organic Synthesis*, A. Wiley-Interscience Publication, 1981) or by McOMIE (*Protective Groups in Organic Chemistry*, Plenum Press, 1973), can be used.

Also, the 2-amino-pyridine derivatives of formula (1) as well as intermediate for the preparation thereof can be purified according to various well-known methods, such as for example crystallization or chromatography.

Compounds of formula (1) wherein n is 1 or 2, $Q^1$ is a group *—$NH-Q^2-A$, wherein $Q^2$ is a $C_1-C_4$ alkylene and A is a group

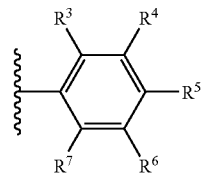

wherein $R^3$, $R^4$, $R^5$, $R^6$ and $R^7$ are as defined above, are particularly preferred. The following substituents are generally preferred:

$R^1$ is H and $R^2$ is $C_1-C_4$ alkyl, more preferably $CH_3$ or $R^1$ and $R^2$ are the same or different and are selected from $C_1-C_4$ alkyl, more preferably $R^1$ and $R^2$ are both $CH_3$ and/or, n is 1 and/or, $Q^2$ is selected from —$CH_2$—, —$(CH_2)_2$—, —$(CH_2)_3$— and —$CH(CH_3)$—, more preferably $Q^2$ is —$CH_2$—, and/or A is a group of formula:

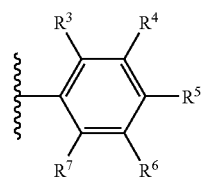

wherein $R^3$, $R^4$, $R^5$, $R^6$ and $R^7$ are the same or different and are selected from H, $C_1-C_4$ alkyl, $OR^9$, Cl, F, $CF_3$, $OCF_3$, $COOR^9$, $C(=O)NR^8R^9$, $SO_2NR^8R^9$, provided at least 2 of $R^3$ to $R^7$ are equal to H, wherein $R^8$ and $R^9$ are the same or different and are selected from H or $C_1-C_4$ alkyl.

Preferably, A is a group of formula:

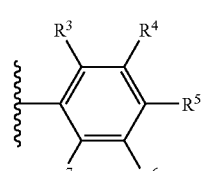

wherein $R^3$, $R^4$, $R^5$, $R^6$ and $R^7$ are the same or different and are selected from H, $CH_3$, OH, $OCH_3$, $OCH_2CH_3$, Cl, F, $CF_3$, $OCF_3$, COOH, $SO_2NH_2$, provided at least 2 of $R^3$ to $R^7$ are equal to H.

Preferably, A is a group of formula:

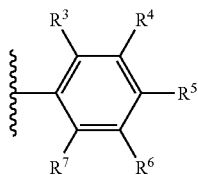

wherein $R^3$, $R^4$, $R^5$, $R^6$ and $R^7$ are the same or different and are selected from H, $CH_3$, OH, $OCH_3$, $OCH_2CH_3$, Cl, F, $CF_3$, $OCF_3$, COOH, $SO_2NH_2$, provided at least 3 of $R^3$ to $R^7$ are equal to H.

Preferably A is a group of formula:

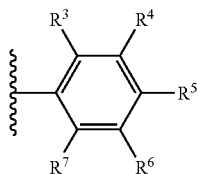

wherein $R^3$, $R^4$, $R^5$, $R^6$ and $R^7$ are selected from H, $CH_3$, OH, Cl, $OCH_2CH_3$, provided at least 3 of $R^3$ to $R^7$ are equal to H.

Preferably A is a group of formula:

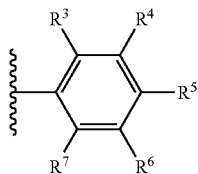

wherein at least one of $R^3$, $R^4$, $R^5$, $R^6$ and $R^7$ is other than hydrogen.

Other preferred compounds are those wherein n is 1 or 2 and $Q^1$ is

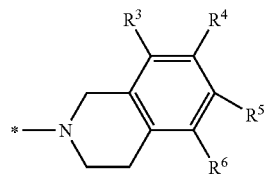

wherein $R^3$, $R^4$, $R^5$ and $R^6$ are the same or different and are selected from H, $C_1$-$C_4$ alkyl, $OR^9$, $SR^9$, halo, $CF_3$, $OCF_3$, $COOR^9$, $SO_2NR^8R^9$, $CONR^8R^9$, $NR^8R^9$, $NHCOR^9$, provided at least 2 of $R^3$ to $R^6$ are equal to H, wherein $R^8$ and $R^9$ are the same or different and are selected from H or $C_1$-$C_4$ alkyl.

Preferably, $Q^1$ is

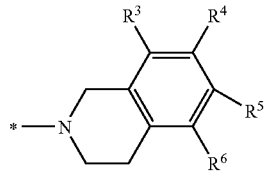

wherein $R^3$, $R^4$, $R^5$ and $R^6$ are the same or different and are selected from H and $OR^9$, provided at least 2 of $R^3$ to $R^6$ are equal to H;

wherein $R^9$ is selected from H or $C_1$-$C_4$ alkyl.

Other preferred compounds are those wherein n is 1 or 2 and $Q^1$ is

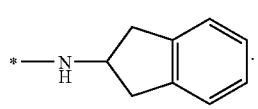

Other preferred compounds are those wherein n is 1 or 2 and $Q^1$ is a group *—NH-$Q^2$-A, wherein $Q^2$ is a $C_1$-$C_4$ alkylene and A is a pyridin-2-yl.

Other preferrer compounds are those wherein n is 1 or 2 and $Q^1$ is a group *—NH-$Q^2$-A, wherein $Q^2$ is a $C_1$-$C_4$ alkylene and A is naphthyl.

Other preferrer compounds are those wherein n is 1 or 2 and $Q^1$ is a group *—NH-$Q^2$-A, wherein $Q^2$ is a $C_1$-$C_4$ alkylene and A is $C_3$-$C_7$ cycloalkyl, said cycloalkyl being optionally bridged by one or more carbon atoms. Preferably A is cyclohexyl, cycloheptyl or adamantanyl.

Other preferrer compounds are those wherein n is 1 or 2 and $Q^1$ is a group *—NH-$Q^2$-A, wherein $Q^2$ is a $C_1$-$C_4$ alkylene and A is naphthyl substituted with OH.

Other preferred compounds are those of formula (1) wherein n is 0 or 1 and $Q^1$ is a group of formula:

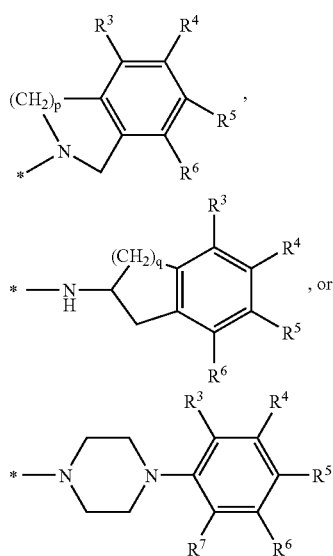

wherein p is 2 or 3, q is 2, $R^3$, $R^4$, $R^5$ $R^6$ and $R^7$ are the same or different and are selected from H and OH, provided that at least one of $R^3$, $R^4$, $R^5$ $R^6$ and $R^7$ is OH.

Other preferred compounds are those of formula (1) wherein n is 0 or 1, $R^1$ is H or $C_1$-$C_4$ alkyl, $R^2$ is $C_1$-$C_4$ alkyl, and $Q^1$ is a group *—NR-$Q^2$-A wherein A is of formula:

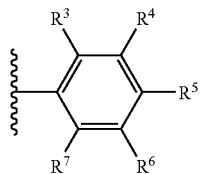

wherein R, $R^3$, $R^4$, $R^5$, $R^6$ and $R^7$ are as previously defined. The following substitutents are generally preferred:

$R^1$ is H and $R^2$ is $C_1$-$C_4$ alkyl, more preferably $CH_3$ or $R^1$ and $R^2$ are the same or different and are selected from $C_1$-$C_4$ alkyl, more preferably $R^1$ and $R^2$ are both $CH_3$ and/or, R is selected from H, $CH_3$, $CH_2CH_3$ and phenyl substituted by OH, and/or $Q^2$ is a direct bond or is selected from —$CH_2$—, —$(CH_2)_2$—, —$(CH_2)_4$— —$CH_2$—$C(CH_3)_2$—, and —$CH_2$—CH(OH)—, and/or A is a group of formula:

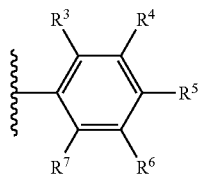

wherein $R^3$, $R^4$, $R^5$, $R^6$ and $R^7$ are the same or different and are selected from H, $C_1$-$C_4$ alkyl, $OR^9$, Cl, F, $CF_3$, $COOR^9$, $SO_2(C_1$-$C_4)$alkyl, and phenyl substituted by OH or hydroxy (C1-C4)alkyl, provided at least 2 of $R^3$ to $R^7$ are equal to H, wherein $R^8$ and $R^9$ are the same or different and are selected from H or $C_1$-$C_4$ alkyl.

Preferably, A is of formula

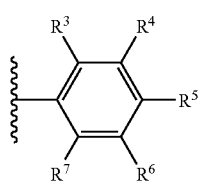

wherein $R^3$, $R^4$, $R^5$, $R^6$ and $R^7$ are the same or different and are selected from H, $CH_3$, $C(CH_3)_3$, OH, $OCH_3$, $OCH_2CH_3$, Cl, F, $CF_3$, $COOCH_3$, $SO_2$—$CH_2CH_3$, and phenyl substituted by OH or by —$CH_2$—OH, provided at least 2 of $R^3$ to $R^7$ are equal to H.

Particularly preferred are the compounds of the formula (1) as described in the Examples section hereafter, i.e.:

2-(3-{(2R)-2-[(2R)-2-(6-Amino-pyridin-3-yl)-2-hydroxy-ethylamino]-propyl}-phenyl)-N-benzyl-acetamide, 2-(3-{(2R)-2-[(2R)-2-(6-Amino-pyridin-3-yl)-2-hydroxy-ethylamino]-propyl}-phenyl)-N-(2-methoxy-benzyl)-acetamide, 2-(3-{(2R)-2-[(2R)-2-(6-Amino-pyridin-3-yl)-2-hydroxy-ethylamino]-propyl}-phenyl)-N-(2-ethoxy-benzyl)-acetamide, 2-(3-{(2R)-2-[(2R)-2-(6-Amino-pyridin-3-yl)-2-hydroxy-ethylamino]-propyl}-phenyl)-N-(3-phenyl-propyl)-acetamide, 2-(3-{(2R)-2-[(2R)-2-(6-Amino-pyridin-3-yl)-2-hydroxy-ethylamino]-propyl}-phenyl)-N-phenethyl-acetamide, 2-(3-{(2R)-2-[(2R)-2-(6-Amino-pyridin-3-yl)-2-hydroxy-ethylamino]-propyl}-phenyl)-N-(3,4-dimethyl-benzyl)-acetamide, 2-(3-{(2R)-2-[(2R)-2-(6-Amino-pyridin-3-yl)-2-hydroxy-ethylamino]-propyl}-phenyl)-N-indan-2-yl-acetamide, 2-(3-{(2R)-2-[(2R)-2-(6-Amino-pyridin-3-yl)-2-hydroxy-ethylamino]-propyl}-phenyl)-N-(3,4-dichloro-benzyl)-acetamide, 2-(3-{2-[(2R)-2-(6-Amino-pyridin-3-yl)-2-hydroxy-ethylamino]-propyl}-phenyl)-N-(4-hydroxy-3-methoxy-benzyl)-acetamide, 2-(4-{2-[(2R)-2-(6-Amino-pyridin-3-yl)-2-hydroxy-ethylamino]-2-methyl-propyl}-phenyl)-N-(3-methoxy-benzyl)-acetamide, 2-(4-{2-[(2R)-2-(6-Amino-pyridin-3-yl)-2-hydroxy-ethylamino]-2-methyl-propyl}-phenyl)-N-(2,6-dimethoxy-benzyl)-acetamide, 2-(3-{2-[(2R)-2-(6-Amino-pyridin-3-yl)-2-hydroxy-ethylamino]-2-methyl-propyl}-phenyl)-N-(4-sulfamoyl-benzyl)-acetamide, 2-(3-{2-[(2R)-2-(6-Amino-pyridin-3-yl)-2-hydroxy-ethylamino]-2-methyl-propyl}-phenyl)-N-(2-ethoxy-benzyl)-acetamide, 2-(3-{2-[(2R)-2-(6-Amino-pyridin-3-yl)-2-hydroxy-ethylamino]-2-methyl-propyl}-phenyl)-N-indan-2-yl-acetamide, 2-(3-{2-[(2R)-2-(6-Amino-pyridin-3-yl)-2-hydroxy-ethylamino]-2-methyl-propyl}-phenyl)-N-benzyl-acetamide, 2-(3-{2-[(2R)-2-(6-Amino-pyridin-3-yl)-2-hydroxy-ethylamino]-2-methyl-propyl}-phenyl)-N-phenethyl-acetamide, 2-(3-{2-[(2R)-2-(6-Amino-pyridin-3-yl)-2-hydroxy-ethylamino]-2-methyl-propyl}-phenyl)-N-(3-phenyl-propyl)-acetamide, 2-(3-{2-[(2R)-2-(6-Amino-pyridin-3-yl)-2-hydroxy-ethylamino]-2-methyl-propyl}-phenyl)-N-(3,5-dichloro-benzyl)-acetamide, 2-(3-{2-[(2R)-2-(6-Amino-pyridin-3-yl)-2-hydroxy-ethylamino]-2-methyl-propyl}-phenyl)-N-(3,4-dimethyl-benzyl)-acetamide, 2-(3-{2-[(2R)-2-(6-Amino-pyridin-3-yl)-2-hydroxy-ethylamino]-2-methyl-propyl}-phenyl)-N-(3,4-dichloro-benzyl)-acetamide, 2-(3-{2-[(2R)-2-(6-Amino-pyridin-3-yl)-2-hydroxy-ethylamino]-propyl}-phenyl)-N-(2-fluoro-5-trifluoromethyl-benzyl)-acetamide, 2-(3-{2-[(2R)-2-(6-Amino-pyridin-3-yl)-2-hydroxy-ethylamino]-propyl}-phenyl)-N-(3-trifluoromethoxy-benzyl)-acetamide, 2-(3-{2-[(2R)-2-(6-Amino-pyridin-3-yl)-2-hydroxy-ethylamino]-propyl}-phenyl)-N-(3-fluoro-4-trifluoromethyl-benzyl)-acetamide, 2-(3-{2-[(2R)-2-(6-Amino-pyridin-3-yl)-2-hydroxy-ethylamino]-propyl}-phenyl)-N-(3,4,5-trimethoxy-benzyl)-acetamide, -(3-{2-[(2R)-2-(6-Amino-pyridin-3-yl)-2-hydroxy-ethylamino]-propyl}-phenyl)-N-(4-trifluoromethoxy-benzyl)-acetamide,
2-(3-{2-[(2R)-2-(6-Amino-pyridin-3-yl)-2-hydroxy-ethylamino]-propyl}-phenyl)-N-(4-fluoro-2-trifluoromethyl-benzyl)-acetamide,
2-(3-{2-[(2R)-2-(6-Amino-pyridin-3-yl)-2-hydroxy-ethylamino]-propyl}-phenyl)-N-(5-fluoro-2-trifluoromethyl-benzyl)-acetamide,
2-(3-{(2R)-2-[2-(6-Aminopyridin-3-yl)-2-hydroxyethylamino]-2-methylpropyl}phenyl)-N-(4'-hydroxybiphenyl-3-ylmethyl)acetamide,
2-(3-{(2R)-2-[2-(6-Aminopyridin-3-yl)-2-hydroxyethylamino]-2-methylpropyl}phenyl)-N-(4'-hydroxybiphenyl-4-ylmethyl)acetamide,
2-(3-{(2R)-2-[(2R)-2-(6-Aminopyridin-3-yl)-2-hydroxyethylamino]propyl}phenyl)-N-(4'-hydroxy-biphenyl-3-ylmethyl)acetamide,
2-(3-{(2R)-2-[(2R)-2-(6-Aminopyridin-3-yl)-2-hydroxyethylamino]propyl}phenyl)-N-(4-hydroxynaphthalen-1-ylmethyl)acetamide,
3-{2-[(2R)-2-(6-Aminopyridin-3-yl)-2-hydroxyethylamino]-2-methylpropyl}-N-(4'-hydroxybiphenyl-3-ylmethyl)benzamide,
3-{(2R)-2-[2-(6-Amino-pyridin-3-yl)-2-hydroxy-ethylamino]-2-methyl-propyl}-N-[2-(4-hydroxy-phenyl)-2-methyl-propyl]-benzamide,
3-{2-[(2R)-2-(6-Amino-pyridin-3-yl)-2-hydroxyethylamino]-2-methylpropyl}-N-[2-(4-hydroxy-2,5-dimethylphenyl)ethyl]benzamide,
3-{2-[(2R)-2-(6-Amino-pyridin-3-yl)-2-hydroxyethylamino]-2-methylpropyl}-N-[2-(4-hydroxy-2,3-dimethylphenyl)ethyl]benzamide,
3-{2-[(2R)-2-(6-Amino-pyridin-3-yl)-2-hydroxyethylamino]-2-methylpropyl}-N-[2-(4-hydroxy-2-methylphenyl)ethyl]benzamide,
3-{(2R)-2-[(2R)-2-(6-Aminopyridin-3-yl)-2-hydroxyethylamino]propyl}-N-[2-(4-hydroxy-2,5-dimethylphenyl)ethyl]benzamide,
3-{(2R)-2-[(2R)-2-(6-Aminopyridin-3-yl)-2-hydroxyethylamino]propyl}-N-[2-(4-hydroxy-2,3-dimethylphenyl)ethyl]benzamide,
3-{(2R)-2-[(2R)-2-(6-Aminopyridin-3-yl)-2-hydroxyethylamino]propyl}-N-[2-(4-hydroxy-2-methylphenyl)ethyl]benzamide,
2-[3-(2-{[(2R)-2-(6-aminopyridin-3-yl)-2-hydroxyethyl]amino}-2-methyl-propyl)phenyl]-N-(3-hydroxy-4-methoxy-phenyl)acetamide,
2-[3-(2-{[(2R)-2-(6-aminopyridin-3-yl)-2-hydroxyethyl]amino}-2-methyl-propyl)phenyl]-N-(3-hydroxy-phenyl)acetamide,
2-[3-(2-{[(2R)-2-(6-aminopyridin-3-yl)-2-hydroxyethyl]amino}-2-methyl-propyl)phenyl]-N-(2-chloro-4-hydroxy-phenyl)acetamide,
2-[3-(2-{[(2R)-2-(6-aminopyridin-3-yl)-2-hydroxyethyl]amino}-2-methyl-propyl)phenyl]-N-(4-hydroxy-3-methoxy-benzyl)acetamide,
2-[3-(2-{[(2R)-2-(6-aminopyridin-3-yl)-2-hydroxyethyl]amino}-2-methyl-propyl)phenyl]-N-[5-(ethylsulfonyl)-2-hydroxyphenyl]acetamide,
2-[3-(2-{[(2R)-2-(6-aminopyridin-3-yl)-2-hydroxyethyl]amino}-2-methyl-propyl)phenyl]-N-(2-hydroxy-5-methyl-phenyl)acetamide,
2-[3-(2-{[(2R)-2-(6-aminopyridin-3-yl)-2-hydroxyethyl]amino}-2-methyl-propyl)phenyl]-N-(5-chloro-2-hydroxy-benzyl)acetamide,
2-[3-(2-{[(2R)-2-(6-aminopyridin-3-yl)-2-hydroxyethyl]amino}-2-methyl-propyl)phenyl]-N-(4-hydroxy-1,1'-biph-enyl-3-yl)acetamide,
2-[3-(2-{[(2R)-2-(6-aminopyridin-3-yl)-2-hydroxyethyl]amino}-2-methyl-propyl)phenyl]-N-[2-hydroxy-2-(3-hydroxyphenyl)ethyl]-N-methyl-acetamide,
2-[3-(2-{[(2R)-2-(6-aminopyridin-3-yl)-2-hydroxyethyl]amino}-2-methyl-propyl)phenyl]-N-ethyl-N-(3-hydroxyphenyl)acetamide,
2-[3-(2-{[(2R)-2-(6-aminopyridin-3-yl)-2-hydroxyethyl]amino}-2-methyl-propyl)phenyl]-N-[2-(3-ethoxy-4-hydroxyphenyl)ethyl]acetamide,
2-[3-(2-{[(2R)-2-(6-aminopyridin-3-yl)-2-hydroxyethyl]amino}-2-methyl-propyl)phenyl]-N-{[4'-(hydroxymethyl)-1,1'-biphenyl-3-yl]methyl}acetamide,
2-[3-(2-{[(2R)-2-(6-aminopyridin-3-yl)-2-hydroxyethyl]amino}-2-methyl-propyl)phenyl]-N-(2,4-dichloro-6-hydroxybenzyl)acetamide,
2-[3-(2-{[(2R)-2-(6-aminopyridin-3-yl)-2-hydroxyethyl]amino}-2-methyl-propyl)phenyl]-N-[(3-fluoro-4'-hydroxy-1,1'-biphenyl-4-yl)meth-yl]acetamide,
2-[3-(2-{[(2R)-2-(6-aminopyridin-3-yl)-2-hydroxyethyl]amino}-2-methyl-propyl)phenyl]-N-[(4'-hydroxy-3-methyl-1,1'-biphenyl-4-yl)methyl]acetamide,
2-[3-(2-{[(2R)-2-(6-aminopyridin-3-yl)-2-hydroxyethyl]amino}-2-methyl-propyl)phenyl]-N-(2-chloro-5-hydroxy-benzyl)-N-ethylacetamide,
2-[3-(2-{[(2R)-2-(6-aminopyridin-3-yl)-2-hydroxyethyl]amino}-2-methyl-propyl)phenyl]-N-[(2'-hydroxy-1,1'-biphenyl-2-yl)methyl]acetamide,
2-[3-(2-{[(2R)-2-(6-aminopyridin-3-yl)-2-hydroxyethyl]amino}-2-methyl-propyl)phenyl]-N-[3-hydroxy-5-(trifluoro-methyl)benzyl]-N-methylacetamide,
2-[3-(2-{[(2R)-2-(6-aminopyridin-3-yl)-2-hydroxyethyl]amino}-2-methyl-propyl)phenyl]-N-(3-chloro-5-hydroxy-benzyl)-N-ethylacetamide,
2-[3-(2-{[(2R)-2-(6-aminopyridin-3-yl)-2-hydroxyethyl]amino}-2-methyl-propyl)phenyl]-N-(3-chloro-5-hydroxy-benzyl)acetamide,
2-[3-(2-{[(2R)-2-(6-aminopyridin-3-yl)-2-hydroxyethyl]amino}-2-methyl-propyl)phenyl]-N-(4-hydroxy-3,5-dimethylbenzyl)acetamide,
2-[3-(2-{[(2R)-2-(6-aminopyridin-3-yl)-2-hydroxyethyl]amino}-2-methyl-propyl)phenyl]-N-[2-(2-hydroxyphenyl)ethyl]acetamide,
2-[3-(2-{[(2R)-2-(6-aminopyridin-3-yl)-2-hydroxyethyl]amino}-2-methyl-propyl)phenyl]-N-benzyl-N-(4-hydroxyphenyl)acetamide,
2-[3-(2-{[(2R)-2-(6-aminopyridin-3-yl)-2-hydroxyethyl]amino}-2-methyl-propyl)phenyl]-N-[2-(4-hydroxyphenyl)-ethyl]acetamide,
2-[3-(2-{[(2R)-2-(6-aminopyridin-3-yl)-2-hydroxyethyl]amino}-2-methyl-propyl)phenyl]-N-(4-hydroxybenzyl)acetamide,
2-[3-(2-{[(2R)-2-(6-aminopyridin-3-yl)-2-hydroxyethyl]amino}-2-methyl-propyl)phenyl]-N-(2-hydroxybenzyl)acetamide,
2-[3-(2-{[(2R)-2-(6-aminopyridin-3-yl)-2-hydroxyethyl]amino}-2-methyl-propyl)phenyl]-N-(3-hydroxybenzyl)acetamide,
2-[3-(2-{[(2R)-2-(6-aminopyridin-3-yl)-2-hydroxyethyl]amino}-2-methyl-propyl)phenyl]-N-[2-(3-hydroxyphenyl)-ethyl]acetamide,
2-[3-(2-{[(2R)-2-(6-aminopyridin-3-yl)-2-hydroxyethyl]amino}-2-methyl-propyl)phenyl]-N-[2-(4-hydroxy-3-meth-oxyphenyl)ethyl]acetamide, methyl 4-({[3-(2-{[(2R)-2-(6-aminopyridin-3-yl)-2-hydroxyethyl]-amino}-2-methyl-propyl)phenyl]acetyl}amino)-3-hydroxybenzoate, 2-[3-(2-{[(2R)-2-(6-aminopyridin-3-yl)-2-hydroxyethyl]-amino}-2-methyl-propyl)phenyl]-N-(5-tert-butyl-2-hydroxy-phenyl)acetamide, 2-[3-(2-{[(2R)-2-(6-aminopyridin-3-yl)-2-hydroxyethyl]-amino}-2-methyl-propyl)phenyl]-N-(3-hydroxy-4-methyl-phenyl)acetamide, 2-[3-((2R)-2-{[(2R)-2-(6-aminopyridin-3-yl)-2-hydroxy-eth-yl]amino}propyl)phenyl]-N-[2-(4-hydroxyphenyl)ethyl]acetamide, 2-[3-((2R)-2-{[(2R)-2-(6-aminopyridin-3-yl)-2-hydroxyethyl]amino}propyl)phenyl]-N-(4-hydroxybenzyl)acetamide, 2-[3-((2R)-2-{[(2R)-2-(6-aminopyridin-3-yl)-2-hydroxyethyl]amino}propyl)phenyl]-N-(2-hydroxybenzyl)acetamide, 2-[3-((2R)-2-{[(2R)-2-(6-aminopyridin-3-yl)-2-hydroxyethyl]amino}propyl)phenyl]-N-(3-hydroxybenzyl)acetamide, 2-[3-((2R)-2-{[(2R)-2-(6-aminopyridin-3-yl)-2-hydroxyethyl]amino}propyl)phenyl]-N-[2-(3-hydroxyphenyl)ethyl]acetamide, 2-[3-((2R)-2-{[(2R)-2-(6-aminopyridin-3-yl)-2-hydroxyethyl]amino}propyl)phenyl]-N-[2-(4-hydroxy-3-methoxyphenyl)ethyl]acetamide, 2-[3-((2R)-2-{[(2R)-2-(6-aminopyridin-3-yl)-2-hydroxyethyl]amino}propyl)phenyl]-N-(5-tert-butyl-2-hydroxyphenyl)acetamide, 2-[3-((2R)-2-{[(2R)-2-(6-aminopyridin-3-yl)-2-hydroxyethyl]amino}propyl)phenyl]-N-(3-hydroxy-4-methyl-phenyl)acetamide, 2-[3-((2R)-2-{[(2R)-2-(6-aminopyridin-3-yl)-2-hydroxyethyl]amino}propyl)phenyl]-N-(3-hydroxy-4-methoxyphenyl)acetamide, 2-[3-((2R)-2-{[(2R)-2-(6-aminopyridin-3-yl)-2-hydroxyethyl]amino}propyl)phenyl]-N-(4-hydroxy-3-methoxybenzyl)acetamide, 2-[3-((2R)-2-{[(2R)-2-(6-aminopyridin-3-yl)-2-hydroxyethyl]amino}propyl)phenyl]-N-[5-(ethylsulfonyl)-2-hydroxyphenyl]acetamide, 2-[3-((2R)-2-{[(2R)-2-(6-aminopyridin-3-yl)-2-hydroxyethyl]amino}propyl)phenyl]-N-(2-hydroxy-5-methyl-phenyl)acetamide, 2-[3-((2R)-2-{[(2R)-2-(6-aminopyridin-3-yl)-2-hydroxyethyl]amino}propyl)phenyl]-N-(3-hydroxy-2-methyl-phenyl)acetamide, 2-[3-((2R)-2-{[(2R)-2-(6-aminopyridin-3-yl)-2-hydroxyethyl]amino}propyl)phenyl]-N-(5-chloro-2-hydroxybenzyl)-acetamide, 2-[3-((2R)-2-{[(2R)-2-(6-aminopyridin-3-yl)-2-hydroxyethyl]amino}propyl)phenyl]-N-[2-hydroxy-2-(3-hydroxyphenyl)ethyl]-N-methyl-acetamide, 2-[3-((2R)-2-{[(2R)-2-(6-aminopyridin-3-yl)-2-hydroxyethyl]amino}propyl)phenyl]-N-[2-(3-ethoxy-4-hydroxyphenyl)ethyl]acetamide, 2-[3-((2R)-2-{[(2R)-2-(6-aminopyridin-3-yl)-2-hydroxyethyl]amino}propyl)phenyl]-N-[2-(3-hydroxy-4-methoxy-phenyl)ethyl]acetamide, 2-[3-((2R)-2-{[(2R)-2-(6-aminopyridin-3-yl)-2-hydroxyethyl]amino}propyl)phenyl]-N-ethyl-N-[2-(4-hydroxyphen-yl)ethyl]acetamide, 2-[3-((2R)-2-{[(2R)-2-(6-aminopyridin-3-yl)-2-hydroxyethyl]amino}propyl)phenyl]-N-(2-chloro-4-hydroxybenzyl)-N-ethylacetamide, 2-[3-((2R)-2-{[(2R)-2-(6-aminopyridin-3-yl)-2-hydroxyethyl]amino}propyl)phenyl]-N-(5-hydroxy-1,2,3,4-tetrahydronaphthalen-1-yl)acetamide, 2-[3-((2R)-2-{[(2R)-2-(6-aminopyridin-3-yl)-2-hydroxyethyl]amino}propyl)phenyl]-N-(4-hydroxyphenyl)acetamide, 2-[3-((2R)-2-{[(2R)-2-(6-aminopyridin-3-yl)-2-hydroxyethyl]amino}propyl)phenyl]-N-[4-(4-hydroxyphenyl)butyl]acetamide, 2-[3-((2R)-2-{[(2R)-2-(6-aminopyridin-3-yl)-2-hydroxyethyl]amino}propyl)phenyl]-N-[(4'-hydroxy-1,1'-biphenyl-4-yl)meth-yl]acetamide, 2-[3-((2R)-2-{[(2R)-2-(6-aminopyridin-3-yl)-2-hydroxyethyl]amino}propyl)phenyl]-N-{[4'-(hydroxymethyl)-1,1'-biphenyl-3-yl]methyl}acetamide, 2-[3-((2R)-2-{[(2R)-2-(6-aminopyridin-3-yl)-2-hydroxyethyl]amino}propyl)phenyl]-N-(2,4-dichloro-6-hydroxybenzyl)acetamide, 2-[3-((2R)-2-{[(2R)-2-(6-aminopyridin-3-yl)-2-hydroxyethyl]amino}propyl)phenyl]-N-[(3-fluoro-4'-hydroxy-1,1'-biphenyl-4-yl)methyl]acetamide, 2-[3-((2R)-2-{[(2R)-2-(6-aminopyridin-3-yl)-2-hydroxyethyl]amino}propyl)phenyl]-N-[(4'-hydroxy-3-methyl-1,1'-biphenyl-4-yl)methyl]acetamide, 2-[3-((2R)-2-{[(2R)-2-(6-aminopyridin-3-yl)-2-hydroxyethyl]amino}propyl)phenyl]-N-(2-chloro-5-hydroxybenzyl)-N-ethylacetamide, 2-[3-((2R)-2-{[(2R)-2-(6-aminopyridin-3-yl)-2-hydroxyethyl]amino}propyl)phenyl]-N-[(2'-hydroxy-1,1'-biphenyl-2-yl)methyl]acetamide, 2-[3-((2R)-2-{[(2R)-2-(6-aminopyridin-3-yl)-2-hydroxyethyl]amino}propyl)phenyl]-N-[3-hydroxy-5-(trifluoromethyl)benzyl]-N-methylacetamide, 2-[3-((2R)-2-{[(2R)-2-(6-aminopyridin-3-yl)-2-hydroxyethyl]amino}propyl)phenyl]-N-(3-chloro-5-hydroxybenzyl)-N-ethylacetamide, 2-[3-((2R)-2-{[(2R)-2-(6-aminopyridin-3-yl)-2-hydroxyethyl]amino}propyl)phenyl]-N-(3-chloro-5-hydroxybenzyl)acetamide, 2-[3-((2R)-2-{[(2R)-2-(6-aminopyridin-3-yl)-2-hydroxyethyl]amino}propyl)phenyl]-N-(4-hydroxy-3,5-dimethylbenzyl)acetamide, 2-[3-((2R)-2-{[(2R)-2-(6-aminopyridin-3-yl)-2-hydroxyethyl]amino}propyl)phenyl]-N-(3,5-dichloro-2-hydroxybenzyl)acetamide, 3-(2-{[(2R)-2-(6-aminopyridin-3-yl)-2-hydroxyethyl]-amino}-2-methyl-propyl)-N-[2-(4-hydroxyphenyl)ethyl]benzamide, 3-(2-{[(2R)-2-(6-aminopyridin-3-yl)-2-hydroxyethyl]-amino}-2-methyl-propyl)-N-(4-hydroxybenzyl)benzamide, 3-(2-{[(2R)-2-(6-aminopyridin-3-yl)-2-hydroxyethyl]-amino}-2-methyl-propyl)-N-(2-hydroxybenzyl)benzamide, 3-(2-{[(2R)-2-(6-aminopyridin-3-yl)-2-hydroxyethyl]-amino}-2-methyl-propyl)-N-[2-(3-hydroxyphenyl)ethyl]benzamide, 3-(2-{[(2R)-2-(6-aminopyridin-3-yl)-2-hydroxyethyl]-amino}-2-methyl-propyl)-N-[2-(4-hydroxy-3-meth-oxyphenyl)ethyl]benzamide, 3-(2-{[(2R)-2-(6-aminopyridin-3-yl)-2-hydroxyethyl]-amino}-2-methyl-propyl)-N-(3-hydroxy-4-methyl-phenyl)benzamide, 3-(2-{[(2R)-2-(6-aminopyridin-3-yl)-2-hydroxyethyl]-amino}-2-methyl-propyl)-N-[2-(4-hydroxy-3,5-dimethoxyphenyl)ethyl]benzamide, 3-(2-{[(2R)-2-(6-aminopyridin-3-yl)-2-hydroxyethyl]-amino}-2-methyl-propyl)-N-(3-hydroxy-4-methoxyphenyl)benzamide, 3-(2-{[(2R)-2-(6-aminopyridin-3-yl)-2-hydroxyethyl]-amino}-2-methyl-propyl)-N-(3-hydroxyphenyl)benzamide, 3-(2-{[(2R)-2-(6-aminopyridin-3-yl)-2-hydroxyethyl]-amino}-2-methyl-propyl)-N-(4-hydroxy-3-methoxybenzyl)benzamide, 3-(2-{[(2R)-2-(6-aminopyridin-3-yl)-2-hydroxyethyl]-amino}-2-methyl-propyl)-N-[5-(ethylsulfonyl)-2-hydroxyphenyl]benzamide, 3-(2-{[(2R)-2-(6-aminopyridin-3-yl)-2-hydroxyethyl]-amino}-2-methyl-propyl)-N-(3-hydroxy-2-methyl-phenyl)benzamide, 3-(2-{[(2R)-2-(6-aminopyridin-3-yl)-2-hydroxyethyl]-amino}-2-methy-lpropyl)-N-(5-chloro-2-hydroxy-benzyl)benzamide, 3-(2-{[(2R)-2-(6-aminopyridin-3-yl)-2-hydroxyethyl]-amino}-2-methyl-propyl)-N-(4-hydroxy-1,1'-biphenyl-3-yl)benzamide, 3-(2-{[(2R)-2-(6-aminopyridin-3-yl)-2-hydroxyethyl]-amino}-2-methyl-propyl)-N-[2-hydroxy-2-(3-hydroxyphenyl)ethyl]-N-methylbenz-amide, 3-(2-{[(2R)-2-(6-aminopyridin-3-yl)-2-hydroxyethyl]-amino}-2-methyl-propyl)-N-(2-hydroxybenzyl)-N-methylbenzamide, 3-(2-{[(2R)-2-(6-aminopyridin-3-yl)-2-hydroxyethyl]-amino}-2-methyl-propyl)-N-(3,5-dichloro-2-hydroxybenzyl)benzamide, 3-(2-{[(2R)-2-(6-aminopyridin-3-yl)-2-hydroxyethyl]-amino}-2-methyl-propyl)-N-[2-(2-hydroxyphenyl)ethyl]benzamide, 3-(2-{[(2R)-2-(6-aminopyridin-3-yl)-2-hydroxyethyl]-amino}-2-methyl-propyl)-N-[2-(3-ethoxy-4-hydroxyphenyl)ethyl]benzamide, 3-(2-{[(2R)-2-(6-aminopyridin-3-yl)-2-hydroxyethyl]-amino}-2-methyl-propyl)-N-[2-(3-hydroxy4-methoxyphenyl)ethyl]benzamide, 2-[3-(2-{[(2R)-2-(6-aminopyridin-3-yl)-2-hydroxyethyl]-amino}-2-methyl-propyl)-benzoyl]-2,3,4,5-tetrahydro-1H-2-benzazepin-8-ol, 3-(2-{[(2R)-2-(6-aminopyridin-3-yl)-2-hydroxyethyl]-amino}-2-methyl-propyl)-N-[(4'-hydroxy-3-methyl-1,1'-biphenyl-4-yl)methyl]-benzamide, 3-(2-{[(2R)-2-(6-aminopyridin-3-yl)-2-hydroxyethyl]-amino}-2-methyl-pr-opyl)-N-[(3'hydroxy-1,1'-biphenyl-2-yl)-methyl]benzamide, 3-((2R)-2-{[(2R)-2-(6-aminopyridin-3-yl)-2-hydroxyethyl]-amino}propyl)-N-(5-chloro-2-hydroxy-benzyl)benzamide, 3-((2R)-2-{[(2R)-2-(6-aminopyridin-3-yl)-2-hydroxyethyl]-amino}propyl)-N-[2-hydroxy-2-(3-hydroxyphenyl)ethyl]-N-methylbenzamide, 3-((2R)-2-{[(2R)-2-(6-aminopyridin-3-yl)-2-hydroxyethyl]-amino}propyl)-N-(2-hydroxybenzyl)-N-methylbenzamide, 3-((2R)-2-{[(2R)-2-(6-aminopyridin-3-yl)-2-hydroxyethyl]-amino}propyl)-N-[2-(3-ethoxy-4-hydroxyphenyl)ethyl]benzamide, 3-((2R)-2-{[(2R)-2-(6-aminopyridin-3-yl)-2-hydroxyethyl]-amino}propyl)-N-[2-(3-hydroxy-4-methoxyphenyl)ethyl]benzamide, 2-[3-((2R)-2-{[(2R)-2-(6-aminopyridin-3-yl)-2-hydroxyethyl]-amino}propyl)benzoyl]-2,3,4,5-tetrahydro-1H-2-benzazepin-8-ol, 3-((2R)-2-{[(2R)-2-(6-aminopyridin-3-yl)-2-hydroxyethyl]-amino}propyl)-N-ethyl-N-[2-(4-hydroxyphenyl)ethyl]benzamide, 3-((2R)-2-{[(2R)-2-(6-aminopyridin-3-yl)-2-hydroxyethyl]-amino}propyl)-N-(2-chloro-4-hydroxy-benzyl)-N-ethylbenzamide, 3-((2R)-2-{[(2R)-2-(6-aminopyridin-3-yl)-2-hydroxyethyl]-amino}propyl)-N-(5-hydroxy-1,2,3,4-tetrahydronaphthalen-1-yl)benzamide, 2-{4-[3-((2R)-2-{[(2R)-2-(6-amino-pyridin-3-yl)-2-hydroxyethyl]amino}propyl)benzoyl]piperazin-1-yl}phenol, 3-((2R)-2-{[(2R)-2-(6-aminopyridin-3-yl)-2-hydroxyethyl]-amino}propyl)-N-(4-hydroxyphenyl)benzamide, 3-((2R)-2-{[(2R)-2-(6-aminopyridin-3-yl)-2-hydroxyethyl]-amino}propyl)-N-[4-(4-hydroxyphen-yl)butyl]benzamide, 3-((2R)-2-{[(2R)-2-(6-aminopyridin-3-yl)-2-hydroxyethyl]-amino}propyl)-N-[(4'-hydroxy-1,1'-biphenyl-4-yl)methyl]benzamide, 3-((2R)-2-{[(2R)-2-(6-aminopyridin-3-yl)-2-hydroxyethyl]-amino}propyl)-N-{[4'-(hydroxymethyl)-1,1'-biphenyl-3-yl]methyl}benzamide, 3-((2R)-2-{[(2R)-2-(6-aminopyridin-3-yl)-2-hydroxyethyl]-amino}propyl)-N-(2,4-dichloro-6-hydroxybenzyl)benzamide, 3-((2R)-2-{[(2R)-2-(6-aminopyridin-3-yl)-2-hydroxyethyl]-amino}propyl)-N-[(3-fluoro-4'-hydroxy-1,1'-biphenyl-4-yl)methyl]benzamide, 3-((2R)-2-{[(2R)-2-(6-aminopyridin-3-yl)-2-hydroxyethyl]-amino}propyl)-N-[(4'-hydroxy-3-methyl-1,1'-biphenyl-4-yl)methyl]benzamide, 3-((2R)-2-{[(2R)-2-(6-aminopyridin-3-yl)-2-hydroxyethyl]-amino}propyl)-N-(2-chloro-5-hydroxy-benzyl)-N-ethylbenzamide, 3-((2R)-2-{[(2R)-2-(6-aminopyridin-3-yl)-2-hydroxyethyl]-amino}propyl)-N-[(2'-hydroxy-1,1'-biphenyl-2-yl)methyl]benzamide, 3-((2R)-2-{[(2R)-2-(6-aminopyridin-3-yl)-2-hydroxyethyl]-amino}propyl)-N-[(4'-hydroxy-1,1'-biphenyl-2-yl)methyl]benzamide, 3-((2R)-2-{[(2R)-2-(6-aminopyridin-3-yl)-2-hydroxyethyl]-amino}propyl)-N-[3-hydroxy-5-(trifluoro-methyl)benzyl]-N-methylbenzamide, 3-((2R)-2-{[(2R)-2-(6-aminopyridin-3-yl)-2-hydroxyethyl]-amino}propyl)-N-(3-chloro-5-hydroxy-benzyl)-N-ethylbenzamide, 3-((2R)-2-{[(2R)-2-(6-aminopyridin-3-yl)-2-hydroxyethyl]-amino}propyl)-N-(3-chloro-5-hydroxy-benzyl)benzamide, 3-((2R)-2-{[(2R)-2-(6-aminopyridin-3-yl)-2-hydroxyethyl]-amino}propyl)-N-[(4'-hydroxy-1,1'-biphenyl-3-yl)methyl]benzamide, 3-((2R)-2-{[(2R)-2-(6-aminopyridin-3-yl)-2-hydroxyethyl]-amino}propyl)-N-(4-hydroxy-3,5-dimeth-ylbenzyl)benzamide, 3-((2R)-2-{[(2R)-2-(6-aminopyridin-3-yl)-2-hydroxyethyl]-amino}propyl)-N-(3,5-dichloro-2-hydroxybenzyl)benzamide, 3-((2R)-2-{[(2R)-2-(6-aminopyridin-3-yl)-2-hydroxyethyl]-amino}propyl)-N-[2-(2-hydroxyphenyl)-ethyl]benzamide, 3-((2R)-2-{[(2R)-2-(6-aminopyridin-3-yl)-2-hydroxyethyl]-amino}propyl)-N-(3-hydroxy4-methoxy-phenyl)benzamide, 3-((2R)-2-{[(2R)-2-(6-aminopyridin-3-yl)-2-hydroxyethyl]-amino}propyl)-N-(3-hydroxyphenyl)benzamide, 3-((2R)-2-{[(2R)-2-(6-aminopyridin-3-yl)-2-hydroxyethyl]-amino}propyl)-N-(4-hydroxy-3-methoxy-benzyl)benzamide, 3-((2R)-2-{[(2R)-2-(6-aminopyridin-3-yl)-2-hydroxyethyl]-amino}propyl)-N-[5-(ethylsulfonyl)-2-hydroxyphenyl]benzamide, 3-((2R)-2-{[(2R)-2-(6-aminopyridin-3-yl)-2-hydroxyethyl]-amino}propyl)-N-(2-hydroxy-5-methyl-phenyl)benzamide, 3-((2R)-2-{[(2R)-2-(6-aminopyridin-3-yl)-2-hydroxyethyl]-amino}propyl)-N-(3-hydroxy-2-methyl-phenyl)benzamide, 3-((2R)-2-{[(2R)-2-(6-aminopyridin-3-yl)-2-hydroxyethyl]-amino}propyl)-N-[2-(4-hydroxyphen-yl)ethyl]benzamide, 3-((2R)-2-{[(2R)-2-(6-aminopyridin-3-yl)-2-hydroxyethyl]-amino}propyl)-N-(4-hydroxybenzyl)benzamide, 3-((2R)-2-{[(2R)-2-(6-aminopyridin-3-yl)-2-hydroxyethyl]-amino}propyl)-N-(2-hydroxybenzyl)benzamide, 3-((2R)-2-{[(2R)-2-(6-aminopyridin-3-yl)-2-hydroxyethyl]-amino}propyl)-N-(3-hydroxybenzyl)benzamide, and 3-((2R)-2-{[(2R)-2-(6-aminopyridin-3-yl)-2-hydroxyethyl]-amino}propyl)-N-[2-(3-hydroxyphen-yl)ethyl]benzamide.

According to one aspect of the present invention, the compounds of formula (1) wherein the $(CH_2)_n$—$C(=O)Q^1$ group is in the meta position are generally preferred.

Pharmaceutically acceptable salts of the compounds of formula (1) include the acid addition and base salts thereof.

Suitable acid addition salts are formed from acids which form non-toxic salts. Examples include the acetate, aspartate, benzoate, besylate, bicarbonate/carbonate, bisulphate/sulphate, borate, camsylate, citrate, edisylate, esylate, formate, fumarate, gluceptate, gluconate, glucuronate, hexafluorophosphate, hibenzate, hydrochloride/chloride, hydrobromide/bromide, hydroiodide/iodide, isethionate, lactate, malate, maleate, malonate, mesylate, methylsulphate, naphthylate, 2-napsylate, nicotinate, nitrate, orotate, oxalate, palmitate, pamoate, phosphate/hydrogen phosphate/dihydrogen phosphate, saccharate, stearate, succinate, tartrate, tosylate and trifluoroacetate salts.

Suitable base salts are formed from bases which form non-toxic salts. Examples include the aluminium, arginine, benzathine, calcium, choline, diethylamine, diolamine, glycine, lysine, magnesium, meglumine, olamine, potassium, sodium, tromethamine and zinc salts.

Hemisalts of acids and bases may also be formed, for example, hemisulphate and hemicalcium salts.

For a review on suitable salts, see "Handbook of Pharmaceutical Salts: Properties, Selection, and Use" by Stahl and Wermuth (Wiley-VCH, Weinheim, Germany, 2002).

Pharmaceutically acceptable salts of compounds of formula (1) may be prepared by one or more of three methods:

(i) by reacting the compound of formula (1) with the desired acid or base;

(ii) by removing an acid- or base-labile protecting group from a suitable precursor of the compound of formula (1) or by ring-opening a suitable cyclic precursor, for example, a lactone or lactam, using the desired acid or base; or (iii) by converting one salt of the compound of formula (1) to another by reaction with an appropriate acid or base or by means of a suitable ion exchange column.

All three reactions are typically carried out in solution. The resulting salt may precipitate out and be collected by filtration or may be recovered by evaporation of the solvent.

The degree of ionisation in the resulting salt may vary from completely ionised to almost non-ionised.

The compounds of the invention may exist in both unsolvated and solvated forms. The term 'solvate' is used herein to describe a molecular complex comprising the compound of the invention and a stoichiometric amount of one or more pharmaceutically acceptable solvent molecules, for example, ethanol. The term 'hydrate' is employed when said solvent is water.

Included within the scope of the invention are complexes such as clathrates, drug-host inclusion complexes wherein, in contrast to the aforementioned solvates, the drug and host are present in stoichiometric or non-stoichiometric amounts. Also included are complexes of the drug containing two or more organic and/or inorganic components which may be in stoichiometric or non-stoichiometric amounts. The resulting complexes may be ionised, partially ionised, or non-ionised. For a review of such complexes, see J Pharm Sci, 64 (8), 1269-1288 by Haleblian (August 1975).

Hereinafter all references to compounds of formula (1) include references to salts, solvates and complexes thereof and to solvates and complexes of salts thereof.

The compounds of the invention include compounds of formula (1) as hereinbefore defined, including all polymorphs and crystal habits thereof, prodrugs and isomers thereof (including optical, geometric and tautomeric isomers) as hereinafter defined and isotopically-labeled compounds of formula (1).

As indicated, so-called 'pro-drugs' of the compounds of formula (1) are also within the scope of the invention. Thus certain derivatives of compounds of formula (1) which may have little or no pharmacological activity themselves can, when administered into or onto the body, be converted into compounds of formula (1) having the desired activity, for example, by hydrolytic cleavage. Such derivatives are referred to as 'prodrugs'. Further information on the use of prodrugs may be found in 'Pro-drugs as Novel Delivery Systems, Vol. 14, ACS Symposium Series (T. Higuchi and W. Stella) and 'Bioreversible Carriers in Drug Design', Pergamon Press, 1987 (ed. E. B Roche, American Pharmaceutical Association).

Prodrugs in accordance with the invention can, for example, be produced by replacing appropriate functionalities present in the compounds of formula (1) with certain moieties known to those skilled in the art as 'pro-moieties' as described, for example, in "Design of Prodrugs" by H. Bundgaard (Elsevier, 1985).

Some examples of prodrugs in accordance with the invention include:

(i) where the compound of formula (1) contains a carboxylic acid functionality (—COOH), an ester thereof, for example, a compound wherein the hydrogen of the carboxylic acid functionality of the compound of formula (1) is replaced by $(C_1$-$C_8)$alkyl;

(ii) where the compound of formula (1) contains an alcohol functionality (—OH), an ether thereof, for example, a compound wherein the hydrogen of the alcohol functionality of the compound of formula (1) is replaced by $(C_1$-$C_6)$alkanoyloxymethyl; and (iii) where the compound of formula (1) contains a primary or secondary amino functionality (—NH$_2$ or —NHR where R≠H), an amide thereof, for example, a compound wherein, as the case may be, one or both hydrogens of the amino functionality of the compound of formula (1) is/are replaced by $(C_1$-$C_{10})$alkanoyl.

Further examples of replacement groups in accordance with the foregoing examples and examples of other prodrug types may be found in the aforementioned references.

Moreover, certain compounds of formula (1) may themselves act as prodrugs of other compounds of formula (1).

Also included within the scope of the invention are metabolites of compounds of formula (1), that is, compounds formed in vivo upon administration of the drug. Some examples of metabolites in accordance with the invention include (i) where the compound of formula (1) contains a methyl group, an hydroxymethyl derivative thereof (—CH$_3$→—CH$_2$OH):
(ii) where the compound of formula (1) contains an alkoxy group, an hydroxy derivative thereof (—OR→—OH);
(iii) where the compound of formula (1) contains a tertiary amino group, a secondary amino derivative thereof (—NR$^1$R$^2$→—NHR$^1$ or —NHR$^2$);
(iv) where the compound of formula (1) contains a secondary amino group, a primary derivative thereof (—NHR$^1$→—NH$_2$);
(v) where the compound of formula (1) contains a phenyl moiety, a phenol derivative thereof (-Ph→-PhOH); and
(vi) where the compound of formula (1) contains an amide group, a carboxylic acid derivative thereof (—CONH$_2$→COOH).

Compounds of formula (1) containing one or more asymmetric carbon atoms can exist as two or more stereoisomers. Where a compound of formula (1) contains an alkenyl or alkenylene group, geometric cis/trans (or Z/E) isomers are possible. Where structural isomers are interconvertible via a low energy barrier, tautomeric isomerism ('tautomerism') can occur. This can take the form of proton tautomerism in compounds of formula (1) containing, for example, an imino, keto, or oxime group, or so-called valence tautomerism in compounds which contain an aromatic moiety. It follows that a single compound may exhibit more than one type of isomerism.

Included within the scope of the present invention are all stereoisomers, geometric isomers and tautomeric forms of the compounds of formula (1), including compounds exhibiting more than one type of isomerism, and mixtures of one or more thereof. Also included are acid addition or base salts wherein the counterion is optically active, for example, d-lactate or l-lysine, or racemic, for example, dl-tartrate or dl-arginine.

Cis/trans isomers may be separated by conventional techniques well known to those skilled in the art, for example, chromatography and fractional crystallisation.

Conventional techniques for the preparation/isolation of individual enantiomers include chiral synthesis from a suitable optically pure precursor or resolution of the racemate (or the racemate of a salt or derivative) using, for example, chiral high pressure liquid chromatography (HPLC).

Alternatively, the racemate (or a racemic precursor) may be reacted with a suitable optically active compound, for example, an alcohol, or, in the case where the compound of formula (1) contains an acidic or basic moiety, an acid or base such as tartaric acid or 1-phenylethylamine. The resulting diastereomeric mixture may be separated by chromatography and/or fractional crystallization and one or both of the diastereoisomers converted to the corresponding pure enantiomer(s) by means well known to a skilled person.

Chiral compounds of the invention (and chiral precursors thereof) may be obtained in enantiomerically-enriched form using chromatography, typically HPLC, on an asymmetric resin with a mobile phase consisting of a hydrocarbon, typically heptane or hexane, containing from 0 to 50% by volume of isopropanol, typically from 2% to 20%, and from 0 to 5% by volume of an alkylamine, typically 0.1% diethylamine. Concentration of the eluate affords the enriched mixture.

Stereoisomeric conglomerates may be separated by conventional techniques known to those skilled in the art—see, for example, "Stereochemistry of Organic Compounds" by E. L. Eliel (Wiley, New York, 1994).

According to one aspect of the present invention, the (R,R)-stereoisomer of the formula below, wherein n and Q$^1$ are as defined above, is generally preferred:

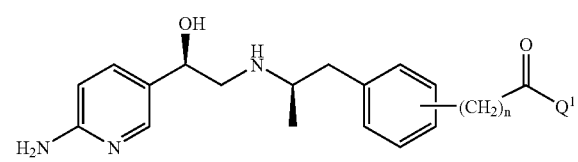

The present invention includes all pharmaceutically acceptable isotopically-labelled compounds of formula (1) wherein one or more atoms are replaced by atoms having the same atomic number, but an atomic mass or mass number different from the atomic mass or mass number which predominates in nature.

Examples of isotopes suitable for inclusion in the compounds of the invention include isotopes of hydrogen, such as $^2$H and $^3$H, carbon, such as $^{11}$C, $^{13}$C and $^{14}$C, chlorine, such as $^{36}$Cl, fluorine, such as $^{18}$F, iodine, such as $^{123}$I and $^{125}$I, nitrogen, such as $^{13}$N and $^{15}$N, oxygen, such as $^{15}$O, $^{17}$O and $^{18}$O, phosphorus, such as $^{32}$P, and sulphur, such as $^{35}$S.

Certain isotopically-labelled compounds of formula (1), for example, those incorporating a radioactive isotope, are useful in drug and/or substrate tissue distribution studies. The radioactive isotopes tritium, i.e. $^3$H, and carbon-14, i.e. $^{14}$C, are particularly useful for this purpose in view of their ease of incorporation and ready means of detection.

Substitution with heavier isotopes such as deuterium, i.e. $^2$H, may afford certain therapeutic advantages resulting from greater metabolic stability, for example, increased in vivo half-life or reduced dosage requirements, and hence may be preferred in some circumstances.

Substitution with positron emitting isotopes, such as $^{11}$C, $^{18}$F, $^{15}$O and $^{13}$N, can be useful in Positron Emission Topography (PET) studies for examining substrate receptor occupancy.

Isotopically-labeled compounds of formula (1) can generally be prepared by conventional techniques known to those skilled in the art or by processes analogous to those described in the accompanying Examples and Preparations using an appropriate isotopically-labeled reagents in place of the non-labeled reagent previously employed. Pharmaceutically acceptable solvates in accordance with the invention include those wherein the solvent of crystallization may be isotopically substituted, e.g. D$_2$O, d$_6$-acetone, d$_6$-DMSO.

The compounds of formula (1), their pharmaceutically acceptable salts and/or derived forms, are valuable pharmaceutically active compounds, which are suitable for the therapy and prophylaxis of numerous disorders in which the β2 receptor is involved or in which agonism of this receptor may induce benefit, in particular the allergic and non-allergic airways diseases but also in the treatment of other diseases such as, but not limited to those of the nervous system, premature labor, congestive heart failure, depression, inflammatory and allergic skin diseases, psoriasis, proliferative skin diseases, glaucoma and in conditions where there is an advantage in lowering gastric acidity, particularly in gastric and peptic ulceration.

Compounds of the invention intended for pharmaceutical use may be administered as crystalline or amorphous products. They may be obtained, for example, as solid plugs, powders, or films by methods such as precipitation, crystallization, freeze drying, spray drying, or evaporative drying. Microwave or radio frequency drying may be used for this purpose.

They may be administered alone or in combination with one or more other compounds of the invention or in combination with one or more other drugs (or as any combination thereof). Generally, they will be administered as a formulation in association with one or more pharmaceutically acceptable excipients. The term "excipient" is used herein to describe any ingredient other than the compound(s) of the invention. The choice of excipient will to a large extent depend on factors such as the particular mode of administration, the effect of the excipient on solubility and stability, and the nature of the dosage form.

Pharmaceutical compositions suitable for the delivery of compounds of the present invention and methods for their preparation will be readily apparent to those skilled in the art. Such compositions and methods for their preparation may be found, for example, in 'Remington's Pharmaceutical Sciences', 19th Edition (Mack Publishing Company, 1995).

The compounds of the invention may be administered orally. Oral administration may involve swallowing, so that the compound enters the gastrointestinal tract, or buccal or sublingual administration may be employed by which the compound enters the blood stream directly from the mouth.

Formulations suitable for oral administration include solid formulations such as tablets, capsules containing particulates, liquids, or powders, lozenges (including liquid-filled), chews, multi- and nano-particulates, gels, solid solution, liposome, films, ovules, sprays and liquid formulations.

Liquid formulations include suspensions, solutions, syrups and elixirs. Such formulations may be employed as fillers in soft or hard capsules and typically comprise a carrier, for example, water, ethanol, polyethylene glycol, propylene glycol, methylcellulose, or a suitable oil, and one or more emulsifying agents and/or suspending agents. Liquid formulations may also be prepared by the reconstitution of a solid, for example, from a sachet.

The compounds of the invention may also be used in fast-dissolving, fast-disintegrating dosage forms such as those described in Expert Opinion in Therapeutic Patents, 11 (6), 981-986, by Liang and Chen (2001).

For tablet dosage forms, depending on dose, the drug may make up from 1 weight % to 80 weight % of the dosage form, more typically from 5 weight % to 60 weight % of the dosage form. In addition to the drug, tablets generally contain a disintegrant. Examples of disintegrants include sodium starch glycolate, sodium carboxymethyl cellulose, calcium carboxymethyl cellulose, croscarmellose sodium, crospovidone, polyvinylpyrrolidone, methyl cellulose, microcrystalline cellulose, lower alkyl-substituted hydroxypropyl cellulose, starch, pregelatinised starch and sodium alginate. Generally, the disintegrant will comprise from 1 weight % to 25 weight %, preferably from 5 weight % to 20 weight % of the dosage form.

Binders are generally used to impart cohesive qualities to a tablet formulation. Suitable binders include microcrystalline cellulose, gelatin, sugars, polyethylene glycol, natural and synthetic gums, polyvinylpyrrolidone, pregelatinised starch, hydroxypropyl cellulose and hydroxypropyl methylcellulose. Tablets may also contain diluents, such as lactose (monohydrate, spray-dried monohydrate, anhydrous and the like), mannitol, xylitol, dextrose, sucrose, sorbitol, microcrystalline cellulose, starch and dibasic calcium phosphate dihydrate.

Tablets may also optionally comprise surface active agents, such as sodium lauryl sulfate and polysorbate 80, and glidants such as silicon dioxide and talc. When present, surface active agents may comprise from 0.2 weight % to 5 weight % of the tablet, and glidants may comprise from 0.2 weight % to 1 weight % of the tablet.

Tablets also generally contain lubricants such as magnesium stearate, calcium stearate, zinc stearate, sodium stearyl fumarate, and mixtures of magnesium stearate with sodium lauryl sulphate. Lubricants generally comprise from 0.25 weight % to 10 weight %, preferably from 0.5 weight % to 3 weight % of the tablet.

Other possible ingredients include anti-oxidants, colourants, flavouring agents, preservatives and taste-masking agents.

Exemplary tablets contain up to about 80% drug, from about 10 weight % to about 90 weight % binder, from about 0 weight % to about 85 weight % diluent, from about 2 weight % to about 10 weight % disintegrant, and from about 0.25 weight % to about 10 weight % lubricant.

Tablet blends may be compressed directly or by roller to form tablets. Tablet blends or portions of blends may alternatively be wet-, dry-, or melt-granulated, melt congealed, or extruded before tabletting. The final formulation may comprise one or more layers and may be coated or uncoated; it may even be encapsulated.

The formulation of tablets is discussed in Pharmaceutical Dosage Forms: Tablets, Vol. 1, by H. Lieberman and L. Lachman (Marcel Dekker, New York, 1980).

Consumable oral films for human or veterinary use are typically pliable water-soluble or water-swellable thin film dosage forms which may be rapidly dissolving or mucoadhesive and typically comprise a compound of formula (1), a film-forming polymer, a binder, a solvent, a humectant, a plasticiser, a stabiliser or emulsifier, a viscosity-modifying agent and a solvent. Some components of the formulation may perform more than one function.

The compound of formula (1) may be water-soluble or insoluble. A water-soluble compound typically comprises from 1 weight % to 80 weight %, more typically from 20 weight % to 50 weight %, of the solutes. Less soluble compounds may comprise a greater proportion of the composition, typically up to 88 weight % of the solutes. Alternatively, the compound of formula (1) may be in the form of multiparticulate beads.

The film-forming polymer may be selected from natural polysaccharides, proteins, or synthetic hydrocolloids and is typically present in the range 0.01 to 99 weight %, more typically in the range 30 to 80 weight %.

Other possible ingredients include anti-oxidants, colorants, flavourings and flavour enhancers, preservatives, salivary stimulating agents, cooling agents, co-solvents (including oils), emollients, bulking agents, anti-foaming agents, surfactants and taste-masking agents.

Films in accordance with the invention are typically prepared by evaporative drying of thin aqueous films coated onto a peelable backing support or paper. This may be done in a drying oven or tunnel, typically a combined coater dryer, or by freeze-drying or vacuuming.

Solid formulations for oral administration may be formulated to be immediate and/or modified release. Modified release formulations include delayed-, sustained-, pulsed-, controlled-, targeted and programmed release.

Suitable modified release formulations for the purposes of the invention are described in U.S. Pat. No. 6,106,864. Details of other suitable release technologies such as high energy dispersions and osmotic and coated particles are to be found in Pharmaceutical Technology On-line, 25(2), 1-14, by Verma et al (2001). The use of chewing gum to achieve controlled release is described in WO 00/35298.

The compounds of the invention may also be administered directly into the blood stream, into muscle, or into an internal organ. Suitable means for parenteral administration include intravenous, intraarterial, intraperitoneal, intrathecal, intraventricular, intraurethral, intrasternal, intracranial, intramuscular and subcutaneous. Suitable devices for parenteral administration include needle (including microneedle) injectors, needle-free injectors and infusion techniques.

Parenteral formulations are typically aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water.

The preparation of parenteral formulations under sterile conditions, for example, by lyophilisation, may readily be accomplished using standard pharmaceutical techniques well known to those skilled in the art.

The solubility of compounds of formula (1) used in the preparation of parenteral solutions may be increased by the use of appropriate formulation techniques, such as the incorporation of solubility-enhancing agents.

Formulations for parenteral administration may be formulated to be immediate and/or modified release. Modified release formulations include delayed-, sustained-, pulsed-, controlled-, targeted and programmed release. Thus compounds of the invention may be formulated as a solid, semi-solid, or thixotropic liquid for administration as an implanted depot providing modified release of the active compound. Examples of such formulations include drug-coated stents and poly(dl-lactic-coglycolic)acid (PGLA)_ microspheres.

The compounds of the invention may also be administered topically to the skin or mucosa, that is, dermally or transdermally. Typical formulations for this purpose include gels, hydrogels, lotions, solutions, creams, ointments, dusting powders, dressings, foams, films, skin patches, wafers, implants, sponges, fibres, bandages and microemulsions. Liposomes may also be used. Typical carriers include alcohol, water, mineral oil, liquid petrolatum, white petrolatum, glycerin, polyethylene glycol and propylene glycol. Penetration enhancers may be incorporated—see, for example, J Pharm Sci, 88 (10), 955-958 by Finnin and Morgan (October 1999).

Other means of topical administration include delivery by electroporation, iontophoresis, phonophoresis, sonophoresis and microneedle or needle-free (e.g. Powderject™, Bioject™, etc.) injection.

Formulations for topical administration may be formulated to be immediate and/or modified release. Modified release formulations include delayed-, sustained-, pulsed-, controlled-, targeted and programmed release.

The compounds of the invention can also be administered intranasally or by inhalation, typically in the form of a dry powder (either alone, as a mixture, for example, in a dry blend with lactose, or as a mixed component particle, for example, mixed with phospholipids, such as phosphatidylcholine) from a dry powder inhaler or as an aerosol spray from a pressurised container, pump, spray, atomiser (preferably an atomiser using electrohydrodynamics to produce a fine mist), or nebuliser, with or without the use of a suitable propellant, such as 1,1,1,2-tetrafluoroethane or 1,1,1,2,3,3,3-heptafluoropropane. For intranasal use, the powder may comprise a bioadhesive agent, for example, chitosan or cyclodextrin.

The pressurised container, pump, spray, atomizer, or nebuliser contains a solution or suspension of the compound(s) of the invention comprising, for example, ethanol, aqueous ethanol, or a suitable alternative agent for dispersing, solubilising, or extending release of the active, a propellant(s) as solvent and an optional surfactant, such as sorbitan trioleate, oleic acid, or an oligolactic acid.

Prior to use in a dry powder or suspension formulation, the drug product is micronised to a size suitable for delivery by inhalation (typically less than 5 microns). This may be achieved by any appropriate comminuting method, such as spiral jet milling, fluid bed jet milling, supercritical fluid processing to form nanoparticles, high pressure homogenisation, or spray drying.

Capsules (made, for example, from gelatin or hydroxypropylmethylcellulose), blisters and cartridges for use in an inhaler or insufflator may be formulated to contain a powder mix of the compound of the invention, a suitable powder base such as lactose or starch and a performance modifier such as l-leucine, mannitol, or magnesium stearate. The lactose may be anhydrous or in the form of the monohydrate, preferably the latter. Other suitable excipients include dextran, glucose, maltose, sorbitol, xylitol, fructose, sucrose and trehalose.

A suitable solution formulation for use in an atomiser using electrohydrodynamics to produce a fine mist may contain from 1 µg to 20 mg of the compound of the invention per actuation and the actuation volume may vary from 1 µl to 100 µl. A typical formulation may comprise a compound of formula (1), propylene glycol, sterile water, ethanol and sodium chloride. Alternative solvents which may be used instead of propylene glycol include glycerol and polyethylene glycol.

Suitable flavours, such as menthol and levomenthol, or sweeteners, such as saccharin or saccharin sodium, may be added to those formulations of the invention intended for inhaled/intranasal administration.

Formulations for inhaled/intranasal administration may be formulated to be immediate and/or modified release using, for example, PGLA. Modified release formulations include delayed-, sustained-, pulsed-, controlled-, targeted and programmed release.

In the case of dry powder inhalers and aerosols, the dosage unit is determined by means of a valve which delivers a metered amount. Units in accordance with the invention are typically arranged to administer a metered dose or "puff" containing from 0.001 mg to 10 mg of the compound of formula (1). The overall daily dose will typically be in the range 0.001 mg to 40 mg which may be administered in a single dose or, more usually, as divided doses throughout the day.

The compounds of formula (1) are particularly suitable for an administration by inhalation The compounds of the invention may be administered rectally or vaginally, for example, in the form of a suppository, pessary, or enema. Cocoa butter is a traditional suppository base, but various alternatives may be used as appropriate.

Formulations for rectal/vaginal administration may be formulated to be immediate and/or modified release. Modified release formulations include delayed-, sustained-, pulsed-, controlled-, targeted and programmed release.

The compounds of the invention may also be administered directly to the eye or ear, typically in the form of drops of a micronised suspension or solution in isotonic, pH-adjusted, sterile saline. Other formulations suitable for ocular and aural administration include ointments, biodegradable (e.g. absorbable gel sponges, collagen) and non-biodegradable (e.g. silicone) implants, wafers, lenses and particulate or vesicular systems, such as niosomes or liposomes. A polymer such as crossed-linked polyacrylic acid, polyvinylalcohol, hyaluronic acid, a cellulosic polymer, for example, hydroxypropylmethylcellulose, hydroxyethylcellulose, or methyl cellulose, or a heteropolysaccharide polymer, for example, gelan gum, may be incorporated together with a preservative, such as benzalkonium chloride. Such formulations may also be delivered by iontophoresis.

Formulations for ocular/aural administration may be formulated to be immediate and/or modified release. Modified release formulations include delayed-, sustained-, pulsed-, controlled-, targeted, or programmed release.

The compounds of the invention may be combined with soluble macromolecular entities, such as cyclodextrin and suitable derivatives thereof or polyethylene glycol-containing polymers, in order to improve their solubility, dissolution rate, taste-masking, bioavailability and/or stability for use in any of the aforementioned modes of administration.

Drug-cyclodextrin complexes, for example, are found to be generally useful for most dosage forms and administration routes. Both inclusion and non-inclusion complexes may be used. As an alternative to direct complexation with the drug, the cyclodextrin may be used as an auxiliary additive, i.e. as a carrier, diluent, or solubiliser. Most commonly used for these purposes are alpha-, beta- and gamma-cyclodextrins, examples of which may be found in International Patent Applications Nos. WO 91/11172, WO 94/02518 and WO 98/55148.

Inasmuch as it may desirable to administer a combination of active compounds, for example, for the purpose of treating a particular disease or condition, it is within the scope of the present invention that two or more pharmaceutical compositions, at least one of which contains a compound in accordance with the invention, may conveniently be combined in the form of a kit suitable for coadministration of the compositions.

Thus the kit of the invention comprises two or more separate pharmaceutical compositions, at least one of which contains a compound of formula (1) in accordance with the invention, and means for separately retaining said compositions, such as a container, divided bottle, or divided foil packet. An example of such a kit is the familiar blister pack used for the packaging of tablets, capsules and the like.

The kit of the invention is particularly suitable for administering different dosage forms, for example parenteral, for administering the separate compositions at different dosage intervals, or for titrating the separate compositions against one another. To assist compliance, the kit typically comprises directions for administration and may be provided with a so-called memory aid.

For administration to human patients, the total daily dose of the compounds of the invention is typically in the range 0.001 mg to 5000 mg depending, of course, on the mode of administration. For example, an intravenous daily dose may only require from 0.001 mg to 40 mg. The total daily dose may be administered in single or divided doses and may, at the physician's discretion, fall outside of the typical range given herein.

These dosages are based on an average human subject having a weight of about 65 kg to 70 kg. The physician will readily be able to determine doses for subjects whose weight falls outside this range, such as infants and the elderly.

For the avoidance of doubt, references herein to "treatment" include references to curative, palliative and prophylactic treatment.

According to another embodiment of the present invention, the compounds of the formula (1), or pharmaceutically acceptable salts, derived forms or compositions thereof, can also be used as a combination with one or more additional therapeutic agents to be co-administered to a patient to obtain some particularly desired therapeutic end result such as the treatment of pathophysiologically-relevant disease processes including, but not limited to (i) bronchoconstriction, (ii) inflammation, (iii) allergy, (iv) tissue destruction, (v) signs and symptoms such as breathlessness, cough. The second and more additional therapeutic agents may also be a compound of the formula (1), or a pharmaceutically acceptable salt, derived forms or compositions thereof, or one or more β2 agonists known in the art. More typically, the second and more therapeutic agents will be selected from a different class of therapeutic agents.

As used herein, the terms "co-administration", "co-administered" and "in combination with", referring to the compounds of formula (1) and one or more other therapeutic agents, is intended to mean, and does refer to and include the following:

simultaneous administration of such combination of compound(s) of formula (1) and therapeutic agent(s) to a patient in need of treatment, when such components are formulated together into a single dosage form which releases said components at substantially the same time to said patient, substantially simultaneous administration of such combination of compound(s) of formula (1) and therapeutic agent(s) to a patient in need of treatment, when such components are formulated apart from each other into separate dosage forms which are taken at substantially the same time by said patient, whereupon said components are released at substantially the same time to said patient, sequential administration of such combination compound(s) of formula (1) and therapeutic agent(s) to a patient in need of treatment, when such components are formulated apart from each other into separate dosage forms which are taken at consecutive times by said patient with a significant time interval between each administration, whereupon said components are released at substantially different times to said patient; and sequential administration of such combination of compound(s) of formula (1) and therapeutic agent(s) to a patient in need of treatment, when such components are formulated together into a single dosage form which releases said components in a controlled manner whereupon they are concurrently, consecutively, and/or overlapingly administered at the same and/or different times by said patient, where each part may be administered by either the same or different route.

Suitable examples of other therapeutic agents which may be used in combination with the compound(s) of formula (1), or pharmaceutically acceptable salts, derived forms or compositions thereof, include, but are by no means limited to:
(a) 5-Lipoxygenase (5-LO) inhibitors or 5-lipoxygenase activating protein (FLAP) antagonists,
(b) Leukotriene antagonists (LTRAs) including antagonists of $LTB_4$, $LTC_4$, $LTD_4$, and $LTE_4$,
(c) Histamine receptor antagonists including H1 and H3 antagonists,
(d) $\alpha_1$- and $\alpha_2$-adrenoceptor agonist vasoconstrictor sympathomimetic agents for decongestant use,
(e) muscarinic M3 receptor antagonists or anticholinergic agents,
(f) PDE inhibitors, e.g. PDE3, PDE4 and PDE5 inhibitors,
(g) Theophylline,
(h) Sodium cromoglycate,
(i) COX inhibitors both non-selective and selective COX-1 or COX-2 inhibitors (NSAIDs),
(j) Oral and inhaled glucocorticosteroids,
(k) Monoclonal antibodies active against endogenous inflammatory entities,
(l) Anti-tumor necrosis factor (anti-TNF-$\alpha$) agents,
(m) Adhesion molecule inhibitors including VLA-4 antagonists,
(n) Kinin-$B_1$- and $B_2$-receptor antagonists,
(o) Immunosuppressive agents,
(p) Inhibitors of matrix metalloproteases (MMPs),
(q) Tachykinin $NK_1$, $NK_2$ and $NK_3$ receptor antagonists,
(r) Elastase inhibitors,
(s) Adenosine A2a receptor agonists,
(t) Inhibitors of urokinase,
(u) Compounds that act on dopamine receptors, e.g. D2 agonists,
(v) Modulators of the NF$\kappa\beta$ pathway, e.g. IKK inhibitors,
(w) modulators of cytokine signalling pathyways such as p38 MAP kinase or syk kinase,
(x) Agents that can be classed as mucolytics or anti-tussive, and
(y) Antibiotics.

According to the present invention, combination of the compounds of formula (1) with:
H3 antagonists,
Muscarinic M3 receptor antagonists,
PDE4 inhibitors,
glucocorticosteroids,
Adenosine A2a receptor agonists,
Modulators of cytokine signalling pathyways such as p38 MAP kinase or syk kinase, or,
Leukotriene antagonists (LTRAs) including antagonists of $LTB_4$, $LTC_4$, $LTD_4$, and $LTE_4$,
are further preferred.

According to the present invention, combination of the compounds of formula (1) with:
glucocorticosteroids, in particular inhaled glucocorticosteroids with reduced systemic side effects, including prednisone, prednisolone, flunisolide, triamcinolone acetonide, beclomethasone dipropionate, budesonide, fluticasone propionate, ciclesonide, and mometasone furoate, or
muscarinic M3 receptor antagonists or anticholinergic agents including in particular ipratropium salts, namely bromide, tiotropium salts, namely bromide, oxitropium salts, namely bromide, perenzepine, and telenzepine,
are further preferred.

It is to be appreciated that all references herein to treatment include curative, palliative and prophylactic treatment. The description, which follows, concerns the therapeutic applications to which the compounds of formula (1) may be put.

The compounds of formula (1) have the ability to interact with the β2 receptor and thereby have a wide range of therapeutic applications, as described further below, because of the essential role which the β2 receptor plays in the physiology of all mammals.

Therefore, a further aspect of the present invention relates to the compounds of formula (1), or pharmaceutically acceptable salts, derived forms or compositions thereof, for use in the treatment of diseases, disorders, and conditions in which the β2 receptor is involved. More specifically, the present invention also concerns the compounds of formula (1), or pharmaceutically acceptable salts, derived forms or compositions thereof, for use in the treatment of diseases, disorders, and conditions selected from the group consisting of:
asthma of whatever type, etiology, or pathogenesis, in particular asthma that is a member selected from the group consisting of atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome and bronchiolytis,
chronic or acute bronchoconstriction, chronic bronchitis, small airways obstruction, and emphysema,
obstructive or inflammatory airways diseases of whatever type, etiology, or pathogenesis, in particular an obstructive or inflammatory airways disease that is a member selected from the group consisting of chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy and airways disease that is associated with pulmonary hypertension,
bronchitis of whatever type, etiology, or pathogenesis, in particular bronchitis that is a member selected from the group consisting of acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis and vesicular bronchitis,
acute lung injury,
bronchiectasis of whatever type, etiology, or pathogenesis, in particular bronchiectasis that is a member selected from the group consisting of cylindric bronchiectasis, sacculated bronchiectasis, fusiform bronchiectasis, capillary bronchiectasis, cystic bronchiectasis, dry bronchiectasis and follicular bronchiectasis.

A still further aspect of the present invention also relates to the use of the compounds of formula (1), or pharmaceutically acceptable salts, derived forms or compositions thereof, for the manufacture of a drug having a β2 agonist activity. In particular, the present inventions concerns the use of the compounds of formula (1), or pharmaceutically acceptable salts, derived forms or compositions thereof, for the manufacture of a drug for the treatment of β2-mediated diseases and/or conditions, in particular the diseases and/or conditions listed above.

As a consequence, the present invention provides a particularly interesting method to treat a mammal, including a human being, with an effective amount of a compound of formula (1), or a pharmaceutically acceptable salt, derived form or composition thereof. More precisely, the present invention provides a particularly interesting method for the treatment of a β2-mediated diseases and/or conditions in a mammal, including a human being, in particular the diseases and/or conditions listed above, comprising admidministering said mammal with an effective amount of a compound of formula (1), its pharmaceutically acceptable salts and/or derived forms.

The following examples illustrate the preparation of the compounds of the formula (1):

EXAMPLE 1

2-(3-{(2R)-2-[(2R)-2-(6-Amino-pyridin-3-yl)-2-hydroxy-ethylamino]-propyl}-phenyl)-N-benzyl-acetamide

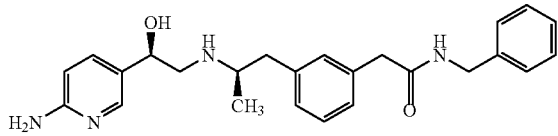

A solution of N-Benzyl-2-[3-((2R)-2-{(2R)-2-[6-(2,5-dimethyl-pyrrol-1-yl)-pyridin-3-yl]-2-hydroxy-ethylamino}-propyl)-phenyl]-acetamide (preparation 1, 148 mg, 0.30 mmol) in ethanol (5 ml) was treated with hydroxylamine hydrochloride (103 mg, 1.48 mmol) and the resulting mixture heated to 85C. for 48 hours. The reaction was cooled to room temperature and passed through a Strong Cation Exchange column eluting with methanol followed by 2N ammonia in methanol to elute the product. Further purification by flash column chromatography eluting with dichloromethane:methanol: 880 ammonia (97:3:0.5 changing to 90:10:1 by volume) gave the title compound as a pale yellow solid (36 mg).

$^1$H NMR (400 MHz, CD$_3$OD): δ=7.78 (1H, s), 7.37 (1H, d), 7.27-7.00 (9H, m), 6.51 (1H, s), 4.53 (1H, s), 4.35 (2H, s), 3.51 (2H, s), 2.90-2.82 (2H, m), 2.66-2.58 (3H, m), 1.07 (3H, d) ppm.

LRMS (APCl): m/z [M+H]$^+$ 419.

EXAMPLE 2

2-(3-{(2R)-2-[(2R)-2-(6-Amino-pyridin-3-yl)-2-hydroxy-ethylamino]-propyl}-phenyl)-N-(2-methoxy-benzyl)-acetamide

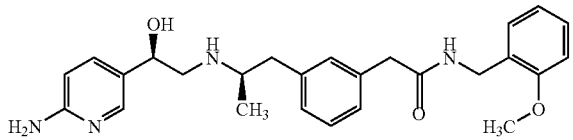

Prepared from 2-[3-((2R)-2-{(2R)-2-[6-(2,5-Dimethyl-pyrrol-1-yl)-pyridin-3-yl]-2-hydroxy-ethylamino}-propyl)-phenyl]-N-(2-methoxy-benzyl)-acetamide (preparation 2) according to the method for example 1 to give the title compound as a pale yellow foam.

$^1$H NMR (400 MHz, CD$_3$OD): δ=7.77 (1H, s), 7.36 (1H, d), 7.23-6.84 (8H, m), 6.50 (1H, d), 4.52 (1H, m), 4.34 (2H, s), 3.78 (3H, s), 3.50 (2H, s), 2.88-2.81 (2H, m), 2.66-2.57 (3H, m), 1.06 (3H, d) ppm.

LRMS (APCl): m/z [M+H]$^+$ 449.

EXAMPLE 3

2-(3-{(2R)-2-[(2R)-2-(6-Amino-pyridin-3-yl)-2-hydroxy-ethylamino]-propyl}-phenyl)-N-(2-ethoxy-benzyl)-acetamide

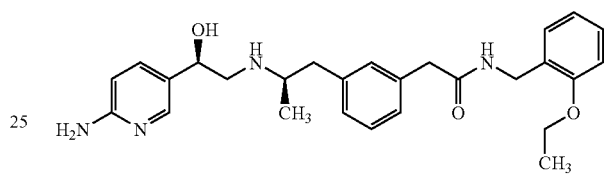

Prepared from 2-[3-((2R)-2-{(2R)-2-[6-(2,5-Dimethyl-pyrrol-1-yl)-pyridin-3-yl]-2-hydroxy-ethylamino}-propyl)-phenyl]-N-(2-ethoxy-benzyl)-acetamide (preparation 3) according to the method for example 1 to give the title compound as a pale yellow foam.

$^1$H NMR (400 MHz, CD$_3$OD): δ=7.78 (1H, s), 7.37 (1H, d), 7.21-7.00 (6H, m), 6.90 (1H, d), 6.83 (1H, t), 6.50 (1H, s), 4.52 (1H, m), 4.35 (2H, s), 3.99 (2H, m), 3.51 (2H, s), 2.89-2.81 (2H, m), 2.70-2.54 (3H, m), 1.34 (3H, d), 1.06 (3H, d) ppm.

LRMS (APCl): m/z [M+H]$^+$ 463.

EXAMPLE 4

2-(3-{(2R)-2-[(2R)-2-(6-Amino-pyridin-3-yl)-2-hydroxy-ethylamino]-propyl}-phenyl)-N-(3-phenyl-propyl)-acetamide

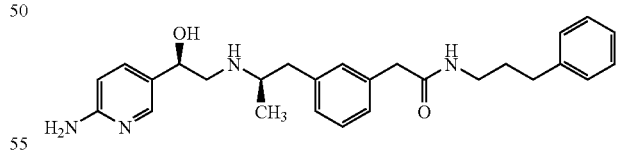

Prepared from 2-[3-((2R)-2-{(2R)-2-[6-(2,5-Dimethyl-pyrrol-1-yl)-pyridin-3-yl]-2-hydroxy-ethylamino}-propyl)-phenyl]-N-(3-phenyl-propyl)-acetamide (preparation 4) according to the method for example 1 to give the title compound as a pale yellow foam.

$^1$H NMR (400 MHz, CD$_3$OD): δ=7.79 (1H, s), 7.38 (1H, d), 7.24 (3H, m), 7.14 (5H, m), 7.01 (1H, d), 6.49 (1H, d), 4.51 (1H, m), 3.46 (2H, s), 3.20 (2H, t), 2.92-2.81 (2H, m), 2.68-2.55 (5H, m), 1.79 (2H, m), 1.06 (3H, d) ppm.

LRMS (APCl): m/z [M+H]$^+$ 447.

EXAMPLE 5

2-(3-{(2R)-2-[(2R)-2-(6-Amino-pyridin-3-yl)-2-hydroxy-ethylamino]-propyl}-phenyl)-N-phenethyl-acetamide

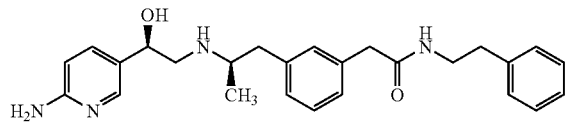

Prepared from 2-[3-((2R)-2-{(2R)-2-[6-(2,5-Dimethyl-pyrrol-1-yl)-pyridin-3-yl]-2-hydroxy-ethylamino}-propyl)-phenyl]-N-phenethyl-acetamide (preparation 5) according to the method for example 1 to give the title compound as a pale yellow foam.

$^1$H NMR (400 MHz, CD$_3$OD): δ=7.79 (1H, s), 7.38 (1H, d), 7.28-7.01 (9H, m), 6.49 (1H, d), 4.53 (1H, m), 3.42-3.37 (4H, m), 2.92-2.87 (2H, m), 2.77-2.73 (2H, m), 2.67-2.59 (3H, m), 1.08 (3H, d) ppm.

LRMS (APCl): m/z [M+H]$^+$ 433.

EXAMPLE 6

2-(3-{(2R)-2-[(2R)-2-(6-Amino-pyridin-3-yl)-2-hydroxy-ethylamino]-propyl}-phenyl)-N-(3,4-dimethyl-benzyl)-acetamide

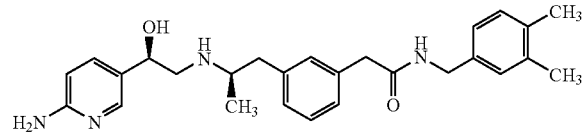

Prepared from N-(3,4-Dimethyl-benzyl)-2-[3-((2R)-2-{(2R)-2-[6-(2,5-dimethyl-pyrrol-1-yl)-pyridin-3-yl]-2-hydroxy-ethylamino}-propyl)-phenyl]-acetamide (preparation 6) according to the method for example 1 to give the title compound as a pale yellow foam.

$^1$H NMR (400 MHz, CD$_3$OD): δ=7.77 (1H, s), 7.35 (1H, d), 7.19-6.96 (7H, m), 6.50 (1H, d), 4.50 (1H, m), 4.27 (2H, s), 3.50 (2H, s), 2.89-2.81 (2H, m), 2.67-2.55 (3H, m), 2.18 (6H, s), 1.06 (3H, d) ppm.

LRMS (APCl): m/z [M+H]$^+$ 419.

EXAMPLE 7

2-(3-{(2R)-2-[(2R)-2-(6-Amino-pyridin-3-yl)-2-hydroxy-ethylamino]-propyl}-phenyl)-N-indan-2-yl-acetamide

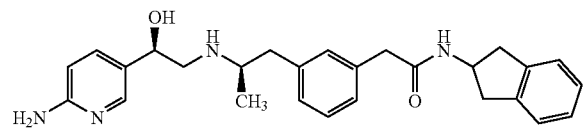

Prepared from 2-[3-((2R)-2-{(2R)-2-[6-(2,5-Dimethyl-pyrrol-1-yl)-pyridin-3-yl]-2-hydroxy-ethylamino}-propyl)-phenyl]-N-indan-2-yl-acetamide (preparation 7) according to the method for example 1 to give the title compound as a pale yellow foam.

$^1$H NMR (400 MHz, CD$_3$OD): δ=7.78 (1H, s), 7.37 (1H, d), 7.20-6.99 (8H, m), 6.51 (1H, s), 4.54 (2H, m), 3.43 (2H, s), 3.23 (2H, m), 2.89-2.79 (4H, m), 2.69-2.56 (3H, m), 1.07 (3H, d) ppm.

LRMS (APCl): m/z [M+H]$^+$ 444.

EXAMPLE 8

2-(3-{(2R)-2-[(2R)-2-(6-Amino-pyridin-3-yl)-2-hydroxy-ethylamino]-propyl}-phenyl)-N-(3,4-dichloro-benzyl)-acetamide

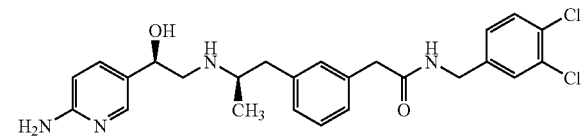

Prepared from N-(3,4-Dichloro-benzyl)-2-[3-(2R)-2-{(2R)-2-[6-(2,5-dimethyl-pyrrol-1-yl)-pyridin-3-yl]-2-hydroxy-ethylamino}-propyl)-phenyl]-acetamide (preparation 8) according to the method for example 1 to give the title compound as a pale yellow foam.

$^1$H NMR (400 MHz, CD$_3$OD): δ=7.78 (1H, s), 7.41-7.35 (3H, m), 7.22-7.02 (5H, m), 6.51 (1H, s), 4.50 (1H, m), 4.31 (2H, s), 3.52 (2H, s), 2.92-2.82 (2H, m), 2.70-2.56 (3H, m), 1.06 (3H, d) ppm.

LRMS (APCl): m/z [M+H]$^+$ 487/489.

EXAMPLE 9

2-(3-{2-[(2R)-2-(6-Amino-pyridin-3-yl)-2-hydroxy-ethylamino]-propyl}-phenyl)-N-(4-hydroxy-3-methoxy-benzyl)-acetamide

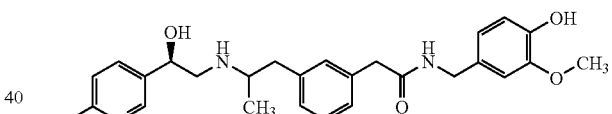

Prepared from 2-[3-(2-{(2R)-2-[6-(2,5-Dimethyl-pyrrol-1-yl)-pyridin-3-yl]-2-hydroxy-ethylamino}-propyl)-phenyl]-N-(4-hydroxy-3-methoxy-benzyl)-acetamide (preparation 9) according to the method for example 1 to give the title compound as a pale yellow foam.

$^1$H NMR (400 MHz, CD$_3$OD): δ=7.80 (1H, m), 7.39 (1H, m), 7.25-7.00 (4H, m), 6.77 (1H, bs), 6.69 (2H, m), 6.52 (1H, m), 4.55 (1H, m), 4.26 (2H, s), 3.73 (3H, s), 3.51 (2H, d), 2.90-2.58 (5H, m), 1.05 (3H, m) ppm.

LRMS (APCl): m/z [M+H]$^+$ 465, [M+Na]$^+$ 487, [M−H]$^−$ 463.

EXAMPLE 10

2-(4-{2-[(2R)-2-(6-Amino-pyridin-3-yl)-2-hydroxy-ethylamino]-2-methyl-propyl}-phenyl)-N-(3-methoxy-benzyl)-acetamide

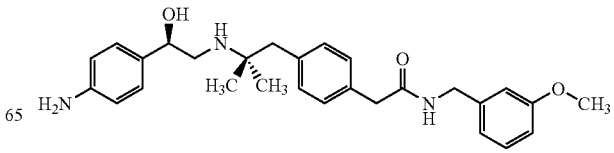

Prepared from 2-[4-(2-{(2R)-2-[6-(2,5-Dimethyl-pyrrol-1-yl)-pyridin-3-yl]-2-hydroxy-ethylamino}-2-methyl-propyl)-phenyl]-N-(3-methoxy-benzyl)-acetamide (preparation 10) according to the method for example 1 to give the title compound as a pale yellow foam.

¹H NMR (400 MHz, CD₃OD): δ=7.87 (1H, s), 7.47 (1H, d), 7.20 (3H, m), 7.11 (2H, d), 6.77 (3H, m), 6.55 (1H, d), 4.56 (1H, m), 4.33 (2H, s), 3.71 (3H, s), 3.52 (2H, s), 2.86 (1H, m), 2.70 (3H, m), 1.06 (3H, s), 1.05 (3H, s) ppm.

LRMS (APCI): m/z [M+H]⁺ 463.

EXAMPLE 11

2-(4-{2-[(2R)-2-(6-Amino-pyridin-3-yl)-2-hydroxy-ethylamino]-2-methyl-propyl}-phenyl)-N-(2,6-dimethoxy-benzyl)-acetamide

Prepared from N-(2,6-Dimethoxy-benzyl)-2-[4-(2-{(2R)-2-[6-(2,5-dimethyl-pyrrol-1-yl)-pyridin-3-yl]-2-hydroxy-ethylamino}-2-methyl-propyl)-phenyl]-acetamide (preparation 11) according to the method for example 1 to give the title compound as a pale yellow foam.

¹H NMR (400 MHz, CD₃OD): δ=7.86 (1H, s), 7.46 (1H, d), 7.28-7.08 (5H, m), 6.60 (2H, d), 6.54 (1H, d), 4.56 (1H, m), 4.42 (2H, s), 3.76 (6H, s), 3.45 (2H, s), 2.87 (1H, m), 2.70 (3H, m), 1.06 (3H, s), 1.05 (3H, s) ppm.

LRMS (APCI): m/z [M+H]⁺ 493.

EXAMPLE 12

2-(3-{2-[(2R)-2-(6-Amino-pyridin-3-yl)-2-hydroxy-ethylamino]-2-methyl-propyl}-phenyl)-N-(4-sulfamoyl-benzyl)-acetamide

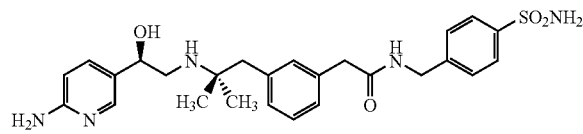

Prepared from 2-[3-(2-{(2R)-2-[6-(2,5-Dimethyl-pyrrol-1-yl)-pyridin-3-yl]-2-hydroxy-ethylamino}-2-methyl-propyl)-phenyl]-N-(4-sulfamoyl-benzyl)-acetamide (preparation 12) according to the method for example 1 to give the title compound as a pale yellow foam.

¹H NMR (400 MHz, CD₃OD): δ=7.85 (1H, s), 7.79 (2H, d), 7.48 (1H, d), 7.38 (2H, d), 7.25-7.10 (3H, m), 7.05 (1H, s), 6.58 (1H, d), 4.58 (1H, m), 4.40 (2H, s), 3.55 (2H, s), 2.82 (1H, m), 2.75-2.60 (3H, m), 1.05 (3H, s), 1.04 (3H, s) ppm.

LRMS (APCI): m/z [M+H]⁺ 512.

EXAMPLE 13

2-(3-{2-[(2R)-2-(6-Amino-pyridin-3-yl)-2-hydroxy-ethylamino]-2-methyl-propyl}-phenyl)-N-(2-ethoxy-benzyl)-acetamide

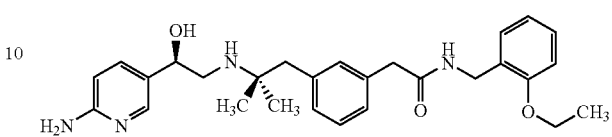

Prepared from 2-[3-(2-{(2R)-2-[6-(2,5-Dimethyl-pyrrol-1-yl)-pyridin-3-yl]-2-hydroxy-ethylamino}-2-methyl-propyl)-phenyl]-N-(2-ethoxy-benzyl)-acetamide (preparation 13) according to the method for example 1 to give the title compound as a pale yellow foam.

¹H NMR (400 MHz, CD₃OD): δ=7.87 (1H, s), 7.48 (1H, d), 7.21-7.04 (6H, m), 6.87 (1H, d), 6.83 (1H, t), 6.57 (1H, d), 4.57 (1H, m), 4.36 (2H, s), 4.01 (2H, q), 3.52 (2H, s), 2.88-2.83 (1H, m), 2.74-2.64 (3H, m), 1.32 (3H, t), 1.03 (3H, s), 1.02 (3H, s) ppm.

LRMS (APCI): m/z [M+H]⁺ 477.

EXAMPLE 14

2-(3-{2-[(2R)-2-(6-Amino-pyridin-3-yl)-2-hydroxy-ethylamino]-2-methyl-propyl}-phenyl)-N-indan-2-yl-acetamide

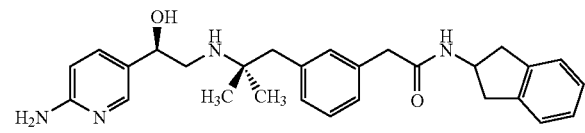

Prepared from 2-[3-(2-{(2R)-2-[6-(2,5-Dimethyl-pyrrol-1-yl)-pyridin-3-yl]-2-hydroxy-ethylamino}-2-methyl-propyl)-phenyl]-N-indan-2-yl-acetamide (preparation 14) according to the method for example 1 to give the title compound as a pale yellow foam.

¹H NMR (400 MHz, CD₃OD): δ=7.90 (1H, s), 7.48 (1H, d), 7.22-7.11 (7H, m), 7.04 (1H, d), 6.57 (1H, d), 4.56 (2H, m), 3.45 (2H, s), 3.24-3.20 (2H, m), 2.86-2.67 (6H, m), 1.07 (3H, s), 1.06 (3H, s) ppm.

LRMS (APCI): m/z [M+H]⁺ 459.

EXAMPLE 15

2-(3-{2-[(2R)-2-(6-Amino-pyridin-3-yl)-2-hydroxy-ethylamino]-2-methyl-propyl}-phenyl)-N-benzyl-acetamide

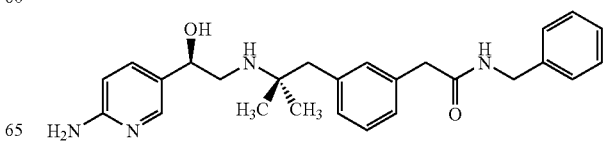

Prepared from N-Benzyl-2-[3-(2-{(2R)-2-[6-(2,5-dimethyl-pyrrol-1-yl)-pyridin-3-yl]-2-hydroxy-ethylamino}-2-methyl-propyl)-phenyl]-acetamide (preparation 15) according to the method for example 1 to give the title compound as a colourless foam.

$^1$H NMR (400 MHz, CD$_3$OD): δ=7.87 (1H, m), 7.48 (1H, dd), 7.28-7.13 (8H, m), 7.05 (1H, d), 6.57 (1H, d), 4.59-4.56 (1H, m), 4.36 (2H, s), 3.54 (2H, s), 2.90-2.85 (1H, m), 2.77-2.67 (3H, m), 1.08 (3H, s), 1.05 (3H, s) ppm.

LRMS (electrospray): m/z [M+H]$^+$ 433, [M+Na]$^+$ 455, [M–H]$^-$ 431.

EXAMPLE 16

2-(3-{2-[(2R)-2-(6-Amino-pyridin-3-yl)-2-hydroxy-ethylamino]-2-methyl-propyl}-phenyl)-N-phenethyl-acetamide

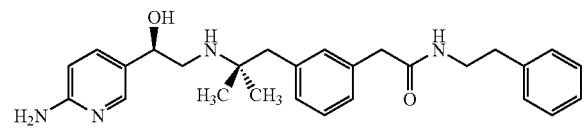

Prepared from 2-[3-(2-{(2R)-2-[6-(2,5-Dimethyl-pyrrol-1-yl)-pyridin-3-yl]-2-hydroxy-ethylamino}-2-methyl-propyl)-phenyl]-N-phenethyl-acetamide (preparation 16) according to the method for example 1 to give the title compound as a colourless foam.

$^1$H NMR (400 MHz, CD$_3$OD): δ=7.91-7.89 (1H, m), 7.51-7.49 (1H, m), 7.24-7.05 (9H, m), 6.58 (1H, d), 4.60-4.57 (1H, m), 3.44 (2H, s), 3.42-3.38 (2H, m), 2.90-2.85 (1H, m), 2.77-2.66 (6H, m), 1.08 (3H, s), 1.05 (3H, s) ppm.

LRMS (electrospray): m/z [M+H]$^+$ 447, [M+Na]$^+$ 469, [M–H]$^-$ 445.

EXAMPLE 17

2-(3-{2-[(2R)-2-(6-Amino-pyridin-3-yl)-2-hydroxy-ethylamino]-2-methyl-propyl}-phenyl)-N-(3-phenyl-propyl)-acetamide

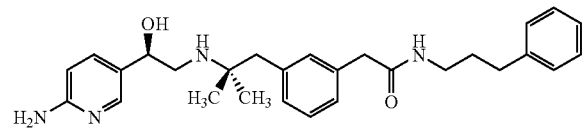

Prepared from 2-[3-(2-{(2R)-2-[6-(2,5-Dimethyl-pyrrol-1-yl)-pyridin-3-yl]-2-hydroxy-ethylamino}-2-methyl-propyl)-phenyl]-N-(3-phenyl-propyl)-acetamide (preparation 17) according to the method for example 1 to give the title compound as a colourless foam.

$^1$H NMR (400 MHz, CD$_3$OD): δ=7.88 (1H, s), 7.49-7.47 (1H, m), 7.24-7.11 (8H, m), 7.06-7.04 (1H, m), 6.56 (1H, d), 4.58-4.55 (1H, m), 3.47 (2H, s), 3.18 (2H, t), 2.88-2.83 (1H, m), 2.75-2.65 (3H, m), 2.59-2.55 (2H, m), 1.81-1.74 (2H, m), 1.06 (3H, s), 1.03 (3H, s) ppm.

LRMS (electrospray): m/z [M+H]$^+$ 461, [M+Na]$^+$ 483, [M–H]$^-$ 459.

EXAMPLE 18

2-(3-{2-[(2R)-2-(6-Amino-pyridin-3-yl)-2-hydroxy-ethylamino]-2-methyl-propyl}-phenyl)-N-(3,5-dichloro-benzyl)-acetamide

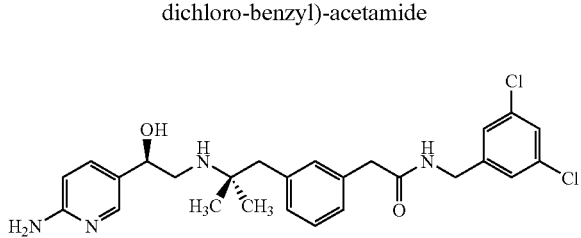

Prepared from N-(3,5-Dichloro-benzyl)-2-[3-(2-{(2R)-2-[6-(2,5-dimethyl-pyrrol-1-yl)-pyridin-3-yl]-2-hydroxy-ethylamino}-2-methyl-propyl)-phenyl]-acetamide (preparation 18) according to the method for example 1 to give the title compound as a colourless foam.

$^1$H NMR (400 MHz, CD$_3$OD): δ=7.87 (1H, s), 7.49-7.47 (1H, m), 7.26-7.12 (7H, m), 6.56 (1H, d), 4.59-4.56 (1H, m), 4.32 (2H, s), 3.55 (2H, s), 2.90-2.85 (2H, m), 2.77-2.66 (2H, m), 1.07 (3H, s), 1.04 (3H, s) ppm.

LRMS (electrospray): m/z [M+H]$^+$ 501/503, [M+Na]$^+$ 523/525, [M–H]$^-$ 499/501.

EXAMPLE 19

2-(3-{2-[(2R)-2-(6-Amino-pyridin-3-yl)-2-hydroxy-ethylamino]-2-methyl-propyl}-phenyl)-N-(3,4-dimethyl-benzyl)-acetamide

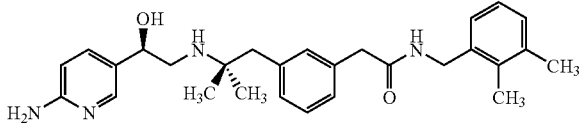

Prepared from N-(3,4-Dimethyl-benzyl)-2-[3-(2-{(2R)-2-[6-(2,5-dimethyl-pyrrol-1-yl)-pyridin-3-yl]-2-hydroxy-ethylamino}-2-methyl-propyl)-phenyl]-acetamide (preparation 19) according to the method for example 1 to give the title compound as a colourless foam.

$^1$H NMR (400 MHz, CD$_3$OD): δ=7.87 (1H, s), 7.49-7.47 (1H, m), 7.22-7.13 (3H, m), 7.05-6.95 (4H, m), 6.56 (1H, d), 4.58-4.55 (1H, m), 4.36 (2H, s), 3.51 (2H, s), 2.89-2.84 (1H, m), 2.75-2.65 (3H, m), 2.26 (3H, s), 2.14 (3H, s), 1.06 (3H, s), 1.04 (3H, s) ppm.

LRMS (electrospray): m/z [M+H]$^+$ 461, [M+Na]$^+$ 483, [M–H]$^-$ 459.

EXAMPLE 20

2-(3-{2-[(2R)-2-(6-Amino-pyridin-3-yl)-2-hydroxy-ethylamino]-2-methyl-propyl}-phenyl)-N-(3,4-dichloro-benzyl)-acetamide

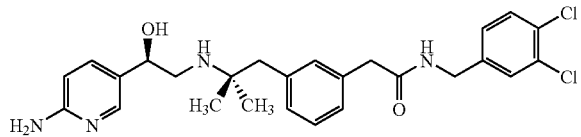

Prepared from N-(3,4-Dichloro-benzyl)-2-[3-(2-{(2R)-2-[6-(2,5-dimethyl-pyrrol-1-yl)-pyridin-3-yl]-2-hydroxy-ethylamino}-2-methyl-propyl)-phenyl]-acetamide (preparation 20) according to the method for example 1 to give the title compound as a colourless foam.

$^1$H NMR (400 MHz, CD$_3$OD): δ=7.88 (1H, s), 7.49-7.47 (1H, m), 7.39 (1H, d), 7.33 (1H, m), 7.24-7.11 (4H, m), 7.07-7.05 (1H, m), 6.56 (1H, d), 4.59-4.57 (1H, m), 4.32 (2H, s), 3.54 (2H, s), 2.90-2.85 (1H, m), 2.76-2.66 (3H, m), 1.06 (3H, s), 1.04 (3H, s) ppm.

LRMS (electrospray): m/z [M+H]$^+$ 501/503, [M+Na]$^+$ 523/525, [M−H]$^−$ 499/501.

EXAMPLES 21-27
(R AS DEFINED IN TABLE 1)

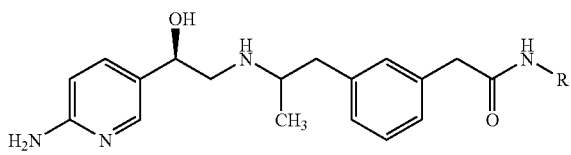

Prepared using the method for preparation 1 using the acid from preparation 30 and the appropriate amine to give amides, which were subjected to the conditions for example 1 without purification. Purification by HPLC:

Column: Phenomenex Luna C18, 10 um, 150×10 mm id, ambient temperature

Eluent A: 0.05% diethylamine in water Eluent B: Acetonitrile

Sample solvent: 90% dimethyl sulfoxide in water.

Gilson LC Pump Gradient Timetable Gilson 119 uv detector/Collect 225 (nm)

| Time | A % | B % | Flow (ml/min) |
| --- | --- | --- | --- |
| 0.00 | 80.0 | 20.0 | 6.000 |
| 0.20 | 80.0 | 20.0 | 6.000 |
| 7.00 | 5.0 | 95.0 | 6.000 |
| 9.00 | 5.0 | 95.0 | 6.000 |
| 9.10 | 80.0 | 20.0 | 6.000 |
| 10.50 | 80.0 | 20.0 | 6.000 |

Dual sensitivity 200/Peak sensitivity 60/Peak width 0.3 min. Gilson Autosampler Injection Vol(ul)-550.00 gave the title compounds.

TABLE 1

| Example | R | Retention time (min) | LRMS (electrospray) [M + H]$^+$ | [M − H]$^−$ |
| --- | --- | --- | --- | --- |
| 21 | 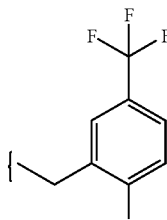 | 5.91 | 505 | 503 |
| 22 | 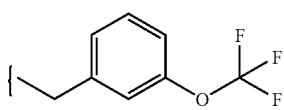 | 5.97 | 503 | 501 |
| 23 | 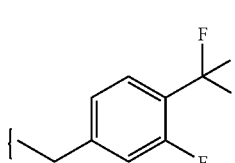 | 5.9 | 505 | 503 |
| 24 | 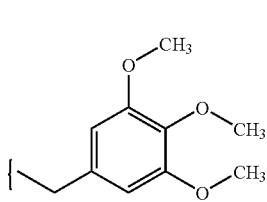 | 4.76 | 509 | 507 |

TABLE 1-continued

| Example | R | Retention time (min) | LRMS (electrospray) [M + H]⁺ | [M − H]⁻ |
|---|---|---|---|---|
| 25 | 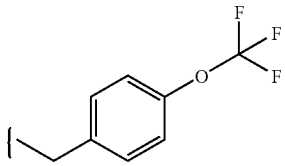 | 5.95 | 503 | 501 |
| 26 | 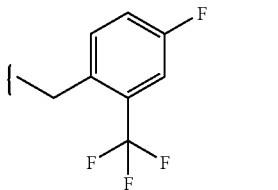 | 5.84 | 505 | 503 |
| 27 | 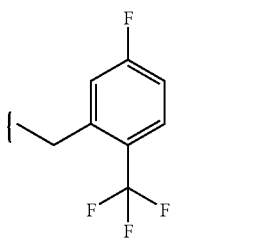 | 5.79 | 505 | 503 |

EXAMPLE 28

2-(3-{(2R)-2-[2-(6-Aminopyridin-3-yl)-2-hydroxy-ethylamino]-2-methylpropyl}phenyl)-N-(4'-hydroxy-biphenyl-3-ylmethyl)acetamide

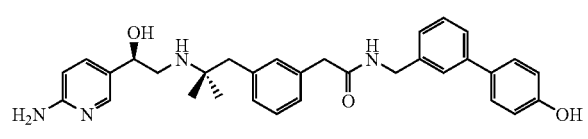

Prepared according to the method described for example 1 using the amide from preparation 48 to give the title compound as a light brown solid.

¹H NMR (400 MHz, CD₃OD): δ=7.86 (1H, m), 7.45 (1H, dd), 7.27-7.40 (5H, m), 7.17-7.24 (2H, m), 7.11-7.13 (2H, m), 7.03-7.05 (1H, m), 6.79-6.83 (2H, m), 6.54 (1H, d), 4.53 (1H, dd), 4.41 (2H, s), 3.54 (2H, s), 2.80 (1H, dd), 2.59-2.70 (3H, m), 1.01 (3H, s), 0.98 (3H, s) ppm.

LRMS (electrospray): m/z [M+H]⁺ 525, [M+Na]⁺ 547.

EXAMPLE 29

2-(3-{(2R)-2-[2-(6-Aminopyridin-3-yl)-2-hydroxy-ethylamino]-2-methylpropyl}phenyl)-N-(4'-hydroxy-biphenyl-4-ylmethyl)acetamide

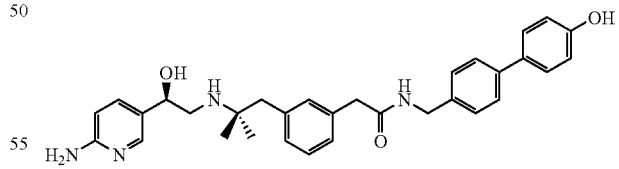

Prepared according to the method described for example 1 using the amide from preparation 49 to give the title compound as a pink foam.

¹H NMR (400 MHz, CD₃OD): δ=7.87 (1H, d), 7.39-7.48 (5H, m), 7.14-7.26 (5H, m), 7.05-7.07 (1H, m), 6.81-6.85 (2H, m), 6.55 (1H, d), 4.54 (1H, dd), 4.37 (2H, s), 3.54 (2H, s), 2.83-2.88 (1H, m), 2.65-2.76 (3H, m), 1.05 (3H, s), 1.02 (3H, s) ppm.

LRMS (electrospray): m/z [M+H]⁺ 525, [M+Na]⁺ 547.

EXAMPLE 30

2-(3-{(2R)-2-[(2R)-2-(6-Aminopyridin-3-yl)-2-hydroxyethylamino]propyl}phenyl)-N-(4'-hydroxybiphenyl-3-ylmethyl)acetamide

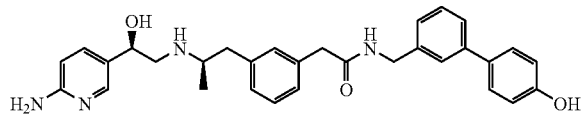

Prepared according to the method described for example 1 using the amide from preparation 50 to give the title compound as a colourless foam.

$^1$H NMR (400 MHz, CD$_3$OD): δ=7.76 (1H, d), 7.27-7.41 (6H, m), 7.09-7.22 (4H, m), 7.00-7.03 (1H, m), 6.79-6.83 (2H, m), 6.47 (1H, d), 4.48 (1H, dd), 4.40 (2H, s), 3.53 (2H, s), 2.79-2.88 (2H, m), 2.59 (2H, dd), 2.50-2.55 (1H, m), 1.00 (3H, d) ppm.

LRMS (electrospray): m/z [M+H]$^+$ 511, [M+Na]$^+$ 533.

EXAMPLE 31

2-(3-{(2R)-2-[(2R)-2-(6-Aminopyridin-3-yl)-2-hydroxyethylamino]propyl}phenyl)-N-(4-hydroxynaphthalen-1-ylmethyl)acetamide

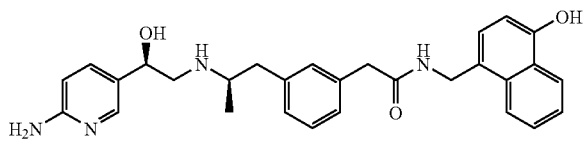

Prepared according to the method described for example 1 using the amide from preparation 57 to give the title compound as a light brown solid.

$^1$H NMR (400 MHz, CD$_3$OD): δ=8.17-8.20 (1H, m), 7.81-7.83 (1H, m), 7.71 (1H, d), 7.36-7.38 (2H, m), 7.7.28 (1H, dd), 7.18 (1H, d), 7.09-7.13 (2H, m), 6.92-6.94 (2H, m), 6.68 (1H, d), 6.43 (1H, d), 4.65 (2H, d), 4.44 (1H, dd), 3.43 (2H, s), 2.71-2.79 (2H, m), 2.53-2.58 (2H, m), 2.43-2.48 (1H, m), 0.95 (3H, d) ppm.

LRMS (APCl): m/z [M+H]$^+$ 485, [M+Na]$^+$ 507.

EXAMPLE 32

3-{2-[(2R)-2-(6-Aminopyridin-3-yl)-2-hydroxyethylamino]-2-methylpropyl}-N-(4'-hydroxybiphenyl-3-ylmethyl)benzamide

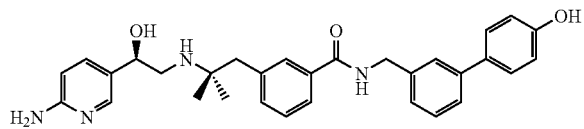

Prepared according to the method described for example 1 using the amide from preparation 52 to give the title compound as an off-white solid.

$^1$H NMR (400 MHz, CD$_3$OD): δ=7.86 (1H, d), 7.71-7.75 (2H, m), m 7.53 (1H, bs), 7.33-7.46 (7H, m), 7.25-7.27 (1H, d), 6.81-8.85 (2H, m), 6.49 (1H, d), 4.57 (1H, dd), 4.56 (2H, dd), 2.87-2.95 (2H, m), 2.69-2.74 (2H, m), 1.11 (3H, s), 1.05 (3H, s) ppm.

LRMS (APCl): m/z [M+H]$^+$ 511, [M+Na]$^+$ 533.

EXAMPLE 33

3-{(2R)-2-[2-(6-Amino-pyridin-3-yl)-2-hydroxyethylamino]-2-methyl-propyl}-N-[2-(4-hydroxyphenyl)-2-methyl-propyl]-benzamide

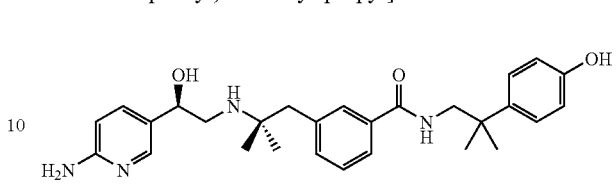

Prepared according to the method described for example 1 using the amide from preparation 53 to give the title compound as a light brown solid.

$^1$H NMR (400 MHz, CD$_3$OD): δ=7.87 (1H, d), 7.53-7.55 (1H, m), m 7.48-7.51 (2H, m), 7.32-7.33 (2H, m), 7.24 (2H, dd), 6.72 (2H, dd), 6.56 (1H, d), 4.55 (1H, dd), 3.51 (2H, s), 2.80-2.92 (2H, m), 2.70-2.74 (2H, m), 1.33 (6H, s), 1.08 (3H, s), 1.04 (3H, s) ppm.

LRMS (APCl): m/z [M+H]$^+$ 477.

EXAMPLE 34

3-{2-[(2R)-2-(6-Amino-pyridin-3-yl)-2-hydroxyethylamino]-2-methylpropyl}-N-[2-(4-hydroxy-2,5-dimethylphenyl)ethyl]benzamide

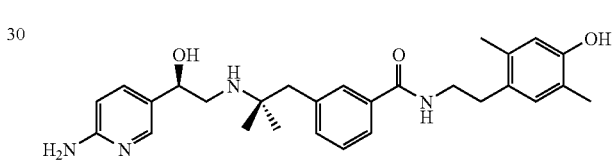

Prepared according to the method described for example 1 using the amide from preparation 54 to give the title compound as a colourless solid.

$^1$H NMR (400 MHz, CD$_3$OD): δ=7.89 (1H, d), 7.62-7.67 (2H, m), 7.83-7.89 (2H, m), 6.83 (1H, s), 6.57 (1H, d), 6.53 (1H, s), 4.57 (1H, dd), 3.44-3.48 (2H, m), 2.87-2.97 (2H, m), 2.70-2.80 (4H, m), 2.21 (3H, s), 2.08 (3H, s), 1.11 (3H, s), 1.04 (3H, s) ppm.

LRMS (APCl): m/z [M+H]$^+$ 477, [M−H]$^-$ 475.

EXAMPLE 35

3-{2-[(2R)-2-(6-Amino-pyridin-3-yl)-2-hydroxyethylamino]-2-methylpropyl}-N-[2-(4-hydroxy-2,3-dimethylphenyl)ethyl]benzamide

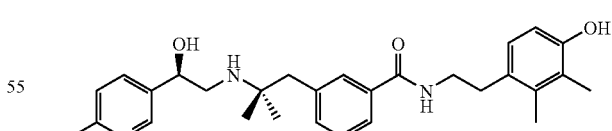

Prepared according to the method described for example 1 using the amide from preparation 55 to give the title compound as a colourless solid.

$^1$H NMR (400 MHz, CD$_3$OD): δ=1.05 (3H, s), 1.12 (3H, s), 21.12 (3H, s), 2.23 (3H, s), 270.275 (2H, m), 283-299 (4H, m), 2.45-2.48 (2H, m), 4.68-4.51 (1H, m), 6.53-6.59 (2h, m), 6.80 (1H, d), 7.33-7.41 (2H, m), 7.51 (1H, dd), 7.62-7.67 (2H, m), 7.90 (1H, d) ppm.

LRMS (electrospray): m/z [M+H]$^+$ 477, [M+Na]$^+$ 499.

EXAMPLE 36

3-{2-[(2R)-2-(6-Amino-pyridin-3-yl)-2-hydroxy-ethylamino]-2-methylpropyl}-N-[2-(4-hydroxy-2-methylphenyl)ethyl]benzamide

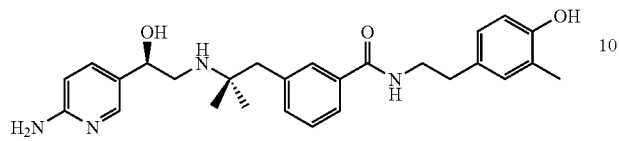

Prepared according to the method described for example 1 using the amide from preparation 56 to give the title compound as a beige coloured foam.

$^1$H NMR (400 MHz, CD$_3$OD): δ=1.06 (3H, s), 1.13 (3h, s), 2.14 (3H, s), 2.72-2.79 (4H, m), 2.87-2.98 (2H, m), 3.46-3.64 (2H, m), 4.69 (1H, dd), 6.57 (1H, d), 6.64 (1H, d), 6.85 (1H, dd), 6.93 (1H, d), 7.33-7.39 (2H, m), 7.60 (1H, dd), 7.61 (1H, bs), 7.63 (1H, dt), 7.89 (1H, d) ppm.

LRMS (APCl): m/z [M+H]$^+$ 463, [M−H]$^−$ 461.

EXAMPLE 37

3-{(2R)-2-[(2R)-2-(6-Aminopyridin-3-yl)-2-hydroxyethylamino]propyl}-N-[2-(4-hydroxy-2,5-dimethylphenyl)ethyl]benzamide

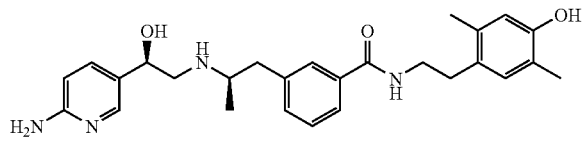

Prepared according to the method described for example 1 using the amide from preparation 57 to give the title compound as an off-white solid.

$^1$H NMR (400 MHz, CD$_3$OD): δ=7.80 (1H, d), 7.60-7.62 (1H, m), 7.57-7.58 (1H, m), 7.39 (1H, dd), 7.29-7.36 (2H, m), 6.55 (1H, s), 6.50 (1H, d), 4.54 (1H, dd), 3.46-3.50 (2H, m), 2.96 (1H, q), 2.78-2.90 (4H, m), 2.61-2.72 (2H, m), 2.24 (3H, s), 2.09 (3H, s), 1.07 (3H, d) ppm.

LRMS (APCl): m/z [M+H]$^+$ 463, [M−H]$^−$ 461.

EXAMPLE 38

3-{(2R)-2-[(2R)-2-(6-Aminopyridin-3-yl)-2-hydroxyethylamino]propyl}-N-[2-(4-hydroxy-2,3-dimethylphenyl)ethyl]benzamide

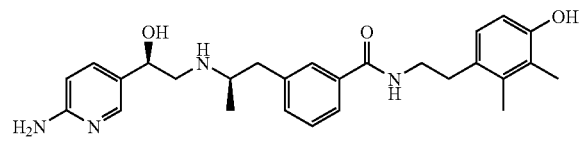

Prepared according to the method described for example 1 using the amide from preparation 58 to give the title compound as a pale pink foam.

$^1$H NMR (400 MHz, CD$_3$OD): δ=1.08 (3H, d), 2.13 (3H, s), 2.26 (3H, s), 2.61 (1H, dd), 2.70 (1H, dd), 2.79-2.81 (4H, m), 2.98 (1H, q), 3.46-3.49 (2H, s), 4.55 (1H, dd), 6.50 (1H, d), 6.54 (1H, d), 6.81 (1H, d), 7.29-7.86 (2H, m), 7.89 (1H, dd), 7.58 (1H, bs), 7.60 (1H, dt), 7.80 (1H, d) ppm.

LRMS (electrospray): m/z [M+H]$^+$ 463, [M+Na]$^+$ 485.

EXAMPLE 39

3-{(2R)-2-[(2R)-2-(6-Aminopyridin-3-yl)-2-hydroxyethylamino]propyl}-N-[2-(4-hydroxy-2-methylphenyl)ethyl]benzamide

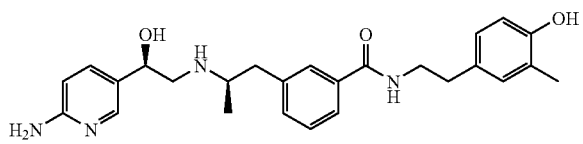

Prepared according to the method described for example 1 using the amide from preparation 59 to give the title compound as a beige coloured foam.

$^1$H NMR (400 MHz, CD$_3$OD): δ=1.08 (3H, d), 2.15 (6H, s), 2.62 (1H, dd), 2.70-2.92 (5H, m), 2.98 (1H, q), 3.51 (2H, t), 4.55 (1H, dd), 6.50 (1H, d), 6.65 (1H, d), 6.86 (1H, dd), 6.95 (1H, d), 7.28-7.36 (2H, m), 7.39 (1H, dd), 7.56 (1H, bs), 7.59 (1H, dt), 7.80 (1H, d) ppm.

LRMS (APCl): m/z [M+H]$^+$ 449, [M−H]$^−$ 447.

EXAMPLES 40 to 169 WERE PREPARED USING THE FOLLOWING PROCEDURE

The acid (150 μl of a 0.2 M solution) in anhydrous dimethylacetamide/3.75% triethylamine was added to each well of a 96 well polypropylene plate (2 ml volume per well). 225 μl of 0.2 M solutions of the amines in anhydrous dimethylacetamide/3.75% triethylamine were added to each well, followed by 225 μl of a freshly prepared 0.25 M solution of 2-(1H-benzotriazol-1-yl)-1,1,3,3-tetramethyluroniumhexafluorophosphate in dimethylacetamide was manually added to each well. The plates were sealed with a Teflon sheet and a rubber gasket and tightly clamped between two aluminium blocks and shaken and heated at 60° C. for 3 days, then the plate was opened and evaporated to dryness.

Methanol (200 μl) was added to each well and the plate re-sealed and shaken for 30 min until all residues were dissolved. The plates were re-opened and hydroxylamine hydrochloride (200 μl of a 1.0 M solution) in anhydrous ethanol was added manually to each well. The plate was sealed with a Teflon sheet and a rubber gasket and tightly clamped between two aluminium blocks and shaken and heated to 80° C. for 16 h, then evaporated to dryness.

Dimethylsulfoxide (300 μl) was added to each well and the plate sealed and shaken for 30 min until all residues were dissolved. The plate was opened, water (150 □l) was manually added and the plate sealed and manually shaken for 1 min.

Preparative reversed phase chromatography was performed on a Phenomenex Luna C18, 10 μm HPLC column (150×10 mm i.d.) at room temperature. The column flow rate was 8 ml/min. The mobile phase used was a binary acteonitrile/water buffered with 0.05% (v/v) diethylamine. Initial chromatographic conditions were set to 0% acetonitrile. Sample separation was achieved by increasing the acetonitrile concentration to 70% over 11.60 minutes with a hold of an additional 0.5 minutes before re-conditioning the column at 0% acetonitrile for a further 2.5 minutes. Fractions were collected by UV trigger based upon 225 nm and 254 nm wavelengths, the Dual sensitivity was set to 200, Peak sensitivity 30, and Peak width 0.3 min.

QC Analysis

All purified compounds were analysed by LC-MS analysis prior to registration. Two methods of detection were used, UV (DIAD) and ELSD.

Analytical reversed phase chromatography was performed on Phenomenex Luna C18, 5 um, HPLC column (30×4.6 mm id.) at room temperature using a Waters 1525 binary LC Pump. The column flow rate was 2.5 ml/min. The mobile phase used was a binary acteonitrile/water buffered with 0.05% (v/v) ammonium acetate. Initial chromatographic conditions were set to 5% acetonitrile. The gradient timetable was achieved by increasing the acetonitrile concentration to 95% over 3 minutes with a hold of an additional 0.5 minutes before re-conditioning the column at 5% acetonitrile for a further 1.0 minute. A Waters 2488 dual wavelength detector was used detecting dual wavelengths of 225 nm and 254 nm.

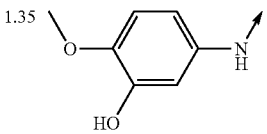

| Ex | Name | Mass | Detector | Rt | |
|----|------|------|----------|-----|---|
| 40 | 2-[3-(2-{[(2R)-2-(6-aminopyridin-3-yl)-2-hydroxyethyl]-amino}-2-methyl-propyl)phenyl]-N-(3-hydroxy-4-methoxy-phenyl)acetamide | 464.24 | ELSD | 1.35 | 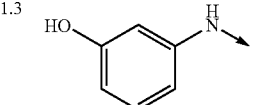 |
| 41 | 2-[3-(2-{[(2R)-2-(6-aminopyridin-3-yl)-2-hydroxyethyl]-amino}-2-methyl-propyl)phenyl]-N-(3-hydroxy-phenyl)acetamide | 434.23 | ELSD | 1.3 | 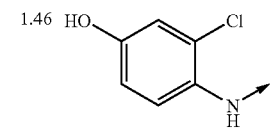 |
| 42 | 2-[3-(2-{[(2R)-2-(6-aminopyridin-3-yl)-2-hydroxyethyl]-amino}-2-methyl-propyl)phenyl]-N-(2-chloro-4-hydroxy-phenyl)acetamide | 468.19 | ELSD | 1.46 | 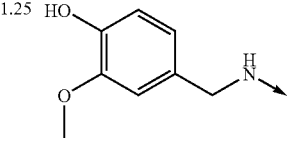 |
| 43 | 2-[3-(2-{[(2R)-2-(6-aminopyridin-3-yl)-2-hydroxyethyl]-amino}-2-methyl-propyl)phenyl]-N-(4-hydroxy-3-methoxy-benzyl)acetamide | 478.26 | ELSD | 1.25 | 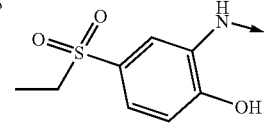 |
| 44 | 2-[3-(2-{[(2R)-2-(6-aminopyridin-3-yl)-2-hydroxyethyl]-amino}-2-methyl-propyl)phenyl]-N-[5-(ethylsulfonyl)-2-hydroxyphenyl]acetamide | 526.22 | ELSD | 1.25 | 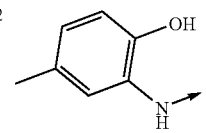 |
| 45 | 2-[3-(2-{[(2R)-2-(6-aminopyridin-3-yl)-2-hydroxyethyl]-amino}-2-methyl-propyl)phenyl]-N-(2-hydroxy-5-methyl-phenyl)acetamide | 448.25 | DAD: 225 | 1.52 | |

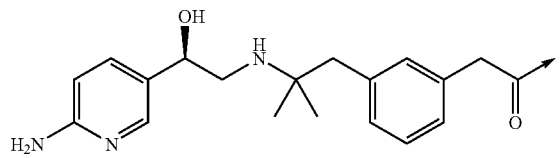

| Ex | Name | Mass | Detector | Rt | |
|---|---|---|---|---|---|
| 46 | 2-[3-(2-{[(2R)-2-(6-aminopyridin-3-yl)-2-hydroxyethyl]-amino}-2-methyl-propyl)phenyl]-N-(5-chloro-2-hydroxy-benzyl)acetamide | 482.21 | ELSD | 1.55 | 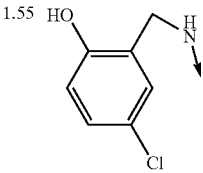 |
| 47 | 2-[3-(2-{[(2R)-2-(6-aminopyridin-3-yl)-2-hydroxyethyl]-amino}-2-methyl-propyl)phenyl]-N-(4-hydroxy-1,1'-biph-enyl-3-yl)acetamide | 510.26 | ELSD | 1.89 | 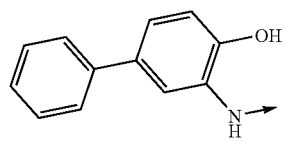 |
| 48 | 2-[3-(2-{[(2R)-2-(6-aminopyridin-3-yl)-2-hydroxyethyl]-amino}-2-methyl-propyl)phenyl]-N-[2-hydroxy-2-(3-hydroxyphenyl)ethyl]-N-methyl-acetamide | 492.27 | ELSD | 1.25 | 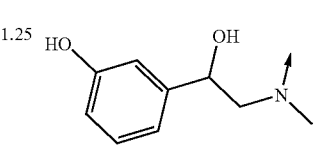 |
| 49 | 2-[3-(2-{[(2R)-2-(6-aminopyridin-3-yl)-2-hydroxyethyl]-amino}-2-methyl-propyl)phenyl]-N-ethyl-N-(3-hydroxy-phenyl)acetamide | 462.26 | DAD: 255 | 1.45 | 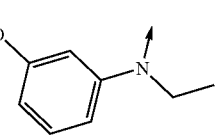 |
| 50 | 2-[3-(2-{[(2R)-2-(6-aminopyridin-3-yl)-2-hydroxyethyl]-amino}-2-methyl-propyl)phenyl]-N-[2-(3-ethoxy-4-hydroxyphenyl)ethyl]acetamide | 506.29 | ELSD | 1.4 | 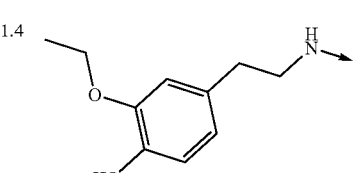 |
| 51 | 2-[3-(2-{[(2R)-2-(6-aminopyridin-3-yl)-2-hydroxyethyl] = amino}-2-methyl-propyl)phenyl]-N-{[4'-(hydroxymethyl)-1,1'-biphenyl-3-yl]methyl}acetamide | 538.29 | ELSD | 1.49 | 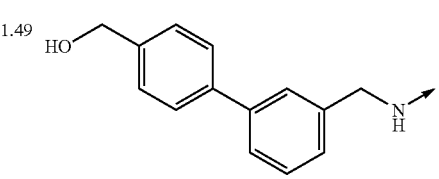 |
| 52 | 2-[3-(2-{[(2R)-2-(6-aminopyridin-3-yl)-2-hydroxyethyl]-amino}-2-methyl-propyl)phenyl]-N-(2,4-dichloro-6-hydroxybenzyl)acetamide | 516.17 | DAD: 255 | 1.9 | 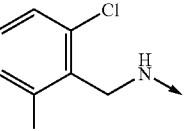 |

-continued

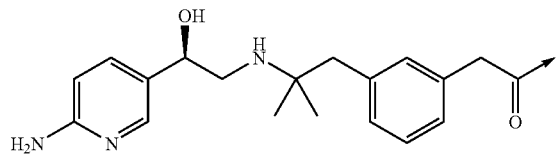

| Ex | Name | Mass | Detector | Rt | |
|---|---|---|---|---|---|
| 53 | 2-[3-(2-{[(2R)-2-(6-aminopyridin-3-yl)-2-hydroxyethyl]-amino}-2-methyl-propyl)phenyl]-N-[(3-fluoro-4'-hydroxy-1,1'-biphenyl-4-yl)methyl]acetamide | 542.27 | ELSD | 1.59 | |
| 54 | 2-[3-(2-{[(2R)-2-(6-aminopyridin-3-yl)-2-hydroxyethyl]-amino}-2-methyl-propyl)phenyl]-N-[(4'-hydroxy-3-methyl-1,1'-biphenyl-4-yl)methyl]acetamide | 538.29 | ELSD | 1.7 | |
| 55 | 2-[3-(2-{[(2R)-2-(6-aminopyridin-3-yl)-2-hydroxyethyl]-amino}-2-methyl-propyl)phenyl]-N-(2-chloro-5-hydroxy-benzyl)-N-ethylacetamide | 510.24 | DAD: 255 | 1.67 | |
| 56 | 2-[3-(2-{[(2R)-2-(6-aminopyridin-3-yl)-2-hydroxyethyl]-amino}-2-methyl-propyl)phenyl]-N-[(2'-hydroxy-1,1'-biphenyl-2-yl)methyl]acetamide | 524.28 | ELSD | 1.73 | |
| 57 | 2-[3-(2-{[(2R)-2-(6-aminopyridin-3-yl)-2-hydroxyethyl]-amino}-2-methyl-propyl)phenyl]-N-[3-hydroxy-5-(trifluoro-methyl)benzyl]-N-methylacetamide | 530.25 | ELSD | 1.77 | |
| 58 | 2-[3-(2-{[(2R)-2-(6-aminopyridin-3-yl)-2-hydroxyethyl]-amino}-2-methyl-propyl)phenyl]-N-(3-chloro-5-hydroxy-benzyl)-N-ethylacetamide | 510.24 | ELSD | 1.65 | |

-continued

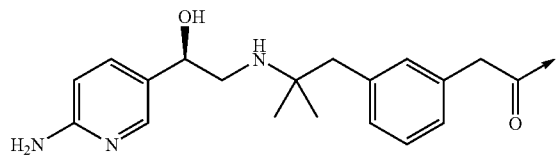

| Ex | Name | Mass | Detector | Rt |
|----|------|------|----------|-----|
| 59 | 2-[3-(2-{[(2R)-2-(6-aminopyridin-3-yl)-2-hydroxyethyl]-amino}-2-methyl-propyl)phenyl]-N-(3-chloro-5-hydroxy-benzyl)acetamide | 482.21 | ELSD | 1.52 |
| 60 | 2-[3-(2-{[(2R)-2-(6-aminopyridin-3-yl)-2-hydroxyethyl]-amino}-2-methyl-propyl)phenyl]-N-(4-hydroxy-3,5-dimethylbenzyl)acetamide | 476.28 | ELSD | 1.49 |
| 61 | 2-[3-(2-{[(2R)-2-(6-aminopyridin-3-yl)-2-hydroxyethyl]-amino}-2-methyl-propyl)phenyl]-N-[2-(2-hydroxyphen-yl)ethyl]acetamide | 462.26 | ELSD | 1.46 |
| 62 | 2-[3-(2-{[(2R)-2-(6-aminopyridin-3-yl)-2-hydroxyethyl]-amino}-2-methyl-benzyl-N-(4-hydroxyphenyl)acetamide | 524.3 | ELSD | 1.75 |
| 63 | 2-[3-(2-{[(2R)-2-(6-aminopyridin-3-yl)-2-hydroxyethyl]-amino}-2-methyl-propyl)phenyl]-N-[2-(4-hydroxyphenyl)-ethyl]acetamide | 462.3 | ELSD | 1.26 |
| 64 | 2-[3-(2-{[(2R)-2-(6-aminopyridin-3-yl)-2-hydroxyethyl]-amino}-2-methyl-propyl)phenyl]-N-(4-hydroxybenzyl)acetamide | 448.3 | ELSD | 1.33 |
| 65 | 2-[3-(2-{[(2R)-2-(6-aminopyridin-3-yl)-2-hydroxyethyl]-amino}-2-methyl-propyl)phenyl]-N-(2-hydroxybenzyl)acetamide | 448.3 | ELSD | 1.38 |

-continued

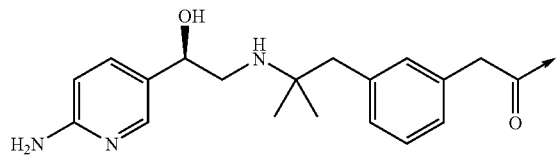

| Ex | Name | Mass | Detector | Rt | |
|---|---|---|---|---|---|
| 66 | 2-[3-(2-{[(2R)-2-(6-aminopyridin-3-yl)-2-hydroxyethyl]-amino}-2-methyl-propyl)phenyl]-N-(3-hydroxybenzyl)acetamide | 448.3 | ELSD | 1.33 | |
| 67 | 2-[3-(2-{[(2R)-2-(6-aminopyridin-3-yl)-2-hydroxyethyl]-amino}-2-methyl-propyl)phenyl]-N-[2-(3-hydroxyphenyl)-ethyl]acetamide | 462.3 | ELSD | 1.41 | |
| 68 | 2-[3-(2-{[(2R)-2-(6-aminopyridin-3-yl)-2-hydroxyethyl]-amino}-2-methyl-propyl)phenyl]-N-[2-(4-hydroxy-3-methoxyphenyl)ethyl]acetamide | 492.3 | ELSD | 1.29 | |
| 69 | methyl 4-({[3-(2-{[(2R)-2-(6-aminopyridin-3-yl)-2-hydroxyethyl]-amino}-2-methyl-propyl)phenyl]acetyl}amino)-3-hydroxybenzoate | 492.2 | ELSD | 1.57 | |
| 70 | 2-[3-(2-{[(2R)-2-(6-aminopyridin-3-yl)-2-hydroxyethyl]-amino}-2-methyl-propyl)phenyl]-N-(5-tert-butyl-2-hydroxyphenyl)acetamide | 490.3 | ELSD | 1.85 | |
| 71 | 2-[3-(2-{[(2R)-2-(6-aminopyridin-3-yl)-2-hydroxyethyl]-amino}-2-methyl-propyl)phenyl]-N-(3-hydroxy-4-methylphenyl)acetamide | 448.3 | ELSD | 1.54 | |

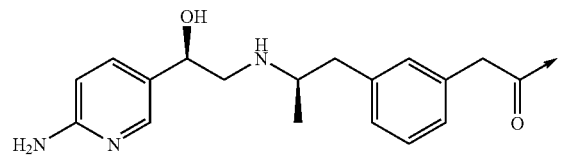

| Ex | Name | Mass | Detector | Rt | |
|---|---|---|---|---|---|
| 72 | 2-[3-((2R)-2-{[(2R)-2-(6-aminopyridin-3-yl)-2-hydroxyethyl]amino}propyl)phenyl]-N-[2-(4-hydroxyphenyl)ethyl]acetamide | 448.25 | ELSD | 1.3 | |
| 73 | 2-[3-((2R)-2-{[(2R)-2-(6-aminopyridin-3-yl)-2-hydroxy-ethyl]amino}propyl)phenyl]-N-(4-hydroxybenzyl)acetamide | 434.23 | ELSD | 1.16 | |
| 74 | 2-[3-((2R)-2-{[(2R)-2-(6-aminopyridin-3-yl)-2-hydroxy-ethyl]amino}propyl)phenyl]-N-(2-hydroxybenzyl)acetamide | 434.23 | DAD: 225 | 1.35 | |
| 75 | 2-[3-((2R)-2-{[(2R)-2-(6-aminopyridin-3-yl)-2-hydroxy-ethyl]amino}propyl)phenyl]-N-(3-hydroxybenzyl)acetamide | 434.23 | ELSD | 1.23 | |
| 43 | 2-[3-((2R)-2-{[(2R)-2-(6-aminopyridin-3-yl)-2-hydroxy-ethyl]amino}propyl)phenyl]-N-[2-(3-hydroxyphenyl)ethyl]acetamide | 448.25 | ELSD | 1.34 | |
| 77 | 2-[3-((2R)-2-{[(2R)-2-(6-aminopyridin-3-yl)-2-hydroxy-ethyl]amino}propyl)phenyl]-N-[2-(4-hydroxy-3-methoxyphenyl)ethyl]acetamide | 478.26 | ELSD | 1.24 | |
| 78 | 2-[3-((2R)-2-{[(2R)-2-(6-aminopyridin-3-yl)-2-hydroxy-ethyl]amino}propyl)phenyl]-N-(5-tert-butyl-2-hydroxy-phenyl)acetamide | 476.28 | ELSD | 1.82 | |
| 79 | 2-[3-((2R)-2-{[(2R)-2-(6-aminopyridin-3-yl)-2-hydroxy-ethyl]amino}propyl)phenyl]-N-(3-hydroxy-4-methyl-phenyl)acetamide | 434.23 | DAD: 255 | 1.52 | |

-continued

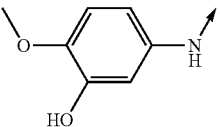

| Ex | Name | Mass | Detector | Rt | |
|---|---|---|---|---|---|
| 80 | 2-[3-((2R)-2-{[(2R)-2-(6-aminopyridin-3-yl)-2-hydroxy-ethyl]amino}propyl)phenyl]-N-(3-hydroxy-4-methoxy-phenyl)acetamide | 450.23 | ELSD | 1.25 | 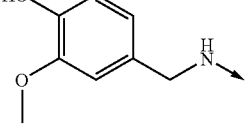 |
| 81 | 2-[3-((2R)-2-{[(2R)-2-(6-aminopyridin-3-yl)-2-hydroxy-ethyl]amino}propyl)phenyl]-N-(4-hydroxy-3-methoxy-benzyl)acetamide | 464.24 | ELSD | 1.3 | 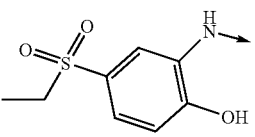 |
| 82 | 2-[3-((2R)-2-{[(2R)-2-(6-aminopyridin-3-yl)-2-hydroxy-ethyl]amino}propyl)phenyl]-N-[5-(ethylsulfonyl)-2-hydroxyphenyl]acetamide | 512.21 | ELSD | 1.22 | 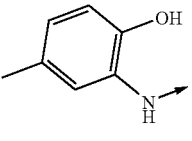 |
| 83 | 2-[3-((2R)-2-{[(2R)-2-(6-aminopyridin-3-yl)-2-hydroxy-ethyl]amino}propyl)phenyl]-N-(2-hydroxy-5-methyl-phenyl)acetamide | 434.23 | ELSD | 1.47 | 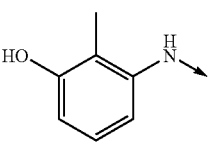 |
| 84 | 2-[3-((2R)-2-{[(2R)-2-(6-aminopyridin-3-yl)-2-hydroxy-ethyl]amino}propyl)phenyl]-N-(3-hydroxy-2-methyl-phenyl)acetamide | 434.23 | DAD: 225 | 1.24 | 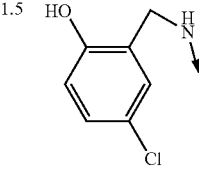 |
| 85 | 2-[3-((2R)-2-{[(2R)-2-(6-aminopyridin-3-yl)-2-hydroxy-ethyl]amino}propyl)phenyl]-N-(5-chloro-2-hydroxybenzyl)-acetamide | 468.19 | ELSD | 1.5 | 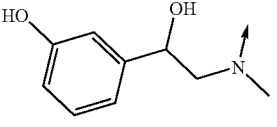 |
| 86 | 2-[3-((2R)-2-{[(2R)-2-(6-aminopyridin-3-yl)-2-hydroxy-ethyl]amino}propyl)phenyl]-N-[2-hydroxy-2-(3-hydroxyphenyl)ethyl]-N-methyl-acetamide | 478.26 | ELSD | 1.26 | 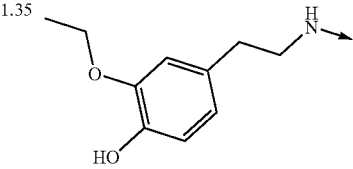 |
| 87 | 2-[3-((2R)-2-{[(2R)-2-(6-aminopyridin-3-yl)-2-hydroxy-ethyl]amino}propyl)phenyl]-N-[2-(3-ethoxy-4-hydroxy-phenyl)ethyl]acetamide | 492.27 | DAD: 225 | 1.35 |  |

-continued

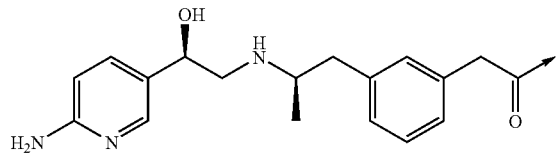

| Ex | Name | Mass | Detector | Rt |
|---|---|---|---|---|
| 88 | 2-[3-((2R)-2-{[(2R)-2-(6-aminopyridin-3-yl)-2-hydroxy-ethyl]amino}propyl)phenyl]-N-[2-(3-hydroxy-4-methoxy-phenyl)ethyl]acetamide | 478.26 | ELSD | 1.29 |
| 89 | 2-[3-((2R)-2-{[(2R)-2-(6-aminopyridin-3-yl)-2-hydroxy-ethyl]amino}propyl)phenyl]-N-ethyl-N-[2-(4-hydroxyphenyl)ethyl]acetamide | 476.28 | ELSD | 1.52 |
| 90 | 2-[3-((2R)-2-{[(2R)-2-(6-aminopyridin-3-yl)-2-hydroxy-ethyl]amino}propyl)phenyl]-N-(2-chloro-4-hydroxybenzyl)-N-ethylacetamide | 496.22 | ELSD | 1.56 |
| 91 | 2-[3-((2R)-2-{[(2R)-2-(6-aminopyridin-3-yl)-2-hydroxy-ethyl]amino}propyl)phenyl]-N-(5-hydroxy-1,2,3,4-tetrahydronaphthalen-1-yl)acetamide | 474.26 | ELSD | 1.36 |
| 92 | 2-[3-((2R)-2-{[(2R)-2-(6-aminopyridin-3-yl)-2-hydroxy-ethyl]amino}propyl)phenyl]-N-(4-hydroxyphenyl)acetamide | 420.22 | ELSD | 1.19 |
| 93 | 2-[3-((2R)-2-{[(2R)-2-(6-aminopyridin-3-yl)-2-hydroxy-ethyl]amino}propyl)phenyl]-N-[4-(4-hydroxyphenyl)butyl]acetamide | 476.28 | DAD: 255 | 1.42 |

-continued

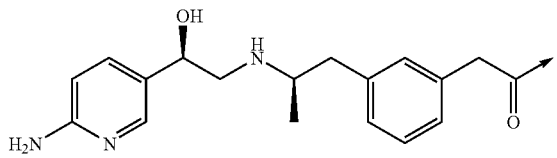

| Ex | Name | Mass | Detector | Rt |
|---|---|---|---|---|
| 94 | 2-[3-((2R)-2-{[(2R)-2-(6-aminopyridin-3-yl)-2-hydroxy-ethyl]amino}propyl)phenyl]-N-[(4'-hydroxy-1,1'-phenyl-4-yl)methyl]acetamide | 510.26 | ELSD | 1.51 |
| 95 | 2-[3-((2R)-2-{[(2R)-2-(6-aminopyridin-3-yl)-2-hydroxy-ethyl]amino}propyl)phenyl]-N-{[4'-(hydroxymethyl)-1,1'-biphenyl-3-yl]methyl}acetamide | 524.28 | ELSD | 1.53 |
| 96 | 2-[3-((2R)-2-{[(2R)-2-(6-aminopyridin-3-yl)-2-hydroxy-ethyl]amino}propyl)phenyl]-N-(2,4-dichloro-6-hydroxy-benzyl)acetamide | 502.15 | ELSD | 1.74 |
| 97 | 2-[3-((2R)-2-{[(2R)-2-(6-aminopyridin-3-yl)-2-hydroxy-ethyl]amino}propyl)phenyl]-N-[(3-fluoro-4'-hydroxy-1,1'-biphenyl-4-yl)methyl]acetamide | 528.25 | ELSD | 1.64 |
| 98 | 2-[3-((2R)-2-{[(2R)-2-(6-aminopyridin-3-yl)-2-hydroxy-ethyl]amino}propyl)phenyl]-N-[(4'-hydroxy-3-methyl-1,1'-biphenyl-4-yl)methyl]acetamide | 524.28 | ELSD | 1.59 |
| 99 | 2-[3-((2R)-2-{[(2R)-2-(6-aminopyridin-3-yl)-2-hydroxy-ethyl]amino}propyl)phenyl]-N-(2-chloro-5-hydroxybenzyl)-N-ethylacetamide | 496.22 | ELSD | 1.7 |

-continued

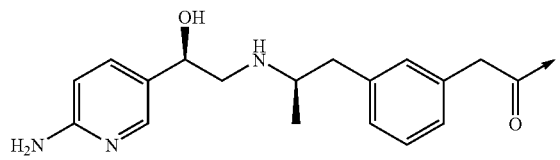

| Ex | Name | Mass | Detector | Rt | |
|---|---|---|---|---|---|
| 100 | 2-[3-((2R)-2-{[(2R)-2-(6-aminopyridin-3-yl)-2-hydroxy-ethyl]amino}propyl)phenyl]-N-(2'-hydroxy-1,1'-biphenyl-2-yl)methyl]acetamide | 510.26 | ELSD | 1.61 | |
| 101 | 2-[3-((2R)-2-{[(2R)-2-(6-aminopyridin-3-yl)-2-hydroxy-ethyl]amino}propyl)phenyl]-N-[3-hydroxy-5-(trifluoromethyl)benzyl]-N-methylacetamide | 516.23 | ELSD | 1.69 | |
| 102 | 2-[3-((2R)-2-{[(2R)-2-(6-aminopyridin-3-yl)-2-hydroxy-ethyl]amino}propyl)phenyl]-N-(3-chloro-5-hydroxybenzyl)-N-ethylacetamide | 496.22 | ELSD | 1.6 | |
| 103 | 2-[3-((2R)-2-{[(2R)-2-(6-aminopyridin-3-yl)-2-hydroxy-ethyl]amino}propyl)phenyl]-N-(3-chloro-5-hydroxy-benzyl)acetamide | 468.2 | ELSD | 1.4 | |
| 104 | 2-[3-((2R)-2-{[(2R)-2-(6-aminopyridin-3-yl)-2-hydroxy-ethyl]amino}propyl)phenyl]-N-(4-hydroxy-3,5-dimethylbenzyl)acetamide | 462.3 | ELSD | 1.35 | |
| 105 | 2-[3-((2R)-2-{[(2R)-2-(6-aminopyridin-3-yl)-2-hydroxy-ethyl]amino}propyl)phenyl]-N-(3,5-dichloro-2-hydroxy-benzyl)acetamide | 502.2 | ELSD | 1.76 | |

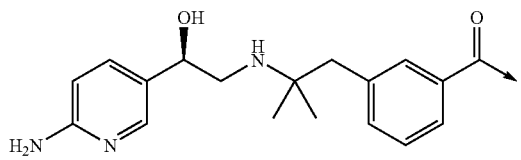

| Ex | Name | Mass | Detector | Rt | |
|----|------|------|----------|-----|---|
| 106 | 3-(2-{[(2R)-2-(6-aminopyridin-3-yl)-2-hydroxyethyl]-amino}-2-methyl-propyl)-N-[2-(4-hydroxyphenyl)ethyl]benzamide | 448.25 | ELSD | 1.26 | |
| 107 | 3-(2-{[(2R)-2-(6-aminopyridin-3-yl)-2-hydroxyethyl]-amino}-2-methyl-propyl)-N-(4-hydroxybenzyl)benzamide | 434.23 | ELSD | 1.34 | |
| 108 | 3-(2-{[(2R)-2-(6-aminopyridin-3-yl)-2-hydroxyethyl]-amino}-2-methyl-propyl)-N-(2-hydroxybenzyl)benzamide | 434.23 | ELSD | 1.43 | |
| 109 | 3-(2-{[(2R)-2-(6-aminopyridin-3-yl)-2-hydroxyethyl]-amino}-2-methyl-propyl)-N-[2-(3-hydroxyphenyl)ethyl]benzamide | 448.25 | ELSD | 1.32 | |
| 110 | 3-(2-{[(2R)-2-(6-aminopyridin-3-yl)-2-hydroxyethyl]-amino}-2-methyl-propyl)-N-[2-(4-hydroxy-3-methoxyphenyl)ethyl]benzamide | 478.26 | ELSD | 1.4 | |
| 111 | 3-(2-{[(2R)-2-(6-aminopyridin-3-yl)-2-hydroxyethyl]-amino}-2-methyl-propyl)-N-(3-hydroxy-4-methyl-phenyl)benzamide | 434.23 | ELSD | 1.44 | |
| 112 | 3-(2-{[(2R)-2-(6-aminopyridin-3-yl)-2-hydroxyethyl]-amino}-2-methyl-propyl)-N-[2-(4-hydroxy-3,5-dimethoxyphenyl)ethyl]benzamide | 508.27 | ELSD | 1.34 | |
| 113 | 3-(2-{[(2R)-2-(6-aminopyridin-3-yl)-2-hydroxyethyl]-amino}-2-methyl-propyl)-N-(3-hydroxy-4-methoxyphenyl)benzamide | 450.23 | ELSD | 1.27 | |

-continued

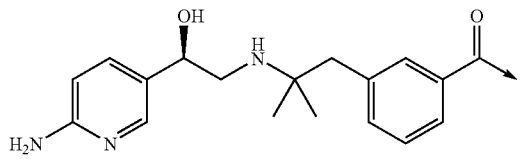

| Ex | Name | Mass | Detector | Rt | |
|---|---|---|---|---|---|
| 114 | 3-(2-{[(2R)-2-(6-aminopyridin-3-yl)-2-hydroxyethyl]-amino}-2-methyl-propyl)-N-(3-hydroxyphenyl)benzamide | 420.22 | ELSD | 1.4 | |
| 115 | 3-(2-{[(2R)-2-(6-aminopyridin-3-yl)-2-hydroxyethyl]-amino}-2-methyl-propyl)-N-(4-hydroxy-3-methoxybenzyl)benzamide | 464.24 | ELSD | 1.25 | |
| 116 | 3-(2-{[(2R)-2-(6-aminopyridin-3-yl)-2-hydroxyethyl]-amino}-2-methyl-propyl)-N-[5-(ethylsulfonyl)-2-hydroxyphenyl]benzamide | 512.21 | ELSD | 1.24 | |
| 117 | 3-(2-{[(2R)-2-(6-aminopyridin-3-yl)-2-hydroxyethyl]-amino}-2-methyl-propyl)-N-(3-hydroxy-2-methyl-phenyl)benzamide | 434.23 | ELSD | 1.26 | |
| 118 | 3-(2-{[(2R)-2-(6-aminopyridin-3-yl)-2-hydroxyethyl]-amino}-2-methyl-propyl)-N-(5-chloro-2-hydroxy-benzyl)benzamide | 468.19 | ELSD | 1.69 | |
| 119 | 3-(2-{[(2R)-2-(6-aminopyridin-3-yl)-2-hydroxyethyl]-amino}-2-methyl-propyl)-N-(4-hydroxy-1,1'-biphenyl-3-yl)benzamide | 496.25 | ELSD | 1.84 | |
| 120 | 3-(2-{[(2R)-2-(6-aminopyridin-3-yl)-2-hydroxyethyl]-amino}-2-methyl-propyl)-N-[2-hydroxy-2-(3-hydroxyphenyl)ethyl]-N-methylbenzamide | 478.26 | ELSD | 1.29 | |

-continued

| Ex | Name | Mass | Detector | Rt | |
|----|------|------|----------|-----|---|
| 121 | 3-(2-{[(2R)-2-(6-aminopyridin-3-yl)-2-hydroxyethyl]-amino}-2-methyl-propyl)-N-(2-hydroxybenzyl)-N-methylbenzamide | 448.25 | ELSD | 1.43 | 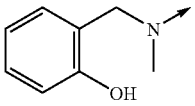 |
| 122 | 3-(2-{[(2R)-2-(6-aminopyridin-3-yl)-2-hydroxyethyl]-amino}-2-methyl-propyl)-N-(3,5-dichloro-2-hydroxybenzyl)benzamide | 502.15 | DAD: 225 | 1.82 | 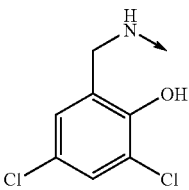 |
| 123 | 3-(2-{[(2R)-2-(6-aminopyridin-3-yl)-2-hydroxyethyl]-amino}-2-methyl-propyl)-N-[2-(2-hydroxyphenyl)ethyl]benzamide | 448.25 | ELSD | 1.41 | 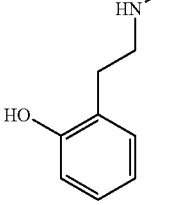 |
| 124 | 3-(2-{[(2R)-2-(6-aminopyridin-3-yl)-2-hydroxyethyl]-amino}-2-methyl-propyl)-N-[2-(3-ethoxy-4-hydroxyphenyl)ethyl]benzamide | 492.27 | ELSD | 1.34 | 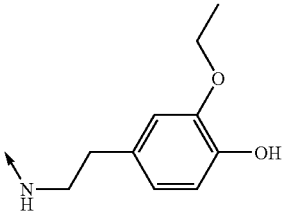 |
| 125 | 3-(2-{[(2R)-2-(6-aminopyridin-3-yl)-2-hydroxyethyl]-amino}-2-methyl-propyl)-N-[2-(3-hydroxy-4-methoxyphenyl)ethyl]benzamide | 478.26 | ELSD | 1.09 | 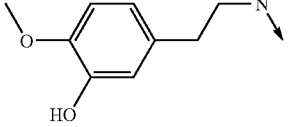 |
| 126 | 2-[3-(2-{[(2R)-2-(6-aminopyridin-3-yl)-2-hydroxyethyl]-amino}-2-methyl-propyl)-benzoyl]-2,3,4,5-tetrahydro-1H-2-benzazepin-8-ol | 474.26 | ELSD | 1.28 | 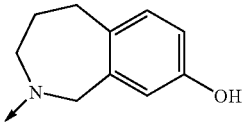 |
| 127 | 3-(2-{[(2R)-2-(6-aminopyridin-3-yl)-2-hydroxyethyl]-amino}-2-methyl-propyl)-N-[(4'-hydroxy-3-methyl-1,1'-biphenyl-4-yl)methyl]-benzamide | 524.28 | ELSD | 1.48 | 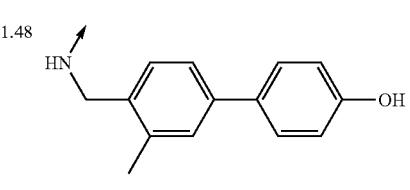 |

-continued

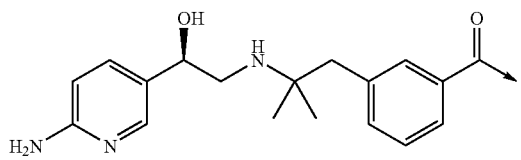

| Ex | Name | Mass | Detector | Rt | |
|---|---|---|---|---|---|
| 128 | 3-(2-{[(2R)-2-(6-aminopyridin-3-yl)-2-hydroxyethyl]-amino}-2-methyl-propyl)-N-[(3'hydroxy-1,1'-biphenyl-2-yl)-methyl]benzamide | 510.26 | ELSD | 1.25 | 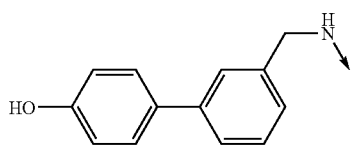 |

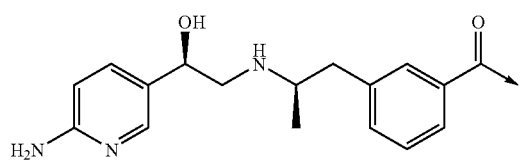

| Ex | Name | Mass | Detector | Rt | |
|---|---|---|---|---|---|
| 129 | 3-((2R)-2-{[(2R)-2-(6-aminopyridin-3-yl)-2-hydroxyethyl]-amino}propyl)-N-(5-chloro-2-hydroxy-benzyl)benzamide | 454.2 | ELSD | 1.63 | 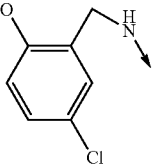 |
| 130 | 3-((2R)-2-{[(2R)-2-(6-aminopyridin-3-yl)-2-hydroxyethyl]-amino}propyl)-N-[2-hydroxy-2-(3-hydroxyphenyl)ethyl]-N-methylbenzamide | 464.2 | ELSD | 1.25 | 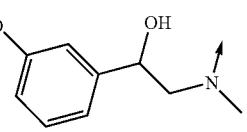 |
| 131 | 3-((2R)-2-{[(2R)-2-(6-aminopyridin-3-yl)-2-hydroxyethyl]-amino}propyl)-N-(2-hydroxybenzyl)-N-methylbenzamide | 434.2 | ELSD | 1.4 | 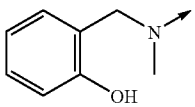 |
| 132 | 3-((2R)-2-{[(2R)-2-(6-aminopyridin-3-yl)-2-hydroxyethyl]-amino}propyl)-N-[2-(3-ethoxy-4-hydroxyphenyl)ethyl] benzamide | 478.3 | ELSD | 1.36 | 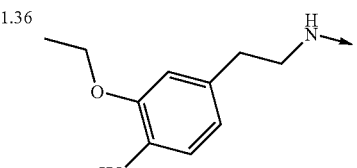 |
| 133 | 3-((2R)-2-{[(2R)-2-(6-aminopyridin-3-yl)-2-hydroxyethyl]-amino}propyl)-N-[2-(3-hydroxy-4-methoxyphenyl)ethyl] benzamide | 464.2 | ELSD | 1.39 | 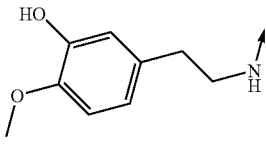 |

-continued

| Ex | Name | Mass | Detector | Rt | |
|---|---|---|---|---|---|
| 134 | 2-[3-((2R)-2-{[(2R)-2-(6-aminopyridin-3-yl)-2-hydroxyethyl]-amino}propyl)benzoyl]-2,3,4,5-tetrahydro-1H-2-benzazepin-8-ol | 460.3 | ELSD | 1.39 | |
| 135 | 3-((2R)-2-{[(2R)-2-(6-aminopyridin-3-yl)-2-hydroxyethyl]-amino}propyl)-N-ethyl-N-[2-(4-hydroxyphenyl)ethyl]benzamide | 462.3 | ELSD | 1.45 | |
| 136 | 3-((2R)-2-{[(2R)-2-(6-aminopyridin-3-yl)-2-hydroxyethyl]-amino}propyl)-N-(2-chloro-4-hydroxy-benzyl)-N-ethylbenzamide | 482.2 | ELSD | 1.49 | |
| 137 | 3-((2R)-2-{[(2R)-2-(6-aminopyridin-3-yl)-2-hydroxyethyl]-amino}propyl)-N-(5-hydroxy-1,2,3,4-tetrahydronaphthalen-1-yl)benzamide | 460.3 | ELSD | 1.48 | |
| 138 | 2-{4-[3-((2R)-2-{[(2R)-2-(6-amino-pyridin-3-yl)-2-hydroxyethyl]amino}propyl)benzoyl]piperazin-1-yl}phenol | 475.3 | ELSD | 1.46 | |
| 139 | 3-((2R)-2-{[(2R)-2-(6-aminopyridin-3-yl)-2-hydroxyethyl]-amino}propyl)-N-(4-hydroxyphenyl)benzamide | 406.2 | ELSD | 1.24 | |
| 140 | 3-((2R)-2-{[(2R)-2-(6-aminopyridin-3-yl)-2-hydroxyethyl]-amino}propyl)-N-[4-(4-hydroxyphenyl)butyl]benzamide | 462.3 | ELSD | 1.44 | |

-continued

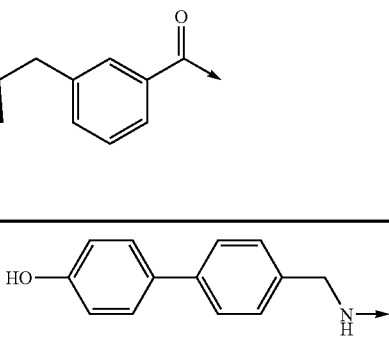

| Ex | Name | Mass | Detector | Rt | |
|---|---|---|---|---|---|
| 141 | 3-((2R)-2-{[(2R)-2-(6-aminopyridin-3-yl)-2-hydroxyethyl]-amino}propyl)-N-[(4'-hydroxy-1,1'-biphenyl-4-yl)methyl]benzamide | 496.3 | ELSD | 1.54 | 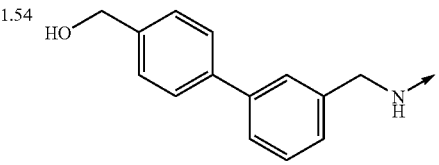 |
| 142 | 3-((2R)-2-{[(2R)-2-(6-aminopyridin-3-yl)-2-hydroxyethyl]-amino}propyl)-N-{[4'-(hydroxymethyl)-1,1'-biphenyl-3-yl]methyl}benzamide | 510.3 | ELSD | 1.54 | 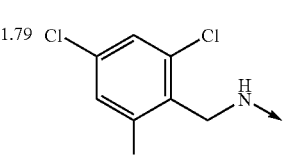 |
| 143 | 3-((2R)-2-{[(2R)-2-(6-aminopyridin-3-yl)-2-hydroxyethyl]-amino}propyl)-N-(2,4-dichloro-6-hydroxybenzyl)benzamide | 488.1 | ELSD | 1.79 | 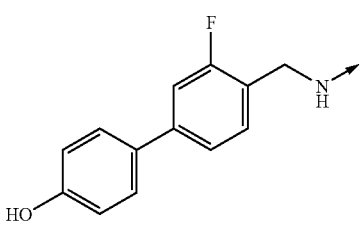 |
| 144 | 3-((2R)-2-{[(2R)-2-(6-aminopyridin-3-yl)-2-hydroxyethyl]-amino}propyl)-N-[(3-fluoro-4'-hydroxy-1,1'-biphenyl-4-yl)methyl]benzamide | 514.2 | ELSD | 1.69 | 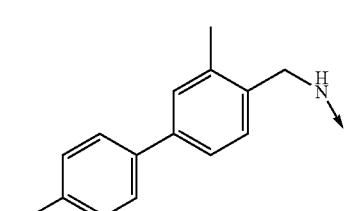 |
| 145 | 3-((2R)-2-{[(2R)-2-(6-aminopyridin-3-yl)-2-hydroxyethyl]-amino}propyl)-N-[(4'-hydroxy-3-methyl-1,1'-biphenyl-4-yl)methyl]benzamide | 510.3 | ELSD | 1.61 | 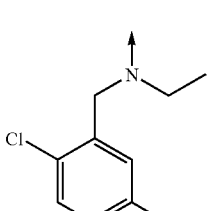 |
| 146 | 3-((2R)-2-{[(2R)-2-(6-aminopyridin-3-yl)-2-hydroxyethyl]-amino}propyl)-N-(2-chloro-5-hydroxy-benzyl)-N-ethylbenzamide | 482.2 | ELSD | 1.63 | 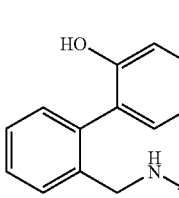 |
| 147 | 3-((2R)-2-{[(2R)-2-(6-aminopyridin-3-yl)-2-hydroxyethyl]-amino}propyl)-N-[(2'-hydroxy-1,1'-biphenyl-2-yl)methyl]benzamide | 496.3 | ELSD | 1.64 | |

-continued

| Ex | Name | Mass | Detector | Rt | |
|---|---|---|---|---|---|
| 148 | 3-((2R)-2-{[(2R)-2-(6-aminopyridin-3-yl)-2-hydroxyethyl]-amino}propyl)-N-[(4'-hydroxy-1,1'-biphenyl-2-yl)methyl]benzamide | 496.3 | ELSD | 1.59 | |
| 149 | 3-((2R)-2-{[(2R)-2-(6-aminopyridin-3-yl)-2-hydroxyethyl]-amino}propyl)-N-[3-hydroxy-5-(trifluoromethyl)benzyl]-N-methylbenzamide | 502.2 | ELSD | 1.65 | |
| 150 | 3-((2R)-2-{[(2R)-2-(6-aminopyridin-3-yl)-2-hydroxyethyl]-amino}propyl)-N-(3-chloro-5-hydroxybenzyl)-N-ethylbenzamide | 482.2 | ELSD | 1.55 | |
| 151 | 3-((2R)-2-{[(2R)-2-(6-aminopyridin-3-yl)-2-hydroxyethyl]-amino}propyl)-N-(3-chloro-5-hydroxybenzyl)benzamide | 454.2 | ELSD | 1.44 | |
| 152 | 3-((2R)-2-{[(2R)-2-(6-aminopyridin-3-yl)-2-hydroxyethyl]-amino}propyl)-N-[(4'-hydroxy-1,1'-biphenyl-3-yl)methyl]benzamide | 496.3 | ELSD | 1.63 | |
| 153 | 3-((2R)-2-{[(2R)-2-(6-aminopyridin-3-yl)-2-hydroxyethyl]-amino}propyl)-N-(4-hydroxy-3,5-dimethylbenzyl)benzamide | 448.3 | ELSD | 1.35 | |
| 154 | 3-((2R)-2-{[(2R)-2-(6-aminopyridin-3-yl)-2-hydroxyethyl]-amino}propyl)-N-(3,5-dichloro-2-hydroxybenzyl)benzamide | 488.1 | ELSD | 1.88 | |

-continued

| Ex | Name | Mass | Detector | Rt | |
|----|------|------|----------|-----|---|
| 155 | 3-((2R)-2-{[(2R)-2-(6-aminopyridin-3-yl)-2-hydroxyethyl]-amino}propyl)-N-[2-(2-hydroxyphenyl)-ethyl]benzamide | 434.2 | ELSD | 1.37 | |
| 156 | 3-((2R)-2-{[(2R)-2-(6-aminopyridin-3-yl)-2-hydroxyethyl]-amino}propyl)-N-(3-hydroxy-4-methoxy-phenyl)benzamide | 436.21 | ELSD | 1.23 | |
| 157 | 3-((2R)-2-{[(2R)-2-(6-aminopyridin-3-yl)-2-hydroxyethyl]-amino}propyl)-N-(3-hydroxyphenyl)benz-amide | 406.2 | ELSD | 1.31 | |
| 158 | 3-((2R)-2-{[(2R)-2-(6-aminopyridin-3-yl)-2-hydroxyethyl]-amino}propyl)-N-(4-hydroxy-3-methoxy-benzyl)benzamide | 450.23 | ELSD | 1.31 | |
| 159 | 3-((2R)-2-{[(2R)-2-(6-aminopyridin-3-yl)-2-hydroxyethyl]-amino}propyl)-N-[5-(ethylsulfonyl)-2-hydroxyphenyl]benza-mide | 498.19 | ELSD | 1.17 | |
| 160 | 3-((2R)-2-{[(2R)-2-(6-aminopyridin-3-yl)-2-hydroxyethyl]-amino}propyl)-N-(2-hydroxy-5-methyl-phenyl)benzamide | 420.22 | ELSD | 1.57 | |
| 161 | 3-((2R)-2-{[(2R)-2-(6-aminopyridin-3-yl)-2-hydroxyethyl]-amino}propyl)-N-(3-hydroxy-2-methyl-phenyl)benzamide | 420.22 | ELSD | 1.2 | |
| 162 | 3-((2R)-2-{[(2R)-2-(6-aminopyridin-3-yl)-2-hydroxyethyl]-amino}propyl)-N-[2-(4-hydroxyphen-yl)ethyl]benzamide | 434.23 | ELSD | 1.25 | |
| 163 | 3-((2R)-2-{[(2R)-2-(6-aminopyridin-3-yl)-2-hydroxyethyl]-amino}propyl)-N-(4-hydroxybenzyl)benza-mide | 420.22 | ELSD | 1.18 | |

-continued

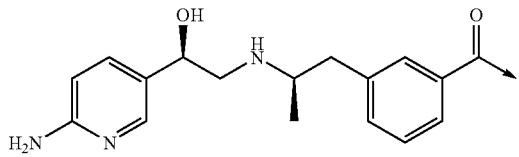

| Ex | Name | Mass | Detector | Rt | |
|---|---|---|---|---|---|
| 165 | 3-((2R)-2-{[(2R)-2-(6-aminopyridin-3-yl)-2-hydroxyethyl]-amino}propyl)-N-(2-hydroxybenzyl)benzamide | 420.22 | ELSD | 1.49 | |
| 168 | 3-((2R)-2-{[(2R)-2-(6-aminopyridin-3-yl)-2-hydroxyethyl]-amino}propyl)-N-(3-hydroxybenzyl)benzamide | 420.22 | ELSD | 1.23 | |
| 169 | 3-((2R)-2-{[(2R)-2-(6-aminopyridin-3-yl)-2-hydroxyethyl]-amino}propyl)-N-[2-(3-hydroxyphenyl)ethyl]benzamide | 434.23 | ELSD | 1.34 | |

Preparation 1

N-Benzyl-2-[3-((2R)-2-{(2R)-2-[6-(2,5-dimethyl-pyrrol-1-yl)-pyridin-3-yl]-2-hydroxy-ethylamino}-propyl)-phenyl]-acetamide

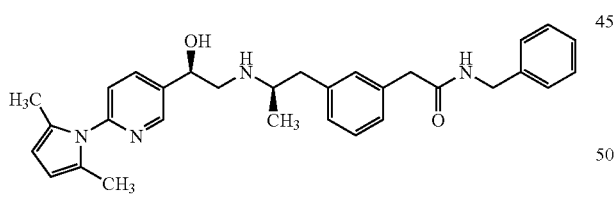

A solution of the acid from preparation 21 (200 mg, 0.41 mmol), O-benzotriazol-1-yl-N,N,N',N'-tetramethyluronium hexafluorophosphate (114 mg, 0.48 mmol), triethylamine (1.0 ml, 7.17 mmol) and benzylamine (52 mg, 0.48 mmol) in N,N-dimethylformamide (3 ml) was stirred at room temperature for 40 hours under a nitrogen atmosphere. The reaction mixture was diluted with water (3 ml) and extracted with ethyl acetate (2×10 ml). The combined organic extracts were dried (sodium sulfate) and reduced in vacuo. Purification by flash column chromatography eluting with dichloromethane:methanol:ammonia (100:0:0 changing to 94:6:0.5 by volume) gave the title compound as a pale yellow oil (148 mg).

$^1$H NMR (400 MHz, CD$_3$OD): δ=8.52 (1H, s), 7.96 (1H, d), 7.30-7.09 (10H, m), 5.82 (2H, s), 4.86 (1H, m), 4.34 (2H, s), 3.53 (2H, s), 3.01 (1H, m), 2.88 (2H, m), 2.80 (1H, m), 2.61 (1H, m), 2.03 (6H, s), 1.08 (3H, d) ppm.

LRMS (APCl): m/z [M+H]$^+$ 497.

Preparation 2

2-[3-((2R)-2-{(2R)-2-[6-(2,5-Dimethyl-pyrrol-1-yl)-pyridin-3-yl]-2-hydroxy-ethylamino}-propyl)-phenyl]-N-(2-methoxy-benzyl)-acetamide

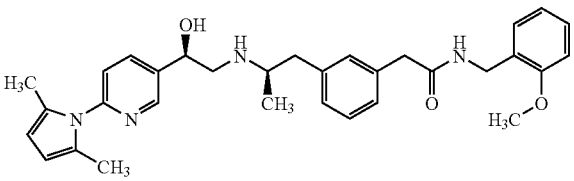

Prepared according to the method described for preparation 1 using the appropriate amine to give the title compound as a pale yellow oil.

$^1$H NMR (400 MHz, CD$_3$OD): δ=8.51 (1H, s), 7.92 (1H, d), 7.29-6.83 (9H, m), 5.81 (2H, s), 4.81 (1H, m), 4.34 (2H, s), 3.77 (3H, s), 3.52 (2H, s), 2.95 (1H, s), 2.85 (2H, m), 2.74 (1H, m), 2.59 (1H, m), 2.03 (6H, s), 1.06 (3H, d) ppm.

LRMS (APCl): m/z [M+H]$^+$ 527.

Preparation 3

2-[3-((2R)-2-{(2R)-2-[6-(2,5-Dimethyl-pyrrol-1-yl)-pyridin-3-yl]-2-hydroxy-ethylamino}-propyl)-phenyl]-N-(2-ethoxy-benzyl)-acetamide

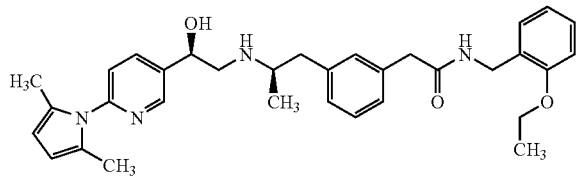

Prepared according to the method described for preparation 1 using the appropriate amine to give the title compound as a pale yellow oil.

$^1$H NMR (400 MHz, CD$_3$OD): δ=8.50 (1H, s), 7.94 (1H, d), 7.29-6.80 (9H, m), 5.82 (2H, s), 4.83 (1H, m), 4.35 (2H, s), 3.99 (2H, q), 3.52 (2H, s), 2.96 (1H, m), 2.85 (2H, m), 2.76 (1H, m), 2.55 (1H, m), 2.03 (6H, s), 1.33 (3H, t), 1.06 (3H, d) ppm.

LRMS (APCl): m/z [M+H]$^+$ 541.

Preparation 4

2-[3-((2R)-2-{(2R)-2-[6-(2,5-Dimethyl-pyrrol-1-yl)-pyridin-3-yl]-2-hydroxy-ethylamino}-propyl)-phenyl]-N-(3-phenyl-propyl)-acetamide

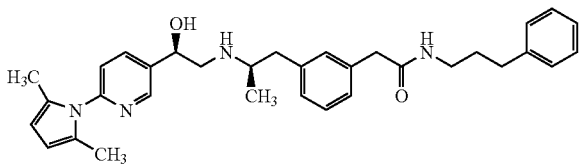

Prepared according to the method described for preparation 1 using the appropriate amine to give the title compound as a pale yellow oil.

$^1$H NMR (400 MHz, CD$_3$OD): δ=8.52 (1H, s), 7.94 (1H, d), 7.28-7.08 (10H, m), 5.82 (2H, s), 4.82 (1H, m), 3.47 (2H, s), 3.19 (2H, m), 3.00 (1H, m), 2.86-2.77 (3H, m), 2.60-2.54 (3H, m), 2.03 (6H, s), 1.77 (2H, m), 1.05 (3H, d) ppm.

LRMS (APCl): m/z [M+H]$^+$ 525.

Preparation 5

2-[3-((2R)-2-{(2R)-2-[6-(2,5-Dimethyl-pyrrol-1-yl)-pyridin-3-yl]-2-hydroxy-ethylamino}-propyl)-phenyl]-N-phenethyl-acetamide

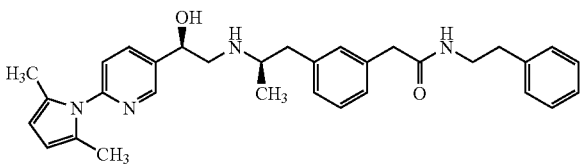

Prepared according to the method described for preparation 1 using the appropriate amine to give the title compound as a pale yellow oil.

$^1$H NMR (400 MHz, CD$_3$OD): δ=8.51 (1H, d), 7.95 (1H, d), 7.29-7.08 (10H, m), 5.81 (2H, s), 4.83 (1H, m), 3.44 (2H, s), 2.99 (1H, m), 2.85 (3H, m), 2.77 (4H, m), 2.60 (1H, m), 2.04 (6H, s), 1.08 (3H, d) ppm.

LRMS (APCl): m/z [M+H]$^+$ 511.

Preparation 6

N-(3,4-Dimethyl-benzyl)-2-[3-((2R)-2-{(2R)-2-[6-(2,5-dimethyl-pyrrol-1-yl)-pyridin-3-yl]-2-hydroxy-ethylamino}-propyl)-phenyl]-acetamide

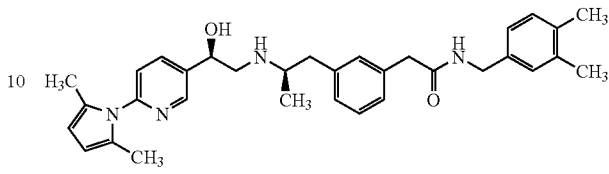

Prepared according to the method for preparation 1 using the appropriate amine to give the title compound as a pale yellow oil.

$^1$H NMR (400 MHz, CD$_3$OD): δ=8.55 (1H, s), 7.95 (1H, d), 7.32-6.90 (8H, m), 5.81 (2H, s), 4.90 (1H, m), 4.25 (2H, s), 3.52 (2H, s), 3.18 (1H, m), 3.00 (2H, m), 2.88 (1H, m), 2.65 (1H, m), 2.18 (6H, s), 2.02 (6H, s), 1.06 (3H, d) ppm.

LRMS (APCl): m/z [M+H]$^+$ 525.

Preparation 7

2-[3-((2R)-2-{(2R)-2-[6-(2,5-Dimethyl-pyrrol-1-yl)-pyridin-3-yl]-2-hydroxy-ethylamino}-propyl)-phenyl]-N-indan-2-yl-acetamide

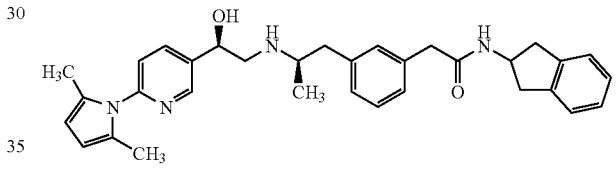

Prepared according to the method described for preparation 1 using the appropriate amine to give the title compound as a pale yellow oil.

$^1$H NMR (400 MHz, CD$_3$OD): δ=8.57 (1H, s), 8.00 (1H, d), 7.33-7.10 (9H, m), 5.82 (2H, s), 4.94 (1H, m), 4.55 (1H, m), 3.47 (2H, s), 3.31-2.66 (9H, m), 2.04 (6H, s), 1.17 (3H, d) ppm.

LRMS (APCl): m/z [M+H]$^+$ 523.

Preparation 8

N-(3,4-Dichloro-benzyl)-2-[3-((2R)-2-{(2R)-2-[6-(2,5-dimethyl-pyrrol-1-yl)-pyridin-3-yl]-2-hydroxy-ethylamino}-propyl)-phenyl]-acetamide

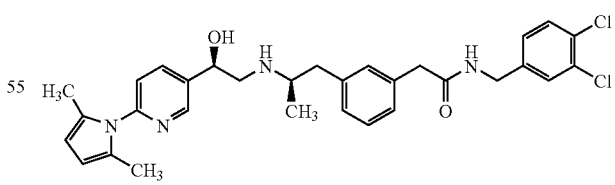

Prepared according to the method described for preparation 1 using 3,4-dichlorobenzylamine as the amine to give the title compound as a pale yellow oil.

$^1$H NMR (400 MHz, CD$_3$OD): δ=8.56 (1H, s), 8.01 (1H, d), 7.59-7.13 (8H, m), 5.82 (2H, s), 4.92 (1H, m), 4.32 (2H, s), 3.55 (2H, s), 3.20 (1H, m), 3.05 (2H, m), 2.91 (1H, m), 2.70 (1H, m), 2.04 (6H, s), 1.15 (3H, d) ppm.

LRMS (APCl): m/z [M+H]$^+$ 541/543.

Preparation 9

2-[3-(2-{(2R)-2-[6-(2,5-Dimethyl-pyrrol-1-yl)-pyridin-3-yl]-2-hydroxy-ethylamino}-propyl)-phenyl]-N-(4-hydroxy-3-methoxy-benzyl)-acetamide

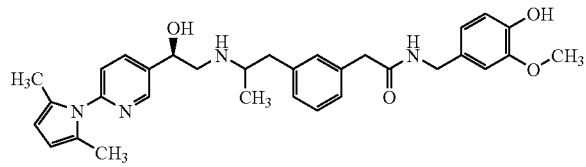

Prepared according to the method described for preparation 1 using the acid from preparation 30 and the appropriate amine to give the title compound as a pale yellow oil.

$^1$H NMR (400 MHz, CDCl$_3$): δ=8.47 (1H, m), 7.78-7.75 (1H, m), 7.28-7.24 (1H, m), 7.17-7.08 (3H, m), 6.86-6.61 (4H, m), 6.01-5.94 (3H, m), 4.72-4.57 (1H, m), 4.34-4.25 (2H, m), 3.80 (3H, m), 3.58-3.56 (2H, m), 3.10-2.57 (5H, m), 2.09 (6H, s), 1.13 (3H, t) ppm.

LRMS (APCl): m/z [M+H]$^+$ 543, [M+Na]$^+$ 565, [M−H]$^−$ 541.

Preparation 10

2-[4-(2-{(2R)-2-[6-(2,5-Dimethyl-pyrrol-1-yl)-pyridin-3-yl]-2-hydroxy-ethylamino}-2-methyl-propyl)-phenyl]-N-(3-methoxy-benzyl)-acetamide

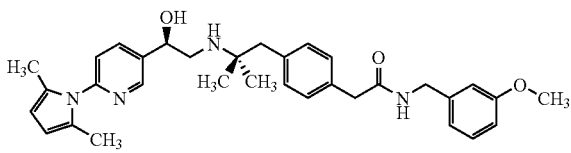

Prepared according to the method for preparation 1 using the acid from preparation 36 and the appropriate amine to give the title compound as a pale yellow foam.

$^1$H NMR (400 MHz, CDCl$_3$): δ=8.58 (1H, s), 7.82 (1H, d), 7.20 (4H, m), 7.18 (2H, m), 6.78 (2H, m), 6.72 (1H, s), 5.98 (1H, bs), 5.85 (2H, s), 4.62 (1H, dd), 4.38 (2H, d), 3.72 (3H, s), 3.58 (2H, s), 3.00 (1H, dd), 2.65 (3H, m), 2.08 (6H, s), 1.11 (3H, s), 1.10 (3H, s) ppm.

LRMS (APCl): m/z [M+H]$^+$ 541.

Preparation 11

N-(2,6-Dimethoxy-benzyl)-2-[4-(2-{(2R)-2-[6-(2,5-dimethyl-pyrrol-1-yl)-pyridin-3-yl]-2-hydroxy-ethylamino}-2-methyl-propyl)-phenyl]-acetamide

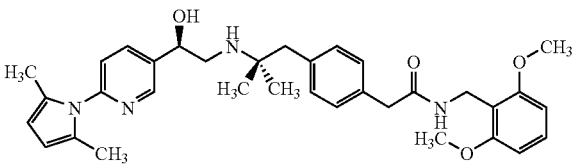

Prepared according to the method for preparation 1 using the acid from preparation 36 and the appropriate amine to give the title compound as a pale yellow solid.

$^1$H NMR (400 MHz, CDCl$_3$): δ=8.58 (1H, s), 7.90 (1H, d), 7.20-7.10 (6H, m), 6.50 (2H, d), 6.00 (1H, s), 5.90 (2H, s), 4.70 (1H, dd), 4.50 (2H, d), 3.73 (6H, s), 3.50 (2H, s), 3.05 (1H, dd), 2.72 (3H, m), 2.10 (6H, s), 1.11 (3H, s), 1.10 (3H, s) ppm.

LRMS (APCl): m/z [M+H]$^+$ 571.

Preparation 12

2-[3-(2-{(2R)-2-[6-(2,5-Dimethyl-pyrrol-1-yl)-pyridin-3-yl]-2-hydroxy-ethylamino}-2-methyl-propyl)-phenyl]-N-(4-sulfamoyl-benzyl)-acetamide

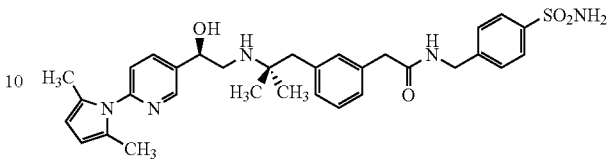

Prepared according to the method for preparation 1 using the acid from preparation 34 and the appropriate amine to give the title compound as a pale yellow solid.

$^1$H NMR (400 MHz, CD$_3$OD): δ=8.58 (1H, s), 8.03 (1H, d), 7.79 (2H, d), 7.37 (2H, d), 7.31 (1H, d), 7.23 (1H, d), 7.18 (2H, m), 7.13 (1H, d), 5.82 (2H, s), 4.81 (1H, partially obscured by solvent), 4.42 (2H, s), 3.56 (2H, s), 2.91-2.88 (2H, m), 2.78-2.66 (2H, m), 2.04 (6H, s), 1.07 (3H, s), 1.04 (3H, s) ppm.

LRMS (APCl): m/z [M+H]$^+$ 590, [M−H]$^−$ 588.

Preparation 13

2-[3-(2-{(2R)-2-[6-(2,5-Dimethyl-pyrrol-1-yl)-pyridin-3-yl]-2-hydroxy-ethylamino}-2-methyl-propyl)-phenyl]-N-(2-ethoxy-benzyl)-acetamide

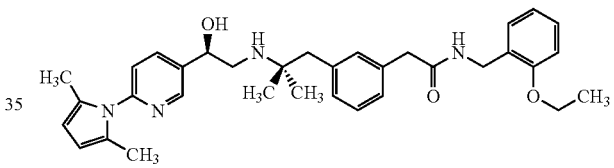

Prepared according to the method for preparation 1 using the acid from preparation 34 and the appropriate amine to give the title compound as a pale yellow solid.

$^1$H NMR (400 MHz, CD$_3$OD): δ=8.58 (1H, s), 8.02 (1H, d), 7.30 (1H, d), 7.25-7.10 (5H, m), 6.91-6.80 (3H, m), 5.80 (2H, s), 4.92 (1H, partially obscured by solvent), 4.38 (2H, s), 4.02 (2H, q), 3.55 (2H, s), 2.90-2.82 (2H, m), 2.78-2.65 (2H, m), 2.03 (6H, s), 1.03 (3H, t), 1.05 (3H, s), 1.04 (3H, s) ppm.

LRMS (APCl): m/z [M+H]$^+$ 555.

Preparation 14

2-[3-(2-{(2R)-2-[6-(2,5-Dimethyl-pyrrol-1-yl)-pyridin-3-yl]-2-hydroxy-ethylamino}-2-methyl-propyl)-phenyl]-N-indan-2-yl-acetamide

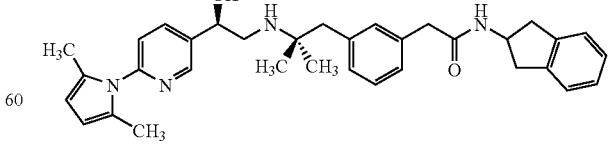

Prepared according to the method described for preparation 1 using the acid from preparation 34 and the appropriate amine to give the title compound as a pale yellow oil.

$^1$H NMR (400 MHz, CD$_3$OD): δ=8.58 (1H, s), 8.05 (1H, d), 7.30 (1H, d), 7.25-7.08 (8H, m), 5.81 (2H, s), 4.55 (1H, m), 3.47 (2H, s), 3.25 (1H, d), 3.20 (1H, d), 2.98-2.90 (7H, m), 2.00 (6H, s), 1.10 (3H, s), 1.09 (3H, s) ppm.

LRMS (APCl): m/z [M+H]⁺ 537.

Preparation 15

N-Benzyl-2-[3-(2-{(2R)-2-[6-(2,5-dimethyl-pyrrol-1-yl)-pyridin-3-yl]-2-hydroxy-ethylamino}-2-methyl-propyl)-phenyl]-acetamide

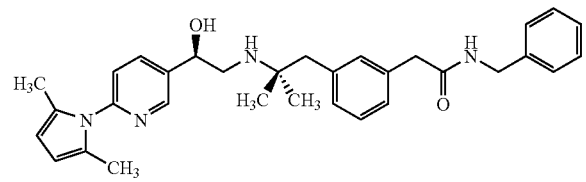

Prepared according to the method described for preparation 1 using the acid from preparation 34 and the appropriate amine to give the title compound as a pale yellow oil.

$^1$H NMR (400 MHz, CD$_3$OD): δ=8.58 (1H, s), 8.03-8.00 (1H, m), 7.31-7.10 (10H, m), 5.82 (2H, s), 4.82 (1H, m, partially obscured by solvent), 4.35 (2H, s), 3.54 (2H, s), 2.94-2.84 (2H, m), 2.77-2.66 (2H, dd), 2.04 (6H, s), 1.07 (3H, s), 1.04 (3H, s) ppm.

LRMS (electrospray): m/z [M+H]⁺ 511, [M+Na]⁺ 533, [M−H]⁻ 509.

Preparation 16

2-[3-(2-{(2R)-2-[6-(2,5-Dimethyl-pyrrol-1-yl)-pyridin-3-yl]-2-hydroxy-ethylamino}-2-methyl-propyl)-phenyl]-N-phenethyl-acetamide

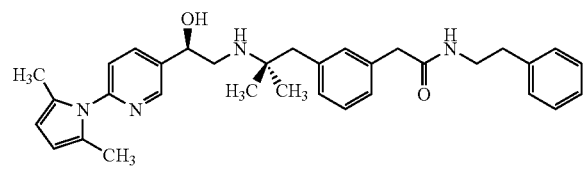

Prepared according to the method described for preparation 1 using the acid from preparation 34 and the appropriate amine to give the title compound as a pale yellow oil.

$^1$H NMR (400 MHz, CD$_3$OD): δ=8.58 (1H, s), 8.03-8.01 (1H, m), 7.30 (1H, d), 7.24-7.09 (9H, m), 5.82 (2H, s), 4.85 (1H, m, obscured by solvent), 3.45 (2H, s), 3.41-3.38 (2H, m), 2.94-2.86 (2H, m), 2.78-2.66 (4H, m), 2.04 (6H, s), 1.08 (3H, s), 1.05 (3H, s) ppm.

LRMS (electrospray): m/z [M+H]⁺ 525, [M+Na]⁺ 547, [M−H]⁻ 523.

Preparation 17

2-[3-(2-{(2R)-2-[6-(2,5-Dimethyl-pyrrol-1-yl)-pyridin-3-yl]-2-hydroxy-ethylamino}-2-methyl-propyl)-phenyl]-N-(3-phenyl-propyl)-acetamide

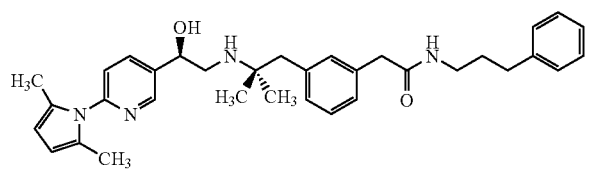

Prepared according to the method described for preparation 1 using the acid from preparation 34 and the appropriate amine to give the title compound as a pale yellow oil.

$^1$H NMR (400 MHz, CD$_3$OD): δ=8.58 (1H, s), 8.02-8.00 (1H, m), 7.31-7.11 (10H, m), 5.82 (2H, s), 4.82 (1H, partially obscured by solvent), 3.49 (2H, s), 3.20-3.17 (2H, m), 2.94-2.85 (2H, m), 2.79-2.67 (2H, m), 2.59-2.55 (2H, m), 2.04 (6H, s), 1.81-1.74 (2H, m), 1.08 (3H, s), 1.05 (3H, s) ppm.

LRMS (electrospray): m/z [M+H]⁺ 539, [M+Na]⁺ 561, [M−H]⁻ 537.

Preparation 18

N-(3,5-Dichloro-benzyl)-2-[3-(2-{(2R)-2-[6-(2,5-dimethyl-pyrrol-1-yl)-pyridin-3-yl]-2-hydroxy-ethylamino}-2-methyl-propyl)-phenyl]-acetamide

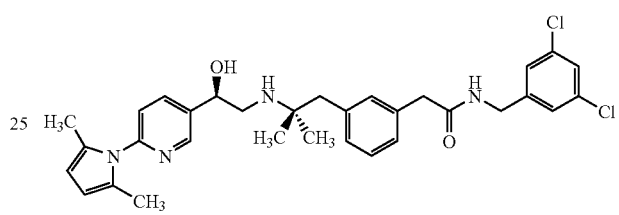

Prepared according to the method described for preparation 1 using the acid from preparation 34 and the appropriate amine to give the title compound as a pale yellow oil.

$^1$H NMR (400 MHz, CD$_3$OD): δ=8.59 (1H, s), 8.03-8.01 (1H, m), 7.32-7.11 (8H, m), 5.82 (2H, s), 4.83 (1H, m, partially obscured by solvent), 4.32 (2H, s), 3.56 (2H, s), 2.95-2.84 (2H, m), 2.79-2.67 (2H, dd), 2.04 (6H, s), 1.07 (3H, s), 1.04 (3H, s) ppm.

LRMS (electrospray): m/z [M+H]⁺ 579/581, [M+Na]⁺ 601/603, [M−H]⁻ 577/579.

Preparation 19

N-(2,3-Dimethyl-benzyl)-2-[3-(2-{(2R)-2-[6-(2,5-dimethyl-pyrrol-1-yl)-pyridin-3-yl]-2-hydroxy-ethylamino}-2-methyl-propyl)-phenyl]-acetamide Prepared according to the method described for preparation 1 using the acid from preparation 34 and the appropriate amine to give the title compound as a pale yellow oil.

$^1$H NMR (400 MHz, CD$_3$OD): δ=8.61 (1H, s), 8.05-8.03 (1H, m), 7.32-6.95 (8H, m), 5.83 (2H, s), 4.95-4.92 (1H, m), 4.36 (2H, s), 3.53 (2H, s), 3.05-3.03 (2H, m), 2.86-2.76 (2H, dd), 2.24 (3H, s), 2.13 (3H, s), 2.04 (6H, s), 1.15 (3H, s), 1.13 (3H, s) ppm.

LRMS (electrospray): m/z [M+H]⁺ 539, [M+Na]⁺ 561, [M−H]⁻ 537.

Preparation 20

N-(3,4-Dichloro-benzyl)-2-[3-(2-{(2R)-2-[6-(2,5-dimethyl-pyrrol-1-yl)-pyridin-3-yl]-2-hydroxy-ethylamino}-2-methyl-propyl)-phenyl]-acetamide

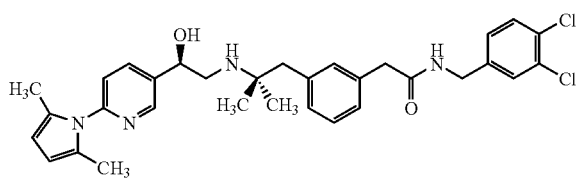

Prepared according to the method described for preparation 1 using the acid from preparation 34 and the appropriate amine to give the title compound as a pale yellow oil.

$^1$H NMR (400 MHz, CD$_3$OD): δ=8.58 (1H, s), 8.03-8.01 (1H, m), 7.46-7.11 (8H, m), 5.82 (2H, s), 4.82 (1H, m, partially obscured by solvent), 4.32 (2H, s), 3.55 (2H, s), 2.94-2.84 (2H, m), 2.78-2.66 (2H, dd), 2.04 (6H, s), 1.06 (3H, s), 1.03 (3H, s) ppm.

LRMS (electrospray): m/z [M+H]$^+$ 579/581, [M+Na]$^+$ 601/603, [M−H]$^−$ 577/579.

Preparation 21

[3-((2R)-2-{(2R)-2-[6-(2,5-Dimethyl-pyrrol-1-yl)-pyridin-3-yl]-2-hydroxy-ethylamino}-propyl)-phenyl]-acetic acid

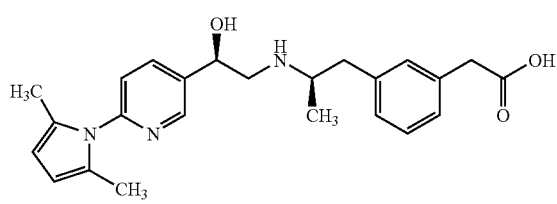

A solution of the ester from preparation 22 (5.45 g, 12.93 mmol) in tetrahydrofuran (80 ml) was treated with 1N lithium hydroxide (26 ml, 26 mmol) and the resulting mixture left to stir at room temperature for 16 hours. 1N hydrogen chloride (26 ml, 26 mmol) was added, and the solvent was removed in vacuo. The residue was azeotropically dried with toluene and then purified by flash column chromatography eluting with dichloromethane:methanol:880 ammonia (90:10:1 changing to 80:20:3 by volume) to give the title compound as a colourless solid (3.7 g).

$^1$H NMR (400 MHz, DMSO$_{d6}$): δ=8.54 (1H, bs), 7.92-7.90 (1H, m), 7.33 (1H, d), 7.16 (1H, d), 7.07-7.00 (3H, m), 5.77 (2H, s), 4.77-4.74 (1H, m), 3.47 (2H, s), 2.91-2.75 (4H, m), 2.43-2.38 (1H, m), 2.01 (6H, s), 0.92 (3H, d) ppm.

LRMS (APCl): m/z [M+H]$^+$ 408.

Preparation 22

[3-((2R)-2-{(2R)-2-[6-(2,5-Dimethyl-pyrrol-1-yl)-pyridin-3-yl]-2-hydroxy-ethylamino}-propyl)-phenyl]-acetic acid methyl ester

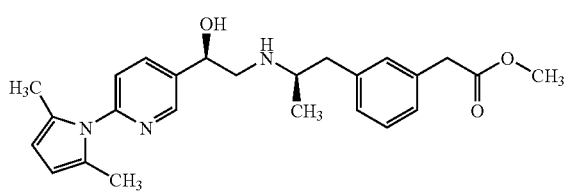

A solution of the epoxide from preparation 27 (5.43 g of 66% b/w crude material, 3.58 g, 16.7 mmol) and the amine from preparation 23 (4.15 g, 20.02 mmol) in dimethyl sulfoxide (50 ml) was heated at 85° C. under nitrogen for a period of 16 hours. The reaction mixture was cooled to room temperature and loaded directly onto a Strong Cation Exchange column. The column was eluted with methanol (300 ml) and then the product eluted with 2M ammonia in methanol (100 ml). The solvent was removed in vacuo and the residue purified by flash column chromatography eluting with dichloromethane:methanol:880 ammonia (100 changing to 98:2:0.2 by volume) to give the title compound as a pale orange oil (5.45 g).

$^1$H NMR (400 MHz, CD$_3$OD): δ=8.54 (1H, bs), 7.79 (1H, dd), 7.31-7.22 (2H, m), 7.15-7.10 (3H, m), 5.82 (2H, s), 491-4.81 (1H, m, partially obscured by solvent), 3.67 (3H, s), 3.63 (2H, s), 3.04-2.96 (1H, m), 2.88 (2H, d), 2.81-2.74 (1H, m), 2.66-2.58 (1H, m), 2.04 (6H, s), 1.09 (3H, d) ppm.

LRMS (electrospray): m/z [M+H]$^+$ 422, [M+Na]$^+$ 444, [M−H]$^−$ 420.

Preparation 23

[3-((2R)-2-Amino-propyl)-phenyl]-acetic acid methyl ester hydrochloride

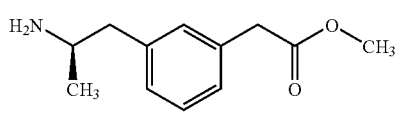

A solution of the amine from preparation 24 (7.69 g, 22 mmol) and ammonium formate (6.94 g, 110 mmol) was heated to 75° C. in the presence of 20% of palladium hydroxide-on-charcoal (2.00 g). After 90 minutes the reaction mixture was cooled to room temperature, filtered through arbocel® and the filtrate concentrated in vacuo. The residue was partitioned between dichloromethane (100 ml) and 880 ammonia (100 ml) and the organic phase separated. The aqueous phase was extracted with dichloromethane (100 ml) and the combined organic extracts dried (magnesium sulfate) and reduced in vacuo to give the title compound as a colourless oil (4.78 g).

$^1$H NMR (400 MHz, CD$_3$OD): δ=7.27-7.23 (1H, t), 7.13-7.09 (3H, m), 3.67 (3H, s), 3.63 (2H, s), 3.12-3.05 (1H, m), 2.67-2.57 (2H, m), 1.06 (3H, d) ppm.

LRMS (electrospray): m/z [M+H]$^+$ 208, [M+Na]$^+$ 230.

Preparation 24

{3-[(2R)-2-((1R)-1-Phenyl-ethylamino)-propyl]-phenyl}-acetic acid methyl ester

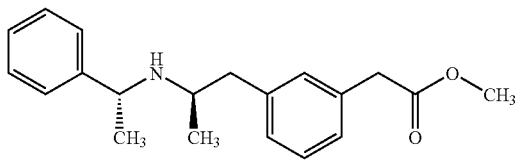

A solution of the ketone from preparation 25 (8.5 g, 41.2 mmol), (R)-α-methyl benzylamine (4.8 ml, 37.2 mmol), sodium triacetoxyborohydride (11.6 g, 56 mmol) and acetic acid (2.2 ml, 38 mmol) in dichloromethane (400 ml) was stirred at room temperature for 48 hours. The reaction mixture was quenched by addition of saturated aqueous sodium bicarbonate (200 ml) and allowed to stir until effervescence ceased. The organic phase was separated and the aqueous phase extracted with dichloromethane (100 ml). The combined organic extracts were dried (magnesium sulfate) and reduced in vacuo. Purification by flash column chromatography eluting with dichloromethane:methanol: 880 ammonia (99:1:0.1 changing to 95:5:0.5 by volume) gave a 4:1 mixture of diastereomers (R,R major) as a pale yellow oil (8.71 g). Treatment with excess 1M hydrogen chloride in methanol followed by three successive crystallisations (diisopropylether/methanol) gave the title compound as a colourless crystalline solid (5.68 g).

$^1$H NMR (400 MHz, CD$_3$OD): δ=7.52-7.48 (5H, m), 7.28-7.25 (1H, m), 7.18-7.16 (1H, m), 7.02-6.99 (2H, m), 4.59 (1H, q), 3.62 (2H, s), 3.30 (3H, s), 3.30-3.25 (1H, m), 3.26-3.15 (1H, m), 2.66-2.60 (1H, m), 1.68 (3H, d), 1.18, (3H, d) ppm.

LRMS (electrospray): m/z [M+H]$^+$ 312, [M+Na]$^+$ 334.

Preparation 25

[3-(2-Oxo-propyl)-phenyl]-acetic acid methyl ester

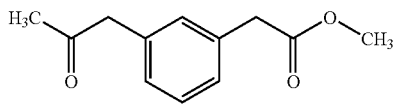

A solution of the bromide from preparation 26 (15.0 g, 65.0 mmol), tributyltin methoxide (28.3 ml, 98 mmol), isopropenyl acetate (10.8 ml, 98.0 mmol), palladium(II) acetate (750 mg, 3.30 mmol) and tri-ortho-tolylphosphine (2.0 g, 6.5 mmol) were stirred together in toluene (75 ml) at 100° C. under nitrogen for 5 hours. After cooling the reaction was diluted with ethyl acetate (150 ml) and 4M aqueous potassium fluoride solution (90 ml) and stirred for 15 minutes. The mixture was filtered through arbocel® and the organic phase separated and reduced in vacuo. The residue was purified by flash column chromatography silica gel eluting with a solvent gradient of diethyl ether:pentane: dichloromethane (0:100:0 changing to 25:75:0 then to 0:0: 100, by volume) to give the title compound as a pale yellow oil (12.6 g).

$^1$H NMR (400 MHz, CDCl$_3$): δ=7.30 (1H, t), 7.19 (1H, d), 7.13-7.10 (2H, m), 3.69 (5H, s), 3.61 (2H, s), 2.15 (3H, s) ppm.

LRMS (electrospray): m/z [M+NH$_4$]$^+$ 224, [M+Na]$^+$ 229.

Preparation 26

(3-Bromo-phenyl)-acetic acid methyl ester

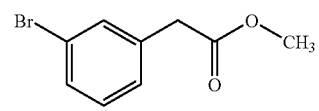

Acetyl chloride (0.7 ml, 9.3 mmol) was slowly added to a solution of (3-bromo-phenyl)-acetic acid (20.0 g, 93 mmol) in methanol (500 ml) at 0° C. under nitrogen and the reaction was allowed to warm gradually to room temperature over a period of 5 hours. The solvent was removed in vacuo and the residue disolved in dichloromethane, dried (sodium sulfate) and concentrated in vacuo to give the title compound as a colourless oil (20.6 g).

$^1$H NMR (400 MHz, CDCl$_3$): δ=7.37-7.45 (2H, m), 7.24-7.17 (2H, m), 3.70 (3H, s), 3.59 (2H, s) ppm.

LRMS (electrospray): m/z [M+Na]$^+$ 253.

Preparation 27

2-(2,5-Dimethyl-pyrrol-1-yl)-5-[(2R)-oxiranyl]pyridine

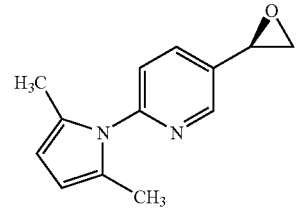

A solution of the chloride from preparation 28 (12.0 g, 48.1 mmol) in tetrahydrofuran (20 ml) was slowly added to a solution of (−)-B-chlorodiisopinocampheylborane (20.1 g, 62.5 mmol) in tert-butyl-methylether (15 ml) and tetrahydrofuran (30 ml) at −30° C. under nitrogen. The reaction was stirred for 6 hours at −30° C. and then sodium perborate tetrahydrate (7.4 g, 48.1 mmol) followed by tert-butyl-methylether (50 ml) were added. The reaction was stirred at room temperature for 18 hours, treated with 2M aqueous sodium hydroxide (190 ml) and stirred for a further 6 hours. The organic phase was separated and the aqueous phase extracted with further tert-butyl-methylether (50 ml). The combined organic extracts were washed with 1M aqueous sodium hydroxide (50 ml), saturated aqueous sodium chloride (50 ml), dried (sodium sulfate) and concentrated in vacuo. The residue was purified by flash column chromatography on silica gel eluting with pentane:dichloromethane (80:2 changing to 100:0, by volume) to give the crude epoxide (65% b/w, 11.0 g), which was used without further purification.

$^1$H NMR (400 MHz, CDCl$_3$): δ=8.58 (1H, bs), 7.68-7.66 (1H, dd), 7.22-7.20 (1H, d), 3.97-3.96 (1H, m), 3.26-3.24 (1H, m), 2.91-2.89 (1H, m), 2.12 (6H, s) ppm.

LRMS (electrospray): m/z [M+H]$^+$ 215, [M+Na]$^+$, 237.

Preparation 28

2-Chloro-1-[6-(2,5-dimethyl-pyrrol-1-yl)-pyridin-3-yl]-ethanone

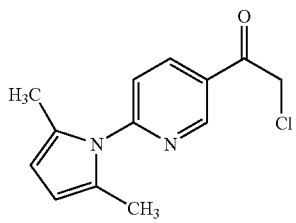

A solution of 2.5 M n-butyl lithium in hexanes (35 ml, 87.6 mmol) was added to a solution of the bromide from preparation 29 (20.0 g, 79.7 mmol) in tert-butyl methylether (300 ml) at −78° C. under nitrogen over 10 minutes. The reaction was stirred for a further 10 minutes and 2-chloro-N-methoxy-N-methyl-acetamide (12.1 g, 87.6 mmol) in tert-butyl-methylether (40 ml) was added slowly. The reaction was stirred at −78° C. for 20 minutes and then 1M hydrochloric acid (200 ml) was added. The mixture was allowed to warm to room temperature, stirred for 2 hours and the organic phase separated. The aqueous phase was extracted with tert-butyl methylether and the combined organic extracts were washed with water (100 ml), saturated aqueous sodium chloride (100 ml) and 1M sodium hydroxide (100 ml). The organic phase was dried (sodium sulfate), concentrated in vacuo and the residual oil purified by flash column chromatography on silica gel eluting with pentane:dichloromethane:methanol (75:25:0 changing to 0:99:1, by volume). The residue was recrystallised from pentane:dichloromethane to give the title compound as a yellow solid.

$^1$H NMR (400 MHz, CDCl$_3$): δ=9.11 (1H, s), 8.34-8.33 (1H, d), 7.32-7.30 (1H, d), 5.91 (2H, s), 4.66 (2H, s), 2.17 (6H, s) ppm.

LRMS (electrospray): m/z [M−H]$^+$ 247.

Preparation 29

5-Bromo-2-(2,5-dimethyl-pyrrol-1-yl)-pyridine

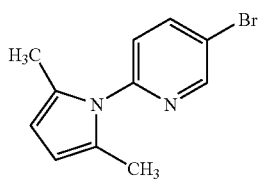

2,5-hexanedione (46.2 g, 0.41 mol) was added to a suspension of 2-amino-5-bromopyridine (50.0 g, 0.29 mol) and the reaction heated to reflux for 24 hours under Dean and Stark conditions. para-Toluene sulfonic acid (100 mg) was added and the reaction was refluxed for a further 18 hours. 8 ml of water were removed, so the reaction was cooled to room temperature, washed with water (100 ml) and passed through a plug of silica gel, eluting with toluene. The eluent was concentrated in vacuo and the residue dissolved in pentane:dichloromethane (1:1 by volume) and passed through a plug of silica gel, eluting with pentane:dichloromethane (1:1 by volume). The eluent was concentrated in vacuo to give a red liquid, which solidified on standing. The solid was recrystallised (isopropanol) to give the title compound as a pale yellow solid (54.4 g).

$^1$H NMR (400 MHz, CDCl$_3$): δ=8.66 (1H, s), 7.93-7.92 (1H, d), 7.13-7.11 (1H, d), 5.91 (2H, s), 2.13 (6H, s) ppm.

LRMS (thermospray): m/z [M+H]$^+$ 252.

Preparation 30

[3-(2-{(2R)-2-[6-(2,5-Dimethyl-pyrrol-1-yl)-pyridin-3-yl]-2-hydroxy-ethylamino}-propyl)-phenyl]-acetic acid

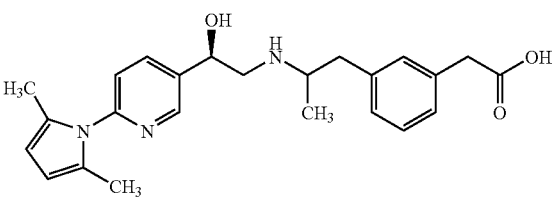

Prepared using the method for preparation 21 using the ester from preparation 31 to give the title compound as a colourless solid which was used without further purification.

$^1$H NMR (400 MHz, DMSO$_{d6}$): δ=8.55 (1H, s), 7.93 (1H, t), 7.35 (1H, d), 7.18-7.15 (1H, m), 7.10-7.03 (3H, m), 5.77 (2H, s), 4.87-4.80 (1H, m), 3.48 (2H, s), 3.01-2.89 (4H, m), 2.50-2.40 (1H, m, partially masked by solvent), 2.01 (6H, s), 0.96 (3H, d) ppm.

LRMS (electrospray): m/z [M+H]$^+$ 408.

Preparation 31

[3-(2-{(2R)-2-[6-(2,5-Dimethyl-pyrrol-1-yl)-pyridin-3-yl]-2-hydroxy-ethylamino}-propyl)-phenyl]-acetic acid methyl ester

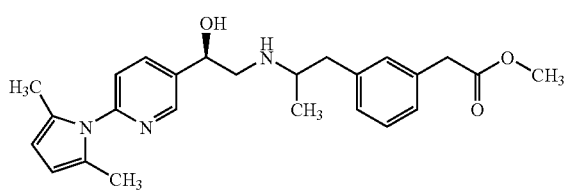

A solution of the amine from preparation 32 (2.0 g, 8.65 mmol), the ketone from preuration 25 (2.14 g, 10.0 mmol), acetic acid (0.5 ml, 8.65 mmol) and sodium triacetoxyborohydride (2.75 g, 13.0 mmol) were stirred in dichloromethane (25 ml) under nitrogen at room temperature for 18 hours. The mixture was washed with water (25 ml) and the aqueous phase extracted with further dichloromethane (2×10 ml). The combined organic extracts were dried (magnesium sulfate), reduced in vacuo and the residue purified by flash column chromatography on silica gel eluting with dichloromethane:methanol:880 ammonia (98:2:0 changing to 95:5:0 then 95:5:0.5, by volume) to give the title compound (1:1 mixture of diastereoisomers) as a pale yellow oil (3.65 g).

¹H NMR (400 MHz, CDCl₃): δ=8.56 (1H, s), 7.87-7.84 (1H, m), 7.30-7.26 (1H, m, partially masked by solvent), 7.20-7.09 (4H, m), 5.88 (2H, s), 4.97-4.87 (1H, m), 3.69 (3H, s), 3.62 (2H, s), 3.18-3.03 (2H, m), 2.94-2.74 (3H, m), 2.10 (6H, s), 1.22 (3H, d) ppm.
LRMS (electrospray): m/z [M+H]⁺ 422.

Preparation 32

(1R)-2-Amino-1-[6-(2,5-dimethyl-pyrrol-1-yl)-pyridin-3-yl]-ethanol

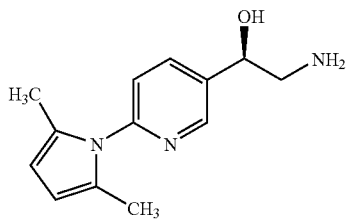

A solution of the phthalimide from preparation 33 (4.85 g, 13.4 mmol) in 8M methylamine in ethanol (50 ml) was stirred under a nitrogen atmosphere at room temperature for 18 hours. The reaction was concentrated under reduced pressure and the residue dissolved in methanol. This solution was passed through a Strong Cation Exchange resin cartridge eluting with methanol and then 2N ammonia in methanol to elute the product. The eluent was concentrated in vacuo and the residue purified by flash column chromatography on silica gel eluting with dichloromethane:methanol:880 ammonia (95:5:0 changing to 90:10:1, by volume) to give the title compound as a pale yellow solid (1.6 g).
¹H NMR (400 MHz, CDCl₃): δ=8.17 (1H, s), 7.85 (1H, d), 7.21 (1H, d), 5.89 (2H, s), 4.69 (1H, t), 3.15-3.11 (1H, dd), 2.85-2.80 (1H, dd), 2.11 (6H, s) ppm.
LRMS (electrospray): m/z [M+H]⁺ 232, [M+Na]⁺, 254.

Preparation 33

2-{(2R)-2-[6-(2,5-Dimethyl-pyrrol-1-yl)-pyridin-3-yl]-2-hydroxy-ethyl}-isoindole-1,3-dione

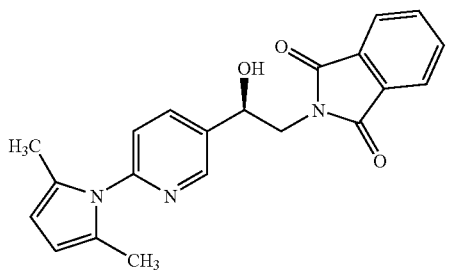

A solution of the crude epoxide from preparation 27 (30.0 g of 65% b/w epoxide, 19.50 g, 91.0 mmol), phthalimide (12.51 g, 85.0 mmol) and potassium phthalimide (2.78 g, 15.0 mmol) in N,N-dimethylformamide (200 ml) was heated at 90° C. under nitrogen for 6 hours. After cooling the reaction was stirred at room temperature for 18 hours, concentrated in vacuo and the residue partitioned between dichloromethane (600 ml) and water (400 ml). The organic phase was separated and the aqueous phase extracted with further dichloromethane (200 ml). The combined organic extracts were dried (magnesium sulfate) and concentrated in vacuo. Crystallisation from ethyl acetate (300 ml) gave the title compound as a pale yellow crystalline solid (22.1 g).
¹H NMR (400 MHz, DMSO-d₆): δ=8.42 (1H, s), 7.90 (1H, d), 7.80 (4H, d), 7.30 (1H, d), 5.90 (1H, s), 5.80 (2H, s), 5.00 (1H, brs), 3.82 (1H, m), 3.75 (1H, m), 1.95 (6H, s) ppm.
LRMS (electrospray): m/z [M+H]⁺ 362.

Preparation 34

[3-(2-{(2R)-2-[6-(2,5-Dimethyl-pyrrol-1-yl)-pyridin-3-yl]-2-hydroxy-ethylamino}-2-methyl-propyl)-phenyl]-acetic acid

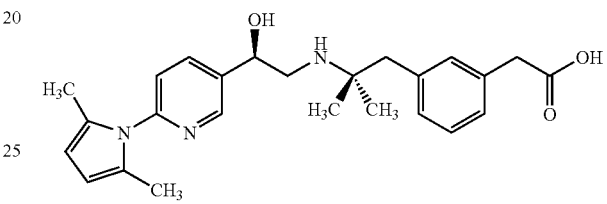

Prepared according to the method described for preparation 21 using the ester from preparation 35 to give the title compound as a colourless solid.
¹H NMR (400 MHz, CD₃OD): δ=8.66 (1H, s), 8.13-8.10 (1H, m), 7.39 (1H, d), 7.31-7.23 (3H, m), 7.14-7.12 (1H, m), 5.83 (2H, s), 5.11-5.07 (1H, m), 3.55 (2H, s), 3.42-3.23 (2H, m), 3.04-2.97 (2H, m), 2.05 (6H, s), 1.37 (3H, s), 1.36 (3H, s) ppm.
LRMS (electrospray): m/z [M+H]⁺ 422, [M+Na]⁺ 444, [M−H]⁻ 420.

Preparation 35

[3-(2-{(2R)-2-[6-(2,5-Dimethyl-pyrrol-1-yl)-pyridin-3-yl]-2-hydroxy-ethylamino}-2-methyl-propyl)-phenyl]-acetic acid ethyl ester

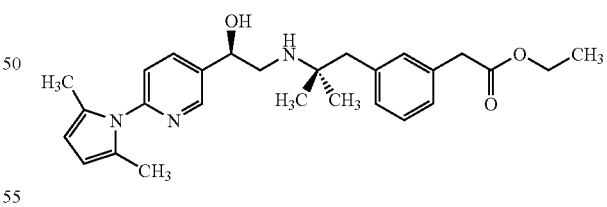

Prepared according to the method described for preparation 22 using the epoxide from preparation 27 and the amine from preparation 45 to give the title compound as a pale yellow oil.
¹H NMR (400 MHz, CD₃OD): δ=8.58 (1H, s), 8.04-8.01 (1H, m), 7.32 (1H, d), 7.24 (1H, t), 7.17-7.11 (3H, m), 5.82 (2H, s), 4.13 (2H, q), 3.62 (2H, s), 2.95-2.85 (2H, m), 2.80-2.67 (2H, dd), 2.04 (6H, s), 1.22 (3H, t), 1.09 (3H, s), 1.06 (3H, s) ppm.
LRMS (electrospray): m/z [M+H]⁺ 450, [M+Na]⁺ 472, [M−H]⁻ 448.

Preparation 36

[4-(2-{(2R)-2-[6-(2,5-Dimethyl-pyrrol-1-yl)-pyridin-3-yl]-2-hydroxy-ethylamino}-2-methyl-propyl)-phenyl]-acetic acid

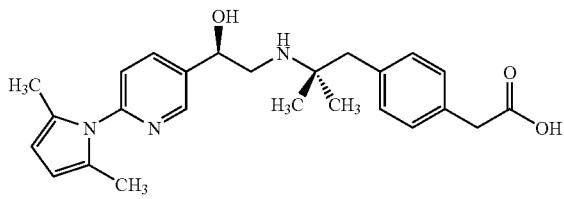

Prepared according to the method described for preparation 21 using the ester from preparation 37 to give the title compound as a pale yellow solid.

$^1$H NMR (400 MHz, DMSO$_{d6}$): δ=8.56 (1H, s), 7.93 (1H, d), 7.32 (1H, d), 7.14-7.06 (4H, m), 5.77 (2H, s), 4.72 (1H, m), 3.46 (2H, s), 2.83-2.82 (2H, m), 2.60 (2H, s), 2.01 (6H, s), 0.95 (3H, s), 0.93 (3H, s) ppm.

LRMS (electrospray): m/z [M+H]$^+$ 422, [M−H]$^−$ 420.

Preparation 37

[4-(2-{(2R)-2-[6-(2,5-Dimethyl-pyrrol-1-yl)-pyridin-3-yl]-2-hydroxy-ethylamino}-2-methyl-propyl)-phenyl]-acetic acid methyl ester

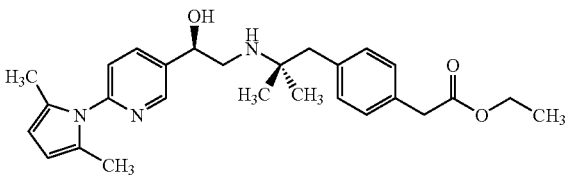

Prepared according to the method described for preparation 22 using the epoxide from preparation 27 and the amine from preparation 38 to give the title compound as a pale yellow oil.

$^1$H NMR (400 MHz, CDCl$_3$): δ=8.58 (1H, s), 7.82 (1H, d), 7.20 (3H, m), 7.15 (2H, m), 5.80 (2H, s), 4.70 (1H, m), 4.17 (2H, q), 3.59 (2H, s), 3.05 (1H, m), 2.75-2.65 (3H, m), 2.10 (6H, s), 1.25 (3H, t), 1.18 (3H, s), 1.17 (3H, s) ppm.

LRMS (electrospray): m/z [M+H]$^+$ 450, [M+Na]$^+$ 472, [M−H]$^−$ 448.

Preparation 38

[4-(2-Amino-2-methyl-propyl)-phenyl]-acetic acid ethyl ester

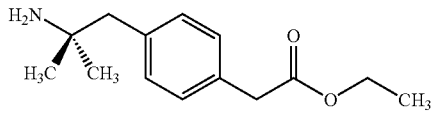

A solution of the ester from preparation 39 (1.99 g, 5.44 mmol) was treated with a solution of methylamine in ethanol (10 ml of 8M solution, 80 mmol) and the resulting solution left to stir at room temperature. After 3 hours the solvent was removed in vacuo and the residue triturated with methanol to give N-[1,1-dimethyl-2-(4-methylcarbamoylmethyl-phenyl)-ethyl]-N'-methyl-phthalimide as a colourless solid. The solid was treated with hydrochloric acid (100 ml of 6N solution) and heated to 100° C. for 48 hours. The solvent was removed in vacuo and the crude amino-acid residue treated with a mixture of ethanol (50 ml) and concentrated sulphuric acid (2 ml) at room temperature for 16 hours. The solvent was removed in vacuo and the residue partitioned between dichloromethane (100 ml) and saturated aqueous potassium carbonate (100 ml). The organic phase was separated, dried (sodium sulfate) and the solvent removed in vacuo to give the title compound as a pale yellow oil (760 mg, 59%).

$^1$H NMR (400 MHz, CDCl$_3$): δ=7.22 (2H, d), 7.15 (2H, d), 4.17 (2H, q), 3.60 (2H, s), 2.61 (2H, s), 1.25 (3H, t), 1.10 (6H, s) ppm.

LRMS (electrospray): m/z [M+H]$^+$ 236.

Preparation 39

{4-[2-(1,3-Dioxo-1,3-dihydro-isoindol-2-yl)-2-methyl-propyl]-phenyl}-acetic acid ethyl ester

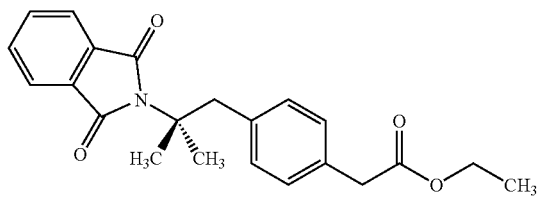

A solution of the boronic acid ester from preparation 40 (3.32 g, 8.19 mmol) in tetrahydrofuran (35 ml) was treated with ethyl bromoacetate (0.75 ml, 6.8 mmol), palladium(II) acetate (46 mg, 0.20 mmol), tri-ortho-tolylphosphine (187 mg, 0.61 mmol), and potassium phosphate (7.24 g, 34 mmol) and the resulting suspension stirred at room temperature under a nitrogen atmosphere for 16 hours. The reaction mixture was diluted with dichloromethane (150 ml), washed with water (100 ml), saturated aqueous sodium chloride (100 ml), dried (sodium sulfate) and reduced in vacuo to give the title compound as an orange oil (1.85 g, 74%).

$^1$H NMR (400 MHz, CDCl$_3$): δ=7.77 (2H, m), 7.70 (2H, m), 7.12 (2H, d), (7.06 (2H, d), 4.12 (2H, q), 3.54 (2H, s), 3.26 (2H, s), 1.75 (6H, s), 1.23 (3H, t) ppm.

LRMS (electrospray): m/z [M+H]$^+$ 366, [M+Na]$^+$ 388.

Preparation 40

2-{1,1-Dimethyl-2-[4-(4,4,5,5-tetramethyl-[1,3,2]dioxaborolan-2-yl)-phenyl]-ethyl}-isoindole-1,3-dione

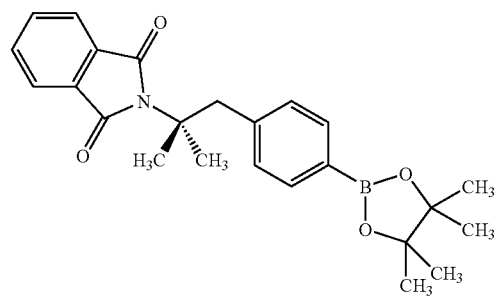

A solution of the bromide from preparation 41 (6.88 g, 19 mmol), potassium acetate (5.65 g, 57 mmol), bis(pinacolato)diboron (5.85 g, 23 mmol) and [1,1'-bis(diphenylphosphino)ferrocene]palladium(II)chloride (0.80 g, 0.98 mmol) in dimethylsulfoxide (100 ml) was heated at 80° C. under a nitrogen atmosphere for 16 hours. The reaction mixture was cooled to room temperature, diluted with water (300 ml) and extracted with ethyl acetate (3×100 ml). The combined organic extracts were washed with water (100 ml) saturated aqueous sodium chloride (100 ml), dried (sodium sulfate) and reduced in vacuo. Purification by flash column chromatography on silica gel eluting with pentane:dichloromethane (60:40 changing to 0:100, by volume) to give the title compound as a colourless oil (5.58 g, 72%).

$^1$H NMR (400 MHz, CDCl$_3$): δ=7.73 (2H, m), 7.68 (2H, m), 7.60 (2H, d), 7.08 (2H, d), 3.27 (2H, s), 1.74 (6H, s), 1.30 (12H, s) ppm.

Preparation 41

2-[2-(4-Bromo-phenyl)-1,1-dimethyl-ethyl]-isoindole-1,3-dione

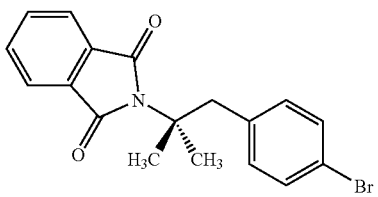

A solution of the amine from preparation 42 (5.13 g, 22 mmol), carboethoxyphthalimide (5.91 g, 27 mmol) and triethylamine (7.52 ml, 54 mmol) in toluene (80 ml) was heated at 110° C. under a nitrogen atmosphere for 16 hours. The reaction mixture was cooled to room temperature and the solvent reduced in vacuo. The residue was partitioned between dichloromethane (100 ml) and saturated sodium bicarbonate (100 ml). The organic phase was separated, dried (sodium sulfate) and reduced in vacuo. Purification by flash column chromatography on silica gel eluting with pentane:dichloromethane (60:40 changing to 0:100, by volume) gave the title compound as a colourless oil (5.14 g, 64%).

$^1$H NMR (400 MHz, CDCl$_3$): δ=7.78 (2H, m), 7.65 (2H, m), 7.25 (2H, d), 6.98 (2H, d), 3.20 (2H, s), 1.75 (6H, s) ppm.

LRMS (electrospray): m/z [M+H]$^+$ 359, [M+NH$_4$]$^+$ 376.

Preparation 42

2-(4-Bromo-phenyl)-1,1-dimethyl-ethylamine

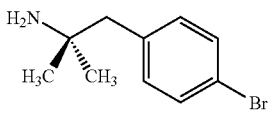

A solution of the amide from preparation 43 (19.0 g, 62 mmol), thiourea (5.70 g, 75 mmol) and acetic acid (30 ml) in ethanol (150 ml) was heated to reflux under a nitrogen atmosphere for 16 hours. The reaction mixture was cooled to room temperature and filtered washing the solid precipitate with ethanol (50 ml). The filtrate was reduced in vacuo and the residue partitioned between dichloromethane (500 ml) and 1M aqueous sodium hydroxide (300 ml). The organic phase was separated and the aqueous extracted with dichloromethane (500 ml). The combined organic extracts were washed with saturated aqueous sodium chloride (200 ml), dried (sodium sulfate) and the solvent removed in vacuo to give the title compound as a dark orange oil (12.58 g, 88%).

$^1$H NMR (400 MHz, CDCl$_3$): δ=7.41 (2H, d), 7.05 (2H, d), 2.60 (2H, s), 1.08 (6H, s) ppm.

LRMS (electrospray): m/z [M+H]$^+$ 228/230.

Preparation 43

N-[2-(4-Bromo-phenyl)-1,1-dimethyl-ethyl]-2-chloro-acetamide

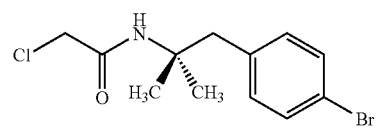

2-Chloroacetonitrile (8.8 ml, 140 mmol) was added to a solution of the alcohol from preparation 44 (16.0 g, 70 mmol), in acetic acid (33 ml). The resulting solution was cooled to 0° C. and treated with concentrated sulphuric acid (33 ml) maintaining an internal temperature <10° C. The reaction mixture was then allowed to warm gradually to room temperature. After 4 hours the reaction mixture was poured onto ice and basified with solid sodium carbonate. The solution was extracted with ethyl acetate (2×500 ml) and the combined organic extracts dried (sodium sulfate) and reduced in vacuo to give the title compound as a colourless solid (19.0 g, 89%).

$^1$H NMR (400 MHz, CDCl$_3$): δ=7.41 (2H, d), 7.00 (2H, d), 6.18 (1H, s), 3.95 (2H, s), 3.02 (2H, s), 1.35 (6H, s) ppm.

LRMS (electrospray): m/z [M+H]$^+$ 304/306.

Preparation 44

1-(4-Bromo-phenyl)-2-methyl-propan-2-ol

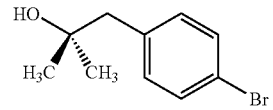

A solution of 4-bromophenylacteone (6.85 g, 32 mmol) in diethyl-ether (100 ml) was cooled to 0° C. and treated with methylmagnesium bromide (23.5 ml of a 3M solution in diethyl-ether, 70 mmol). The reaction mixture was allowed to warm gradually to room temperature. After 2 hours the reaction was quenched by addition of saturated aqueous ammonium chloride (200 ml). The organic phase was separated and washed with saturated sodium chloride (100 ml), dried (sodium sulfate) and reduced in vacuo. Purification by flash column chromatography on silica gel eluting with pentane:dichloromethane (60:40 changing to 0:100, by volume) gave the title compound as a colourless oil (6.23 g, 84%).

$^1$H NMR (400 MHz, CDCl$_3$): δ=7.42 (2H, d), 7.10 (2H, d), 2.70 (2H, s), 1.22 (6H, s) ppm.

Preparation 45

[3-(2-Amino-2-methyl-propyl)-phenyl]-acetic acid ethyl ester

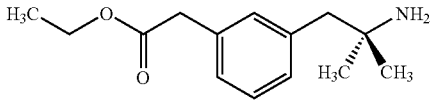

A solution of the amide from preparation 46 (5.1 g, 18 mmol), thiourea (1.6 g, 21 mmol) and acetic acid (18 ml) in ethanol (80 ml) was heated to reflux under a nitrogen atmosphere for 16 hours. The reaction mixture was cooled and filtered. The filtrate was reduced in vacuo, the residue dissolved in ethanol (150 ml), saturated with hydrogen chloride gas and the resulting solution heated to reflux for 16 hours. The solvent was reduced in vacuo and the residue partitioned between ethyl acetate (200 ml) and 5% aqueous sodium carbonate (200 ml). The organic extract was washed with saturated sodium chloride (100 ml), dried (sodium sulfate) and reduced in vacuo. The residue was purified by strong cation exchange resin, eluting with methanol and then 2N ammonia in methanol to elute the product. The eluent was concentrated in vacuo giving the title compound as a yellow oil (2.68 g, 63%).

$^1$H NMR (400 MHz, CDCl$_3$): δ=7.29-7.04 (4H, m), 4.08 (2H, q), 3.64 (2H, s), 2.57 (2H, s), 1.18 (3H, t), 0.99 (6H, s) ppm.

LRMS (electrospray): m/z [M+H]$^+$ 236, [M+NH$_4$]$^+$ 258.

Preparation 46

{3-[2-(2-Chloro-acetylamino)-2-methyl-propyl]-phenyl}-acetic acid

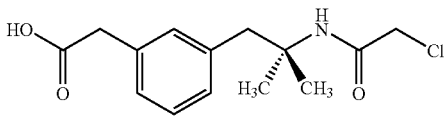

Prepared using the method for preparation 43 using the alcohol from preparation 47 as starting material to give the title compound as a colourless solid.

$^1$H NMR (400 MHz, CDCl$_3$): δ=7.31-7.06 (4H, m), 6.19 (1H, bs), 3.95 (2H, s), 3.62 (2H, s), 3.02 (2H, s), 1.36 (6H, s) ppm.

LRMS (electrospray): m/z [M−H]$^−$ 282/284.

Preparation 47

[3-(2-Hydroxy-2-methyl-propyl)-phenyl]-acetic acid

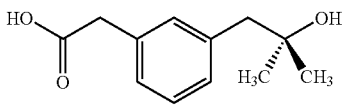

Prepared according to the method for preparation 44 using (3-ethoxycarbonylmethyl-phenyl)-acetic acid as starting material to give the title compound as a pale yellow oil.

$^1$H NMR (400 MHz, CDCl$_3$): δ=7.30-7.12 (4H, m), 3.63 (2H, s), 2.75 (2H, s), 1.22 (6H, s) ppm.

LRMS (electrospray): m/z [M+H]$^+$ 209.

Preparation 48

2-[3-(2-{(2R)-2-[6-(2,5-Dimethylpyrrol-1-yl)pyridin-3-yl]-2-hydrox-ethylamino}-2-methylpropyl)phenyl]-N-(4'-hydroxybiphenyl-3-ylmethyl)acetamide

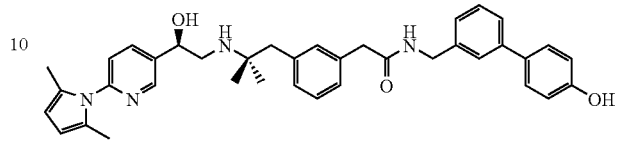

Prepared according to the method described for preparation 1 using the acid from preparation 34 and the amine from preparation 73 to give the title compound as an amber coloured oil.

$^1$H NMR (400 MHz, CD$_3$OD): δ=8.54 (1H, d), 7.97 (1H, d), 7.35-7.38 (2H, m), 7.27-7.32 (2H, m), 7.24-7.25 (2H, m), 7.17-7.22 (3H, m), 7.08-7.12 (2H, m), 6.78-6.80 (2H, m), 5.81 (2H, s), 4.78 (1H, dd), 4.40 (2H, s), 3.55 (2H, s), 2.80-2.90 (2H, m), 2.60 (2H, dd), 2.03 (6H, s), 1.03 (3H, s), 1.00 (3H, s) ppm.

LRMS (electrospray): m/z [M+H]$^+$ 603, [M+Na]$^+$ 625.

Preparation 49

2-[3-(2-{(2R)-2-[6-(2,5-Dimethylpyrrol-1-yl)pyridin-3-yl]-2-hydrox-ethylamino}-2-methylpropyl)phenyl]-N-(4'-hydroxybiphenyl-4-ylmethyl)acetamide

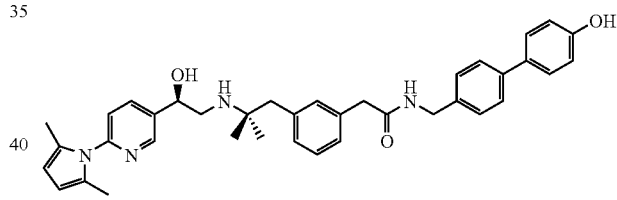

Prepared according to the method described for preparation 1 using the acid from preparation 34 and the amine from preparation 82 to give the title compound as an amber coloured oil.

$^1$H NMR (400 MHz, CD$_3$OD): δ=8.56 (1H, d), 7.98 (1H, dd), 7.39-7.47 (4H, m), 7.23-7.31 (4H, m), 7.18-7.19 (2H, m), 7.11-7.13 (1H, m), 6.81-6.84 (2H, m), 5.82 (2H, s), 4.80 (1H, dd), 4.88 (2H, s), 3.65 (2H, s), 2.83-2.95 (2H, m), 2.66 (2H, dd), 2.03 (6H, s), 1.06 (3H, s), 1.03 (3H, s) ppm.

LRMS (electrospray): m/z [M+H]$^+$ 603, [M+Na]$^+$ 625.

Preparation 50

2-[3-((2R)-2-{(2R)-2-[6-(2,5-Dimethylpyrrol-1-yl)pyridin-3-yl]-2-hydroxyethylamino}propyl)-phenyl]-N-(4'-hydroxybiphenyl-3-ylmethyl)acetamide

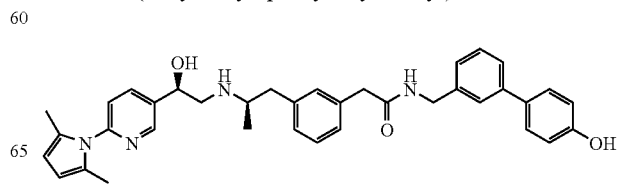

Prepared according to the method described for preparation 1 using the acid from preparation 21 and the amine from preparation 73 to give the title compound as an amber coloured oil.

$^1$H NMR (400 MHz, CD$_3$OD): δ=8.49 (1H, d), 7.90 (1H, dd), 7.38-7.40 (1H, m), 7.31-7.35 (3H, m), 7.22-7.29 (3H, m), 7.17-7.19 (2H, m), 7.06-7.13 (2H, m), 6.80-6.82 (2H, m), 5.81 (2H, s), 4.78 (1H, dd), 4.40 (2H, s), 3.55 (2H, s), 2.92 (1H, dd), 2.81-2.83 (2H, m), 2.70 (1H, dd), 2.52-2.57 (1H, m), 2.02 (6H, s), 1.02 (3H, s) ppm.

LRMS (electrospray): m/z [M+H]$^+$ 589, [M+Na]$^+$ 611.

Preparation 51

2-[3-((2R)-2-{(2R)-2-[6-(2,5-Dimethylpyrrol-1-yl)pyridin-3-yl]-2-hydroxyethylamino}propyl)phenyl]-N-(4-hydroxynaphthalen-1-ylmethyl)acetamide

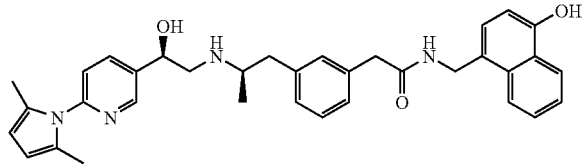

Prepared according to the method described for preparation 1 using the acid from preparation 21 and the amine from preparation 79 to give the title compound as a light brown foam.

$^1$H NMR (400 MHz, CD$_3$OD): δ=8.47 (1H, d), 8.20-8.23 (1H, m), 7.91 (1H, dd), 7.84-7.86 (1H, m), 7.05-7.12 (2H, m), 6.71 (1H, d), 5.81 (2H, s), 4.79 (1H, dd), 4.70 (2H, s), 2.68-2.91 (6H, m), 2.02 (6H, s), 1.01 (3H, d) ppm.

LRMS (electrospray): m/z [M+H]$^+$ 563, [M+Na]$^+$ 585.

Preparation 52

3-(2-{(2R)-2-[6-(2,5-Dimethylpyrrol-1-yl)pyridin-3-yl]-2-hydroxyethylamino}-2-methylpropyl)-N-(4'-hydroxybiphenyl-3-ylmethyl)benzamide

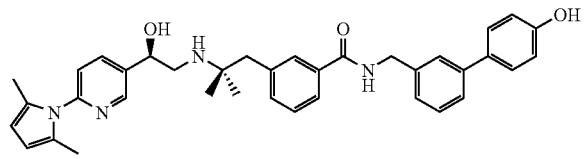

Prepared according to the method described for preparation 1 using the acid from preparation 60 and the amine from preparation 73 to give the title compound as a colourless solid.

$^1$H NMR (400 MHz, CD$_3$OD): δ=8.59 (1H, d), 8.00 (1H, dd), 7.77-7.80 (2H, m), 7.53-7.56 (1H, m), 7.40-7.45 (5H, m), 7.33 (1H, t), 7.24-7.28 (2H, m), 6.80-6.84 (2H, m), 5.82 (2H, s), 4.95 (1H, t), 4.58 (2H, dd), 3.12 (2H, d), 2.89 (2H, dd), 2.02 (6H, s), 1.2 (3H, s), 1.19 (3H, s) ppm.

LRMS (electrospray): m/z [M+H]$^+$ 589, [M+Na]$^+$ 611.

Preparation 53

3-(2-{(2R)-2-[6-(2,5-Dimethylpyrrol-1-yl)pyridin-3-yl]-2-hydroxy-ethylamino}-2-methylpropyl)-N-[2-(4-hydroxyphenyl)-2-methylpropyl]benzamide

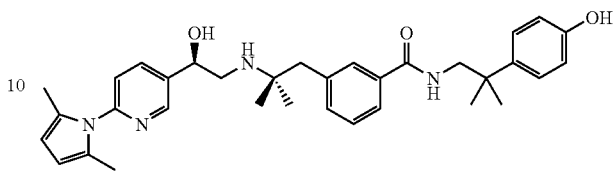

Prepared according to the method described for preparation 1 using the acid from preparation 60 and the amine from preparation 76 to give the title compound as a light brown foam.

$^1$H NMR (400 MHz, CD$_3$OD): δ=8.65 (1H, d), 8.10 (1H, dd), 7.57-7.61 (2H, m), 7.38-7.44 (3H, m), 7.24-7.28 (2H, m), 6.72-6.76 (2H, m), 5.83 (2H, s), 5.03 (1H, dd), 3.52 (2H, s), 3.22-3.28 (2H, m), 3.02 (2H, s), 2.05 (6H, s), 1.84 (6H, s), 1.28 (3H, s), 1.31 (3H, s) ppm.

LRMS (electrospray): m/z [M+H]$^+$ 555, [M+Na]$^+$ 577.

Preparation 54

3-(2-{(2R)-2-[6-(2,5-Dimethyl-pyrrol-1-yl)pyridin-3-yl]-2-hydroxyethyl-amino}-2-methylpropyl)-N-[2-(4-hydroxy-2,5-dimethylphenyl)ethyl]benzamide

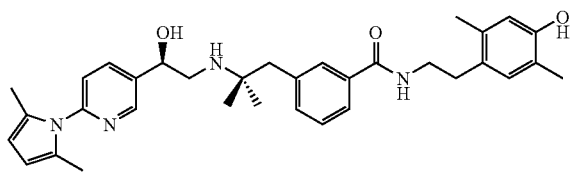

Prepared according to the method described for preparation 1 using the acid from preparation 60 and the amine from preparation 86 to give the title compound as a colourless solid.

$^1$H NMR (400 MHz, CD$_3$OD): δ=8.59 (1H, d), 8.62 (1H, dd), 7.65-7.68 (2H, m), 7.38-7.40 (2H, m), 7.32 (1H, d), 6.84 (1H, s), 6.54 (1H, s), 5.81 (2H, s), 3.45 (2H, s), 3.45 (2H, dt), 2.96 (1H, dd), 2.88-2.91 (2H, m), 2.73-2.81 (3H, m), 2.23 (3H, s), 2.08 (3H, s), 2.03 (3H, s), 1.12 (3H, s), 1.06 (3H, s) ppm.

LRMS (electrospray): m/z [M+H]$^+$ 555, [M+Na]$^+$ 577.

Preparation 55

3-(2-{(2R)-2-[6-(2,5-Dimethylpyrrol-1-yl)pyridin-3-yl]-2-hydroxy-ethylamino}-2-methylpropyl)-N-[2-(4-hydroxy-2,3-dimethylphenyl)ethyl]benzamide

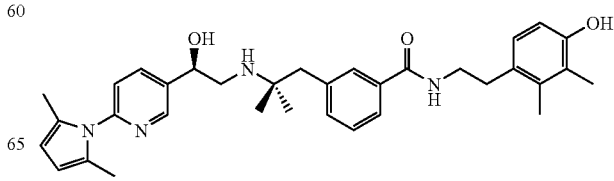

Prepared according to the method described for preparation 1 using the acid from preparation 60 and the amine from preparation 87 to give the title compound as a straw coloured foam.

$^1$H NMR (400 MHz, CD$_3$OD): δ=1.06 (3H, s), 1.13 (3H, s), 2.04 (6H, s), 2.11 (3H, s), 2.24 (3H, s), 2.73 (1H, d), 2.83-2.92 (4H, m), 2.97-3.02 (1H, m), 3.46-3.49 (2H, m), 4.84 (1H, m, partially obscured by solvent peak), 2.82 (2H, s), 6.53 (1H, d), 6.80 (1H, d), 7.82 (1H, d), 7.38-7.41 (2H, m), 7.65-7.68 (2H, m), 8.03 (1H, dd), 8.59 (1H, s) ppm.

LRMS (APCl): m/z [M+H]$^+$ 555.

Preparation 56

3-(2-{(2R)-2-[6-(2,5-Dimethylpyrrol-1-yl)pyridin-3-yl]-2-hydroxy-ethylamino}-2-methylpropyl)-N-[2-(4-hydroxy-3-methylphenyl)ethyl]benzamide

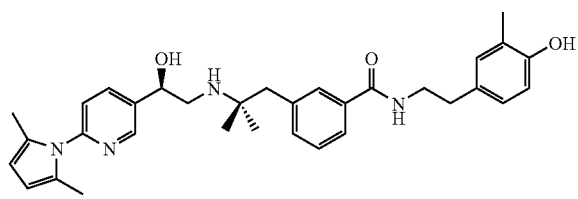

Prepared according to the method described for preparation 1 using the acid from preparation 60 and the amine from preparation 86 to give the title compound as a beige foam.

$^1$H NMR (400 MHz, CDCl$_3$): δ=1.04 (3H, s), 1.12 (3H, s), 2.12 (9H, s), 2.62 (1H, d), 2.73-2.87 (4H, m), 2.95 (1H, d), 3.52-3.58 (1H, m), 3.74-3.81 (1H, m), 4.64 (1H, d), 5.89 (2H, s), 6.48 (1H, bs), 6.63 (1H, d), 6.86 (1H, d), 6.95 (1H, s), 7.20 (1H, d), 7.33 (1H, t), 7.48 (1H, s), 7.60 (1H,d), 7.81 (1H, d), 8.53 (1H, s) ppm.

LRMS (APCl): m/z [M+H]$^+$ 541, [M−H]$^-$ 539.

Preparation 57

3-((2R)-2-{(2R)-2-[6-(2,5-Dimethylpyrrol-1-yl)-pyridin-3-yl]-2-hydroxyethylamino}propyl)-N-[2-(4-hydroxy-2,5-dimethylphenyl)ethyl]benzamide

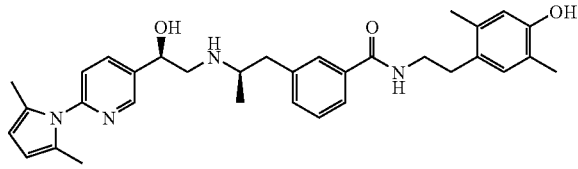

Prepared according to the method described for preparation 1 using the acid from preparation 68 and the amine from preparation 86 to give the title compound as a colourless solid.

$^1$H NMR (400 MHz, CD$_3$OD): δ=8.53 (1H, d), 7.96 (1H, dd), 7.87-7.88 (2H, m), 7.60-7.63 (2H, m), 7.29 (1H, d), 6.85 (1H, s), 6.54 (1H, s), 5.81 (2H, s), 4.84-4.85 (1H, m), 3.45 (2H, t), 3.02 (1H, dd), 2.86-2.92 (3H, m), 2.77-2.81 (2H, m), 2.626-2.67 (1H, m), 2.23 (3H, s), 2.09 (3H, s), 2.03 (6H, s), 1.08 (3H, d) ppm.

LRMS (electrospray): m/z [M+H]$^+$ 541, [M+Na]$^+$ 563.

Preparation 58

3-((2R)-2-{(2R)-2-[6-(2,5-Dimethylpyrrol-1-yl)-pyridin-3-yl]-2-hydroxyethylamino}propyl)-N-[2-(4-hydroxy-2,3-dimethylphenyl)ethyl]benzamide

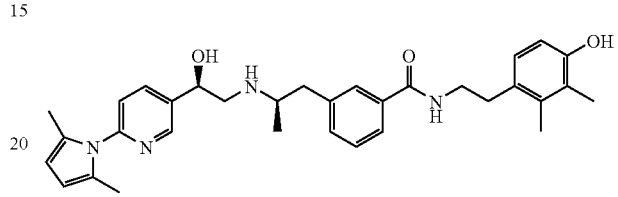

Prepared according to the method described for preparation 1 using the acid from preparation 68 and the amine from preparation 87 to give the title compound as a straw coloured foam.

$^1$H NMR (400 MHz, CD$_3$OD): δ=1.09 (3H, s), 1.10 (3H, s), 2.03 (6H, s), 2.12 (3H, s), 2.25 (3H, s), 2.62 (1H, dd), 2.83-2.94 (5H, m), 3.02-3.07 (1H, m), 3.45-3.48 (2H, m), 4.85 (1H, m, partially obscured by solvent peak), 5.81 (2H, s), 6.53 (1H, d), 6.80 (1H, d), 7.29 (1H, d), 7.86-7.89 (2H, m), 7.60-7.64 (2H, m), 7.96 (1H, dd), 8.52 (1H, d) ppm.

LRMS (electrospray): m/z [M+H]$^+$ 541, [M+Na]$^+$ 563.

Preparation 59

3-((2R)-2-{(2R)-2-[6-(2,5-Dimethylpyrrol-1-yl)-pyridin-3-yl]-2-hydroxyethylamino}propyl)-N-[2-(4-hydroxy-3-methylphenyl)ethyl]benzamide

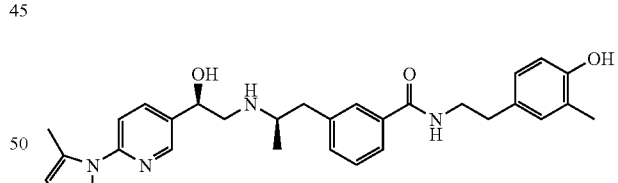

Prepared according to the method described for preparation 1 using the acid from preparation 68 and the amine from preparation 88 to give the title compound as a light beige foam.

$^1$H NMR (400 MHz, CD$_3$OD): δ=1.12 (3H, d), 2.09 (6H, s), 2.20 (3H, s), 2.67-2.73 (3H, m), 2.79 (2H, t), 2.94-3.02 (2H, m), 3.59-3.70 (2H, m), 4.59 (1H, dd), 5.88 (1H, s), 6.21 (1H, t), 6.67 (1H, d), 6.88 (1H, dd), 6.97 (1H, d), 7.18 (1H, d), 7.28-7.36 (2H, m), 7.49-7.52 (2H, m), 7.80 (1H, dd), 7.48 (1H, d) ppm.

LRMS (APCl): m/z [M+H]$^+$ 527, [M−H]$^-$ 525.

Preparation 60

3-(2-{(2R)-2-[6-(2,5-Dimethylpyrrol-1-yl)pyridin-3-yl]-2-hydroxyethylamino}-2-methylpropyl)benzoic acid

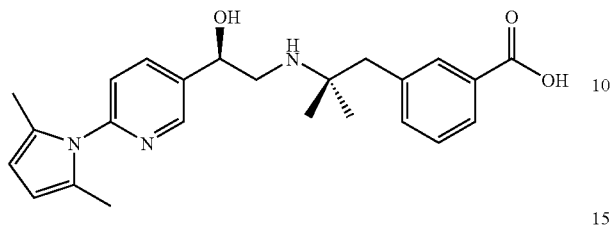

Prepared according to the method described for preparation 21 using preparation 61 to give the title compound as a cream coloured powder.

$^1$H NMR (400 MHz, CD$_3$OD): δ=8.67 (1H, d), 8.13 (1H, d), 7.94 (1H, d), 7.87-7.92 (2H, m), 7.40-7.47 (3H, m), 5.83 (2H, s), 5.08 (1H, dd), 3.43 (1H, dd), 3.32 (1H, dd), 3.10 (2H, d), 2.06 (6H, s), 1.35 (6H, s) ppm.

LRMS (APCl): m/z [M+H]$^+$ 408, [M–H]$^-$ 406.

Preparation 61

3-(2-{(2R)-2-[6-(2,5-Dimethylpyrrol-1-yl)pyridin-3-yl]-2-hydroxyethylamino}-2-methylpropyl)-benzoic acid methyl ester

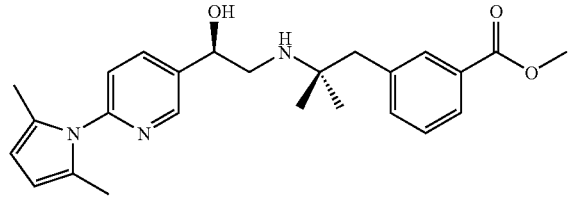

Prepared according to the method described for preparation 22 using the amine from preparation 62 and the epoxide from preparation 27 to give the title compound as a brown oil.

$^1$H NMR (400 MHz, CD$_3$OD): δ=8.57 (1H, d), 7.86-7.93 (3H, m), 7.36-7.38 (2H, m), 7.20 (1H, d), 5.89 (2H, s), 4.65 (1H, d), 3.91 (3H, s), 3.05 (1H, d), 2.76 (2H, d), 2.67 (1H, dd), 2.11 (6H, s), 1.11 (6H, s) ppm.

LRMS (APCl): m/z [M+H]$^+$ 422.

Preparation 62

3-(2-amino-2-methylpropyl)benzoic acid methyl ester

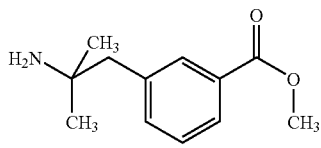

A solution of preparation 63 (1.6 g, 5.2 mmol) in dichloromethane (160 ml) at 0° C. was treated with trifluoroacetic acid (13.6 ml) and left to warm to room temperature over 2 hours. The solvent was removed in vacuo and the product purified by cation exchange chromatography (methanol followed by 2M ammonia in methanol) to yield the title compound as an amber oil (1.06 g).

$^1$H NMR (400 MHz, CDCl$_3$) δ=7.90-7.88 (1H, m), 7.84 (1H, s), 7.36-7.35 (2H, m), 3.90 (3H, s), 2.71 (2H, s), 1.67 (2H, bs), 1.12 (6H, s).

LRMS (electrospray) m/z 208 [M+H]$^+$

Preparation 63

3-(2-tert-butoxycarbonylamino-2-methylpropyl)benzoic acid methyl ester

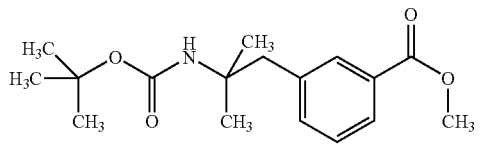

A solution of preparation 64 (7.0 g, 21 mmol), [1,1'-bis(diphenylphosphino)ferrocene]dichloropalladium(II) (1.74 g, 2.1 mmol) and triethylamine (5.94 ml, 43 mmol) in methanol (250 ml) was heated to 100° C. under 100 psi carbon monoxide for 12 hours. The reaction mixture was filtered through arbocel and the filtrate concentrated in vacuo and purified by flash column chromatography on silica gel eluting with dichloromethane:pentane (50:50 by volume) to afford the title compound as a yellow solid (3.76 g).

$^1$H NMR (400 MHz, CDCl$_3$) □=7.92-7.90 (1H, m), 7.82 (1H, s), 7.35-7.34 (2H, m), 4.24 (1H, bs), 3.90 (3H, s), 3.05 (2H, s), 1.48 (9H, s), 1.26 (6H, s).

LRMS (electrospray) m/z 208 [M+H–BOC]$^+$

Preparation 64

[2-(3-bromophenyl)-1,1-dimethylethyl]carbamic acid tert-butyl ester

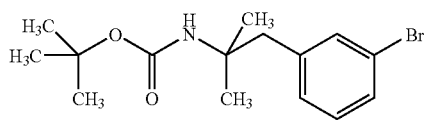

Preparation 65 (5.0 g, 22 mmol) was treated with di-tert-butyl dicarbonate (5.26 g, 24 mmol) in dichloromethane (50 ml) and stirred for 20 hours. The reaction mixture was washed with water (50 ml) and the combined organics dried (sodium sulfate) and the solvent removed in vacuo. The crude material was purified using a cation exchange column (methanol followed by 2M ammonia in methanol), followed by purification by flash column chromatography on silica gel eluting with dichloromethane to afford the title compound as a brown oil (7.23 g).

$^1$H NMR (400 MHz, CDCl$_3$) δ=7.35 (1H, d), 7.30 (1H, s), 7.15-7.11 (1H, t), 7.05 (1H, d), 4.24 (1H, bs), 2.97 (2H, s), 1.50 (9H, s), 1.27 (6H, s).

LRMS (electrospray) m/z 350 [M+NH$_4$]$^+$

Preparation 65

2-(3-bromophenyl)-1,1-dimethylethylamine

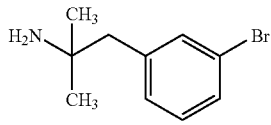

A solution of preparation 66 (32.0 g, 105 mmol), thiourea (9.60 g, 126 mmol) and acetic acid (50 ml) in ethanol (250 ml) was heated to reflux overnight. The reaction mixture was cooled to room temperature and filtered, the filtrate was concentrated in vacuo and basified using aqueous sodium hydroxide solution (1M, 450 ml). The product was extracted with dichloromethane (2×500 ml) and the combined organics washed with brine (50 ml), dried (sodium sulfate) and the solvent removed in vacuo to afford the title compound as a black oil (23 g).

$^1$H NMR (400 MHz, CDCl$_3$) δ=7.36-7.32 (2H, m), 7.16-7.08 (2H, m), 2.62 (2H, s), 1.84 (2H, bs), 1.12 (6H, s).

LRMS (electrospray) m/z 228 [M+H]$^+$

Preparation 66

N-[2-(3-bromophenyl)-1,1-dimethylethyl]-2-chloro-acetamide

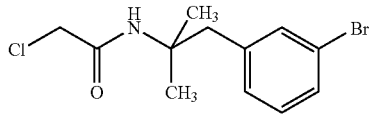

Chloroacetonitrile (6.63 ml, 105 mmol) was added to a stirred solution of preparation 67 (12.0 g, 52.0 mmol) in acetic acid (25 ml) at room temperature. The resulting solution was cooled to 0° C. and concentrated sulfuric acid (25 ml) was added keeping the temperature <10° C. The resulting solution was left to stir for 1 hour and then poured onto ice and basified by the addition of solid potassium carbonate. The product was extracted with ethyl acetate (2×500 ml), the organics combined and washed with water (50 ml), dried (sodium sulfate) and the solvent removed in vacuo to afford the title compound as an orange solid (16.08 g).

$^1$H NMR (400 MHz, CDCl$_3$) δ=7.39-7.32 (1H, d), 7.26 (1H, s), 7.1-7.13 (1H, t), 7.08-7.03 (1H, d), 6.17 (1H, bs), 3.94 (2H, s), 3.02 (2H, s), 1.37 (6H, s).

CHN for C$_{12}$H$_{15}$BrClNO calc. (found): C 47.32 (47.26), H 4.96 (4.87), N 4.60 (4.65).

LRMS (electrospray) m/z 306 [M+H]$^+$

Preparation 67

1-(3-bromophenyl)-2-methylpropan-2-ol)

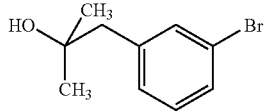

Methylmagnesium bromide (3M solution in diethylether, 51.6 ml, 155 mmol) was slowly added to a solution of 1-(3-bromo-phenyl)propan-2-one (15.0 g, 70 mmol) in dry diethylether (200 ml) at 0° C. The resulting mixture was left for 3 hours, then cooled to 0° C. and slowly quenched with saturated aqueous ammonium chloride solution. The organic phase was washed with brine, dried (sodium sulfate). The yellow oil was then purified by column chromatography on silica gel eluting with dichloromethane:pentane:methanol (90:5:5 by volume to afford a pale yellow oil (13.26 g).

$^1$H NMR (400 MHz, CDCl$_3$) δ=7.40 (2H, m), 7.15 (2H, m), 2.74 (2H, s), 1.42 (1H, bs), 1.22 (6H, s).

Preparation 68

3-((2R)-2-{(2R)-2-[6-(2,5-Dimethylpyrrol-1-yl)pyridin-3-yl]-2-hydroxyethylamino}propyl)benzoic acid

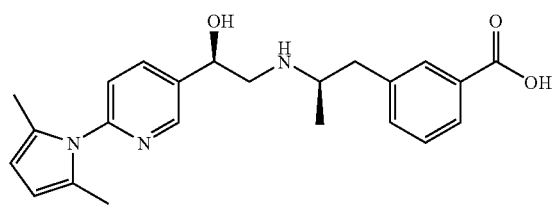

Prepared according to the method described for preparation 21 using preparation 69 to give the title compound as an orange solid.

$^1$H NMR (400 MHz, CD$_3$OD): δ=8.84 (1H, d), 8.08 (1H, dd), 7.87-7.89 (2H, m), 7.37-7.40 (3H, m), 5.82 (2H, s), 5.11 (1H, dd), 3.57-3.63 (1H, m), 3.34-3.39 (2H, m), 3.23-3.28 (1H, m), 2.81 (1H, dd), 2.05 (6H, s), 1.26 (3H, d) ppm.

LRMS (electrospray): m/z [M+H]$^+$ 394, [M−H]$^−$ 392.

Preparation 69

3-((2R)-2-{(2R)-2-[6-(2,5-Dimethylpyrrol-1-yl)pyridin-3-yl]-2-hydroxyethylamino}propyl)benzoic acid methyl ester

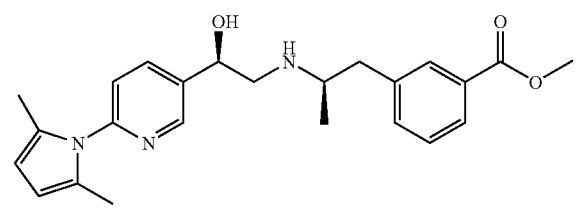

Prepared according to the method described for preparation 22 using the amine from preparation 70 and the epoxide from preparation 27 to give the title compound as a brown oil.

$^1$H NMR (400 MHz, CD$_3$OD): δ=8.53 (1H, d), 7.95 (1H, dd), 7.84-7.87 (2H, m), 7.45-7.48 (1H, m), 7.38-7.42 (1H, m), 7.28 (1H, d), 5.81 (2H, s), 4.83-4.85 (1H, m), 3.88 (3H, s), 2.99 (1H, q), 2.86-2.91 (3H, m), 2.63 (1H, dd), 2.03 (6H, s), 1.07 (3H, d) ppm.

LRMS (APCI): m/z [M+H]$^+$ 408.

Preparation 70 methyl {3-[(2R)-2-aminopropyl]phenyl}acetate

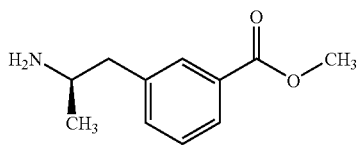

A solution of preparation 71 (13.65 g, 40.9 mmol) and ammonium formate (12.9 g, 204 mmol) in ethanol (200 ml) was heated at reflux in the presence of 20% of palladium hydroxide on charcoal (Pd(OH)$_2$/C, 1.36 g). After 3 hours the reaction mixture was cooled to room temperature, filtered through arbocel and the filtrate concentrated in vacuo. The residue was partitioned between dichloromethane (200 ml) and 880 ammonia (100 ml) and the organic phase separated. The aqueous phase was extracted with further dichloromethane (3×100 ml) and the combined organic extracts washed with brine (100 ml), dried (sodium sulfate) and reduced in vacuo to give the title compound (8.48 g) as a pale yellow oil.

$^1$H NMR (400 MHz, CDCl$_3$): δ=7.90-7.87 (2H, m), 7.38-7.34 (2H, m), 3.90 (3H, s), 3.26-3.17 (1H, m), 2.78-2.73 (1H, dd), 2.64-2.59 (1H, dd), 1.14-1.12 (3H, d) ppm.

LRMS (electrospray): m/z [M+H]$^+$ 194.

Preparation 71 methyl [3-((2R)-2-{[(1R)-1-phenyl-ethyl]-amino}-propyl)-phenyl]-acetate hydrochloride

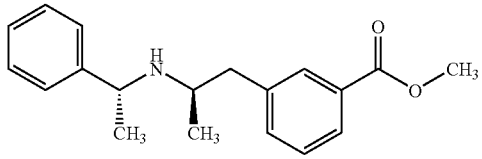

A solution of preparation 72 (45.3 g, 236 mmol), (R)-α-methylbenzylamine (27.6 ml, 214 mmol), sodium triacetoxyborohydride (68.1 g, 321 mmol) and acetic acid (14.7 ml, 257 mmol) in dichloromethane (1500 ml) was stirred at room temperature for 18 hours. The reaction mixture was quenched by addition of saturated aqueous sodium bicarbonate (600 ml) and allowed to stir until effervescence ceased. The organic phase was separated and the aqueous phase extracted with further dichloromethane (2×100 ml). The combined organic extracts were washed with brine (100 ml), dried (sodium sulfate), filtered through Celite and reduced in vacuo. The oil was dissolved in methanol (200 ml), treated with 1M hydrogen chloride in methanol (300 ml) and reduced in vacuo to give a 4:1 mixture of diastereomers (R,R major) as an off-white, hydrochloride salt. Two successive crystallisations (diisopropylether/methanol) gave the title compound (27.3 g) as a colourless crystalline solid.

$^1$H NMR (400 MHz, CD$_3$OD): δ=7.92-7.90 (1H, d), 7.75 (1H, s), 7.55-7.49 (5H, m), 7.45-7.42 (1H, dd), 7.35-7.33 (1H, d), 4.68-4.63 (1H, q), 3.90 (3H, s), 3.43-3.38 (1H, dd), 3.25-3.19 (1H, m), 2.71-2.65 (1H, dd), 1.71-1.69 (3H, d), 1.17-1.16, (3H, d) ppm.

Preparation 72 methyl [3-(2-oxopropyl)phenyl]acetate

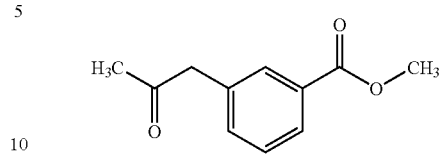

Tributyltin methoxide (80.3 ml, 279 mmol), methyl 3-bromobenzoate (53.5 g, 249 mmol), isopropenyl acetate (39.4 ml, 358 mmol), palladium(II)acetate (2.6 g, 11.6 mmol) and tri-o-tolylphosphine (7.1 g, 23.2 mmol) were stirred together in toluene (350 ml) at 100° C. under nitrogen for 18 hours. After cooling, the reaction was treated with 4M aqueous potassium fluoride solution (560 ml) and stirred for 2 hours. The resulting mixture was diluted with further toluene (200 ml) and filtered through Celite, washing the filter pad with ethyl acetate. The organic phase was separated, dried (sodium sulfate) and reduced in vacuo. The residue was purified by flash column chromatography on silica gel eluting with ethylacetate:pentane (10:90, changing to 20:80, by volume) to give the title compound (45.3 g) as an orange oil.

$^1$H NMR (400 MHz, CDCl$_3$): δ=7.95-7.93 (1H, d), 7.87 (1H, s), 7.43-7.37 (2H, m), 3.91 (3H, s), 3.75 (2H, s), 2.18 (3H, s) ppm.

LRMS (electrospray): m/z [M+Na]$^+$ 215, [M−H]$^−$ 191.

Preparation 73

3'-(Aminomethyl)biphenyl-4-ol

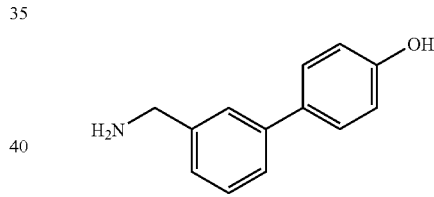

The phenol from preparation 74 (0.73 g, 2.43 mmol) was treated with 4M HCl in dioxan (6 ml, 24.3 mmol) and the resulting solution allowed to stir at room temperature for 3 hours. The solvent was removed in vacuo to give the title compound as a colourless solid.

$^1$HNMR (400 MHz, CD$_3$OD) δ: 7.65 (s, 1H), 7.61 (d, 1H), 7.45-7.50 (m, 3H), 7.34 (d, 1H), 6.87 (d, 2H), 4.17 (s, 2H) ppm.

MS (electrospray) m/z 198 [M−H]$^−$, 200 [M+H]$^+$

Preparation 74 tert-Butyl [(4'-hydroxybiphenyl-3-yl)methyl]carbamate

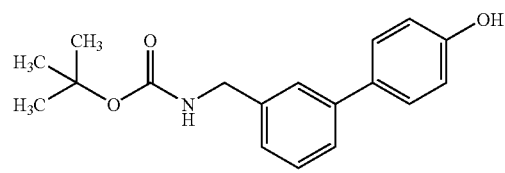

A solution of the iodide from preparation 75 (0.75 g, 2.25 mmol), 4-hydroxy phenylboronic acid (0.62 g, 4.50 mmol), 1,1'-bis(diphenylphosphino)ferrocenyl palladium(II)chloride (0.11 g, 0.14 mmol), in N,N-dimethylformamide (14 ml) was treated with 2M aq. sodium carbonate (4 ml) and the resulting mixture heated at 80° C. under a nitrogen atmosphere for 16 hours. The solvent was removed under reduced pressure and the residue purified by column chromatography on silica gel eluting with ethyl acetate:pentane (1:3) to give the title compound as a pale pink crystalline solid (0.73 g).
$^1$HNMR (400 MHz, CDCl$_3$) δ: 7.43-7.45 (m, 4H), 7.37 (dd, 1H), 7.21 (d, 1H), 6.89 (d, 2H), 4.87-4.94 (bs, 1H), 4.33-4.41 (m, 2H), 1.47 (s, 9H) ppm.
MS (electrospray) m/z 298 [M−H]$^-$, 322 [M+Na]$^+$ Preparation 75 tert-Butyl (3-iodobenzyl)carbamate

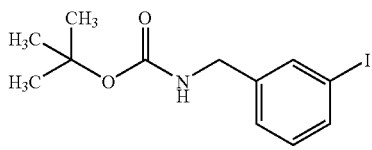

A suspension of 3-iodobenzylamine hydrochloride (4.95 g, 18.4 mmol) in dichloromethane (100 ml) was treated with triethylamine (3.1 ml, 22 mmol) and di-t-butyl dicarbonate (4.40 g, 20 mmol) and the resulting solution left to stir at room temperature under a nitrogen atmosphere for 1.5 hours. The reaction mixture was washed with 2M hydrochloric acid (30 ml), water (30 ml), dried (sodium sulfate), and the solvent removed in vacuo to give the title compound as a colourless solid (6.43 g).
$^1$HNMR (400 MHz, CDCl$_3$) δ: 7.63 (s, 1H), 7.60 (d, 1H), 7.25 (d, 1H), 7.06 (dd, 1H), 4.79-4.89 (bs, 1H), 4.21-4.30 (m, 2H), 1.46 (s, 9H) ppm.
MS (electrospray) m/z 332 [M−H]$^-$, 356 [M+Na]$^+$ Preparation 76

[2-(4-{[tert-Butyl(dimethyl)silyl]oxy}phenyl)-2-methylpropyl]amine

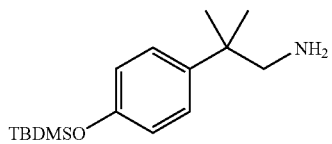

A solution of the nitrile from preparation 77 (0.75 g, 2.7 mmol) in diethyl ether (5 ml) was added dropwise to a cold (0° C.) solution of lithium aluminium hydride in diethyl ether (2.98 ml of a 1M solution). The resulting solution was stirred at 0° C. for 3 hours and then quenched by addition of water (0.1 ml), 2N aqueous sodium chloride (0.1 ml), and further water (0.3 ml). The resulting suspension was filtered and the filtrate concentrated in vacuo. Purification by column chromatography on silica gel eluting with dichloromethane:methanol:0.880 ammonia (97:3:0.5 changing to 93:7:0.5) gave the title compound as a colourless oil (0.52 g).

$^1$HNMR (400 MHz, CDCl$_3$) δ: 7.16 (d, 2H), 6.78 (d, 2H), 2.73 (s, 2H), 1.25 (s, 6H), 1.00 (bs, 2H), 0.97 (s, 9H), 0.18 (s, 6H) ppm.
MS (APCl) m/z 280 [M+H]$^+$ Preparation 77

2-(4-{[tert-Butyl(dimethyl)silyl]oxy}phenyl)-2-methyl propanenitrile

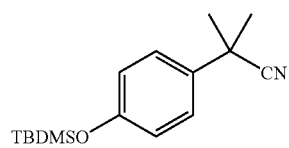

A solution of the nitrile from preparation 78 (5.62 g, 22.7 mmol), methyl iodide (3.11 ml, 50 mmol), and 18-crown-6 (1.5 g, 5.6 mmol) in dry tetrahydrofuran (300 ml) was cooled to −78° C. under a nitrogen atmosphere. Potassium tert-butoxide (50 ml of a 1M solution in tetrahydrofuran, 50 mmol) was added dropwise over 20 minutes and the reaction mixture then allowed to warm gradually to room temperature. After 2 hours the reaction was re-cooled to −78° C. and quenched by addition of sat. aq. ammonium chloride (200 ml) and allowed to warm to room temperature. The resulting solution was extracted with ethyl acetate (300 ml×2), the combined organics were dried (sodium sulfate) and the solvent removed in vacuo. Purification by column chromatography on silica gel eluting with ethyl acetate:pentane (0:100 changing to 10:90) gave the title compound as a colourless oil (4.75 g).
$^1$HNMR (400 MHz, CDCl$_3$) δ: 7.30 (d, 2H), 6.82 (d, 2H), 1.68 (s, 6H), 0.97 (s, 9H), 0.19 (s, 6H) ppm.
MS (APCl) m/z 293 [M+NH$_4$]$^+$ Preparation 78

(4-{[tert-Butyl(dimethyl)silyl]oxy}phenyl)acetonitrile

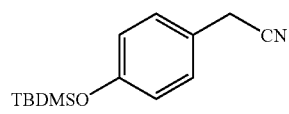

A solution of (4-hydroxyphenyl)acetonitrile (6.01 g, 45.1 mmol) in N,N-dimethylformamide (60 ml) was treated with imidazole (3.81 g, 58.6 mmol), tert-butyldimethylsilylchloride (7.49 g, 49.6 mmol) and N,N-dimethylaminopyridine (20 mg) and the resulting solution left to stir at room temperature under a nitrogen atmosphere for 16 hours. The reaction mixture was diluted with water (200 ml) and extracted with ethyl acetate (200 ml×2). The combined organic extracts were washed with sat. aq. sodium chloride (200 ml), dried (sodium sulfate) and the solvent removed in vacuo. Purification by column chromatography on silica gel eluting with ethyl acetate:pentane (0:100 changing to 10:90) gave the title compound as a pale yellow oil (9.44 g).
$^1$HNMR (400 MHz, CDCl$_3$) δ: 7.17 (d, 2H), 6.82 (d, 2H), 3.66 (s, 2H), 0.97 (s, 9H), 0.19 (s, 6H) ppm.
MS (APCl) m/z 265 [M+NH$_4$]$^+$ Preparation 79

[(4-{[tert-Butyl(dimethyl)silyl]oxy}-1-naphthyl)methyl]amine

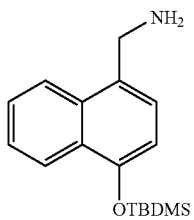

Preparation 80 (250 mg, 0.76 mol) and dimethylbarbituric acid (581 mg, 3.72 mmol) were heated to reflux in dichloromethane (30 ml) for 15 min. Tetrakis(triphenylphosphine)palladium(0) (88 mg, 76 □mol) was added and the resulting mixture heated to reflux for 20 h. The solvent was removed and the material dissolved in ethyl acetate (30 ml), washed with sodium hydroxide (1M, 3×30 ml). The aqueous was extracted with ethyl acetate (30 ml). The combined organics were passed through a strong cation exchange resin column (methanol to 1M ammonia in methanol) to afford a brown oil (162 mg).

$^1$HNMR (400 MHz, CDCl$_3$) δ: 8.25 (d, 1H), 8.00 (d, 1H), 7.46-7.55 (m, 4H), 7.27 (t, 1H), 6.80 (d, 1H), 4.24 (s, 2H), 2.31 (bs, 2H), 1.09 (s, 9H), 0.28 (s, 6H).

Preparation 80

N-[(4-{[tert-butyl(dimethyl)silyl]oxy}-1-naphthyl)methyl]prop-2-en-1-amine

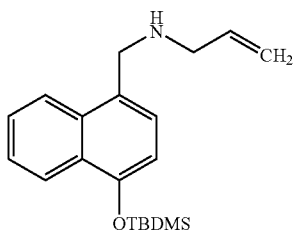

Preparation 81 (1.00 g, 3.5 mmol), allylamine (219 mg, 3.85 mmol) and acetic acid (2 drops) were dissolved in dichloromethane (10 ml) and stirred for 15 min. Sodium triacetoxyborohydride (1.11 g, 5.25 mmol) was added and the resulting mixture allowed to stir for 4 days. Sodium hydrogen carbonate (10 ml) was added and the mixture stirred for a further 90 min. The mixture was separated and the aqueous phase re-extracted with dichloromethane (10 ml), and the combined organics washed with brine (20 ml) and dried (MgSO$_4$). The material was purified by chromatography (0-10% methanol in dichloromethane +1% ammonia), the material was further purified by chromatography (0-25% ethyl acetate in pentane) to yield a dark yellow oil (250 mg)

$^1$HNMR (400 MHz, CDCl$_3$) δ: 8.25 (d, 1H), 8.07 (d, 1H), 7.47-7.57 (m, 2H), 7.32 (d, 1H), 6.82 (d, 1H), 5.95-6.05 (m, 1H), 5.25 (dd, 1H), 5.16 (dd, 1H), 4.17 (s, 2H), 3.39 (d, 2H), 1.97 (bs, 1H), 1.11 (s, 9H), 0.30 (s, 6H) ppm.

MS (electrospray) m/z 328 [M+H]$^+$, 655 [2M+H]$^+$

Preparation 81

4-{[tert-Butyl(dimethyl)silyl]oxy}-1-naphthaldehyde

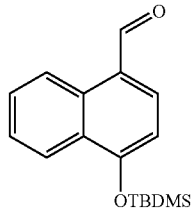

4-Hydroxynaphthalene-1-carbaldehyde (2.00 g, 11.63 mmol), tert-butyldimethylsilyl chloride (1.93 g, 12.80 mmol), imidazole (983 mg, 15.12 mmol) and N,N-dimethylaminopyridine (4 mg) in N,N-dimethylformamide (20 ml) were stirred at RT for 20 h. The solvent was removed and the mixture suspended in ethyl acetate (20 ml) and washed with water (20 ml). The aqueous phase was extracted with ethyl acetate (20 ml) and the combined organics washed with brine (2×20 ml) and dried (MgSO$_4$). The solvent was removed leaving the product as a brown oil which solidified on standing.

$^1$HNMR (400 MHz, CDCl$_3$) δ: 10.21 (s, 1H), 9.30 (dd, 1H), 8.27 (dd, 1H), 7.86 (d, 1H), 7.68 (dd, 1H), 7.56 (dd, 1H), 6.94 (d, 1H), 1.10 (s, 9H), 0.36 (s, 6H).

Preparation 82

4'-(Aminomethyl)biphenyl-4-ol hydrochloride

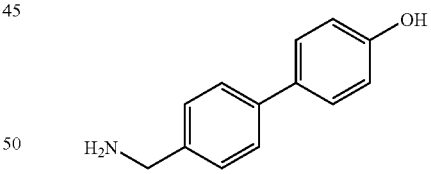

A solution of 4'-hydroxybiphenyl-4-carbonitrile (10.0 g, 51.22 mmol) in tetrahydrofuran (500 ml) was treated with a solution of diborane (1M in tetrahydrofuran, 102 ml, 102 mmol) and the resulting solution heated to reflux under nitrogen for 6 h. After cooling to RT the mixture was treated with hydrochloric acid (6N, 200 ml) and heated to reflux for 30 min. The solvents were removed and dissolved in methanol, then added onto a strong cation exchange column (methanol then 1M ammonia in methanol) to yield a cream solid. The solid was taken up in 1M hydrochloric acid in methanol and after removal of the solvent a yellow solid was obtained (3.8 g)

$^1$HNMR (400 MHz, CD$_3$OD) δ: 7.62 (d, 2H), 7.44-7.46 (m, 4H), 6.83 (d, 2H), 4.15 (s, 2H) ppm.

Preparation 83

(4-Hydroxy-2,5-dimethylphenyl)acetonitrile

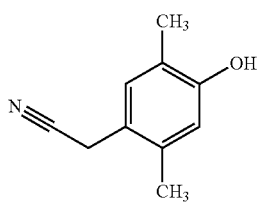

A solution of (4-methoxy-2,5-dimethylphenyl)acetonitrile (0.5 g, 2.9 mmol) in dichloromethane (10 ml) was cooled to −80° C. and treated with a solution of boron tribromide in dichloromethane (14.3 ml of a 1M solution, 14.3 mmol). The reaction mixture was stirred at −80° C. for a further 30 minutes and then gradually allowed to warm to room temperature over a period of 2 hours. The reaction mixture was quenched with saturated aqueous sodium bicarbonate (20 ml) and the organic phase separated. The organic phase was washed with saturated aqueous sodium chloride (20 ml), dried (sodium sulfate) and the solvent removed in vacuo to give a pale brown solid. Purification by column chromatography on silica gel eluting with ethyl acetate:pentane (1:4 changing to 1:2) gave the title compound as a colourless solid (0.28 g).

$^1$HNMR(400 MHz, CD$_3$OD) δ: 2.13 (s, 3H), 2.23 (s, 3H), 3.66 (s, 2H), 6.60 (s, 1H), 6.98 (s, 1H) ppm.

MS (electrospray) m/z 160 [M−H]$^-$

Preparation 84

(4-Hydroxy-2,3-dimethyl phenyl)acetonitrile

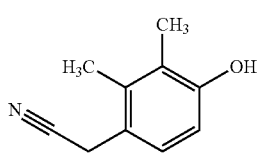

Prepared from (4-methoxy-2,3-dimethylphenyl)acetonitrile using the method from preparation 83 to give the title compound as a pale yellow solid.

$^1$HNMR(400 MHz, CDCl$_3$) δ: 2.20 (s, 3H), 2.24 (s, 3H), 3.62 (s, 2H), 4.91 (bs, 1H), 6.64 (d, 1H), 7.03 (d, 1H) ppm.

MS (electrospray) m/z 160 [M−H]$^-$

Preparation 85

(4-Hydroxy-3-methylphenyl)acetonitrile

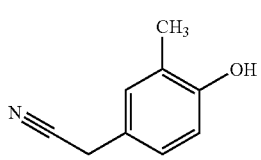

Prepared from (4-methoxy-3-methylphenyl)acetonitrile using the method from preparation 83 to give the title compound as a pale yellow solid.

$^1$HNMR(400 MHz, CDCl$_3$) δ: 2.25 (s, 3H), 3.65 (s, 2H), 4.98 (bs, 1H), 6.76 (d, 1H), 7.01 (d, 1H), 7.07 (s, 1H) ppm.

MS (electrospray) m/z 146 [M−H]$^-$

Preparation 86

4-(2-Aminoethyl)-2,5-dimethylphenol

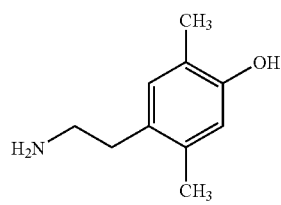

A solution of the nitrile from preparation 83 (0.28 g, 1.74 mmol) in ethanol (15 ml) was hydrogenated at 60 psi over Raney Nickel (0.1 g, 50% w/w) for 16 hours. The reaction mixture was filtered and the solvent removed in vacuo. The residue was purified by strong cation exchange resin eluting non-basic impurities with methanol and then 1M ammonia in methanol to give the title compound as a colourless oil.

$^1$HNMR(400 MHz, CD$_3$OD) δ: 2.11 (s, 3H), 2.19 (s, 3H), 2.63-2.67 (m, 2H), 2.72-2.76 (m, 2H), 6.54 (s, 1H), 6.81 (s, 1H) ppm.

MS (electrospray) m/z 166 [M+H]$^+$

Preparation 87

4-(2-Aminoethyl)-2,3-dimethylphenol

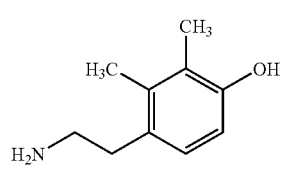

Prepared from the nitrile of preparation 84 using the method of preparation 86 to give the title compound as a colourless oil.

$^1$HNMR(400 MHz, CD$_3$OD) δ: 2.12 (s, 3H), 2.19 (s, 3H), 2.68-2.75 (m, 4H), 6.55 (d, 1H), 6.78 (d, 1H) ppm.

MS (electrospray) m/z 166 [M+H]$^+$

Preparation 88

4-(2-Aminoethyl)-2-methylphenol

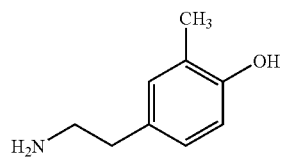

Prepared from the nitrile of preparation 85 using the method of preparation 86 to give the title compound as a colourless oil.

$^1$HNMR(400 MHz, CD$_3$OD) δ: 2.15 (s, 3H), 2.60-2.64 (m, 2H), 2.79-2.83 (m, 2H), 6.66 (d, 1H), 6.82 (d, 1H), 6.90 (s, 1H) ppm.

MS (electrospray) m/z 152 [M+H]$^+$

In vitro Activity of the Compounds of Formula (1)

The ability of the compounds of the formula (1) to act as potent β2 agonists therefore mediating smooth muscle relaxation may be determined by the measure of the effect of beta-2 adrenergic receptor stimulation on electrical field stimulated-contraction of guinea pig trachea strips.

Guinea-pig Trachea

Male, Dunkin-Hartley guinea pigs (475-525 g) are killed by CO$_2$ asphyxiation and exsanguination from the femoral artery and the trachea is isolated. Four preparations are obtained from each animal, starting the dissection immediately below the larynx and taking 2.5 cm length of trachea. The piece of trachea is opened by cutting the cartilage opposite the trachealis muscle, then transverse sections, 3-4 cartilage rings wide, are cut. The resulting strip preparations are suspended in 5 ml organ baths using cotton threads tied through the upper and lower cartilage bands. The strips are equilibrated, un-tensioned, for 20 minutes in a modified Krebs Ringer buffer (Sigma K0507) containing 3 µM Indomethacin (Sigma I7378), 10 µM Guanethidine (Sigma G8520) and 10 µM Atenolol (Sigma A7655), heated at 37° C. and gassed with 95% O$_2$/5% CO$_2$, before applying an initial tension of 1 g. The preparations are allowed to equilibrate for a further 30-45 minutes, during which time they are re-tensioned (to 1 g) twice at 15-minute intervals. Changes in tension are recorded and monitored via standard isometric transducers coupled to a data-collection system (custom-designed at Pfizer). Following the tensioning equilibration, the tissues are subjected to electrical field stimulation (EFS) using the following parameters: 10 s trains every 2 minutes, 0.1 ms pulse width, 10 Hz and just-maximal voltage (25 Volts) continuously throughout the length of the experiment. EFS of post-ganglionic cholinergic nerves in the trachea results in monophasic contractions of the smooth muscle and twitch height is recorded. The organ baths are constantly perfused with the above-described Krebs Ringer buffer by means of a peristaltic pump system (pump flow rate 7.5 ml/minute) throughout the experiment, with the exception of when a beta-2 agonist according to the present invention is added, the pump is then stopped for the time of the cumulative dosing to the bath and started again after maximal response is reached for the wash-out period.

Experimental Protocol for Assessment of Potency and Efficacy

Following equilibration to EFS, the peristaltic pump is stopped and the preparations 'primed' with a single dose of 300 nM isoprenaline (Sigma I5627) to establish a maximal response in terms of inhibition of the contractile EFS response. The isoprenaline is then washed out over a period of 40 minutes. Following the priming and wash-out recovery, a standard curve to isoprenaline is carried out on all tissues (Isoprenaline Curve 1) by means of cumulative, bolus addition to the bath using half log increments in concentration. The concentration range used is $1^{e-9}$ to $1^e/3^{e-6}$ M. At the end of the isoprenaline curve the preparations are washed again for 40 minutes before commencing a second curve, either to isoprenaline (as internal control) or a beta-2 agonist according to the present invention. Beta-2 agonist responses are expressed as percentage inhibition of the EFS response. Data for beta-2 agonist are normalised by expressing inhibition as a percentage of the maximal inhibition induced by isoprenaline in Curve 1. The EC$_{50}$ value for beta-2 agonist according to the present invention refers to the concentration of compound required to produce half maximal effect. Data for beta-2 agonists according to the present invention are then expressed as relative potency to isoprenaline defined by the ratio (EC$_{50}$ beta-2 agonist)/(EC$_{50}$ Isoprenaline).

Confirmation of beta-2 Mediated Functional Activity

Beta-2 agonist activity of test compounds is confirmed using the protocol above, however, prior to constructing the curve to beta-2 agonist according to the present invention, the preparations are pre-incubated (for a minimum of 45 minutes) with 300 nM ICI 118551 (a selective β$_2$ antagonist) which results in the case of a beta-2 mediated effect in a rightward-shift of the test compound dose response curve.

It has thus been found that the compounds of formula (1) according to the present invention that have been tested show a relative potency to Isoprenaline which is comprised between 0.01 and 10.0.

According to another alternative, the agonist potency for the β2 receptor of the compounds of the formula (1) may also be determined by the measure of the concentration of compound according to the present invention required to produce half maximal effect (EC$_{50}$) for the β2 receptor.

Compound Preparation 10 mM/100% DMSO (dimethylsulfoxide) stock of compound is diluted to required top dose in 4% DMSO. This top dose is used to construct a 10-point semi-log dilution curve, all in 4% DMSO. Isoprenaline (Sigma, I-5627) was used as a standard in every experiment and for control wells on each plate. Data was expressed as % Isoprenaline response.

Cell Culture

CHO (Chinese Hamster Ovary) cells recombinantly expressing the human β2 adrenergic receptor (from Kobilka et al., PNAS 84: 46-50, 1987 and Bouvier et al., Mol Pharmacol 33: 133-139 1988 CHOhβ2) were grown in Dulbeccos MEM/NUT MIX F12 (Gibco, 21331-020) supplemented with 10% foetal bovine serum (Sigma, F4135, Lot 90K8404 Exp 09/04), 2 mM glutamine (Sigma, G7513), 500 µg/ml geneticin (Sigma, G7034) and 10 µg/ml puromycin (Sigma, P8833). Cells were seeded to give about 90% confluency for testing.

Assay Method

25 µl/well each dose of compound was transferred into a cAMP-Flashplate® (NEN, SMP004B), with 1% DMSO as basal controls and 100 nM Isoprenaline as max controls. This was diluted 1:2 by the addition of 25 µl/well PBS. Cells were trypsinised (0.25% Sigma, T4049), washed with PBS (Gibco, 14040-174) and resuspended in stimulation buffer (NEN, SMP004B) to give 1×10$^6$ cells/ml CHOhB2. Compounds were incubated with 50 µl/well cells for 1 hour. Cells were then lysed by the addition of 100 µl/well detection buffer (NEN, SMP004B) containing 0.18 µCi/ml $^{125}$I-cAMP (NEN, NEX-130) and plates were incubated at room temperature for a further 2 hours. The amount of $^{125}$I-cAMP bound to the Flashplate® was quantified using a Topcount NXT (Packard), normal counting efficiency for 1 minute. Dose-response data was expressed as % Isoprenaline activity and fitted using a four parameter sigmoid fit.

The compounds according to examples 1 to 27 show a β2 cAMP EC$_{50}$ between 0.01 nM and 4 nM.

The invention claimed is:
1. A compound of the formula:

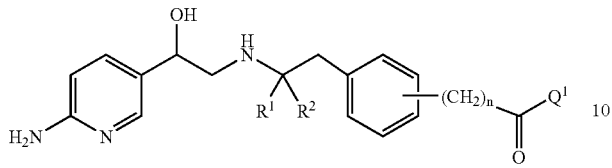
(1)

or a pharmaceutically acceptable salt thereof, wherein the $(CH_2)_n-C(=O)Q^1$ group is substituted on the meta or para position of the benzene ring to which it is attached; $R^1$ and $R^2$ are independently H or $C_1-C_4$ alkyl;
+n is 0, 1 or 2;
$Q^1$ is

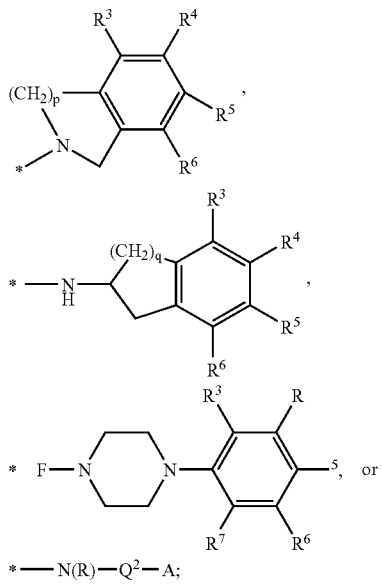

$*-N(R)-Q^2-A$;

p is 1, 2 or 3;
q is 1 or 2;
$Q^2$ is a direct bond or $C_1-C_4$ alkylenyl optionally substituted by OH;
R is H, $C_1-C_4$ alkyl, or phenyl optionally substituted by OH;
A is $C_3-C_7$ cycloalkyl, said cycloalkyl being optionally bridged by one to three carbon atoms; tetrahydropyranyl; piperidinyl; tetrahydrothiopyranyl; pyridyl;

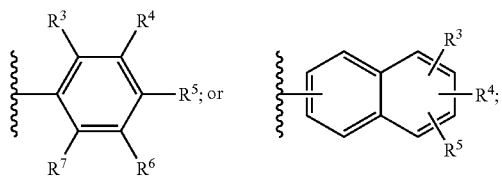

$R^3$, $R^4$, $R^5$, $R^6$ and $R^7$ are the same or different and are each independently H, $C_1-C_4$ alkyl, $OR^9$, $SR^9$, halo, $CF_3$, $OCF_3$, $(CH_2)_mCOOR^9$, $SO_2NR^8R^9$, $CONR^8R^9$, $NR^8R^9$, $NHCOR^8$, $SO_2(C_1-C_4)$alkyl, or phenyl optionally substituted by hydroxy or hydroxy$(C_1-C_4)$alkyl;

m is 0, 1, or 2;
$R^8$ and $R^9$ are the same or different and are each independently H or $C_1-C_4$ alkyl; and
the * represents the attachment point of $Q^1$ to the carbonyl group.

2. A compound of claim 1 wherein n is 1 or 2; $Q^1$ is $*-NH-Q^2-A$; $Q^2$ is $C_1-C_4$ alkylenyl; and A is

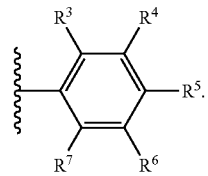

3. A compound of claim 2 wherein $R^3$, $R^4$, $R^5$, $R^6$ and $R^7$ are the same or different and are each independently H, $C_1-C_4$ alkyl, $OR^9$, Cl, F, $CF_3$, $OCF_3$, $COOR^9$, or $SO_2NR^8R^9$, provided at least 2 of $R^3$, $R^4$, $R^5$, $R^6$ and $R^7$ are H; and
$R^8$ and $R^9$ are the same or different and are each independently H or $C_1-C_4$ alkyl.

4. A compound of claim 3 wherein $R^3$, $R^4$, $R^5$, $R^6$ and $R^7$ are the same or different and are each independently H, $CH_3$, OH, $OCH_3$, $OCH_2CH_3$, Cl, F, $CF_3$, $OCF_3$, COOH, or $SO_2NH_2$, provided at least 2 of $R^3$, $R^4$, $R^5$, $R^6$ and $R^7$ are H.

5. A compound of claim 4 wherein $R^3$, $R^4$, $R^5$, $R^6$ and $R^7$ are the same or different and are each independently H, $CH_3$, OH, $OCH_3$, $OCH_2CH_3$, Cl, F, $CF_3$, $OCF_3$, COOH, or $SO_2NH_2$, provided at least 3 of $R^3$, $R^4$, $R^5$, $R^6$ and $R^7$ are H.

6. A compound of claim 1 wherein $Q^1$ is $*-NH-Q^2-A$; $Q^2$ is $C_1-C_4$ alkylene; and A is pyridin-2-yl.

7. A compound of claim 1 wherein $Q^2$ is $-CH_2-$, $-(CH_2)_2-$, $-(CH_2)_3-$ or $-CH(CH_3)-$.

8. A compound of claim 1 wherein $Q^2$ is $-CH_2-$.

9. A compound of claim 1 wherein n is 1 or 2; $Q^1$ is

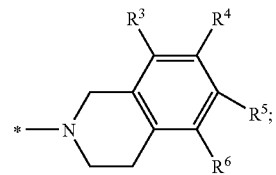

$R^3$, $R^4$, $R^5$ and $R^6$ are the same or different and are each independently H, $C_1-C_4$ alkyl, $OR^9$, $SR^9$, halo, $CF_3$, $OCF_3$, $COOR^9$, $SO_2NR^8R^9$, $CONR^8R^9$, $NR^8R^9$, or $NHCOR^8$, provided at least 2 of $R^3$, $R^4$, $R^5$ and $R^6$ are H; and
$R^8$ and $R^9$ are the same or different and are each independently H or $C_1-C_4$ alkyl.

10. A compound of claim 9 wherein $R^3$, $R^4$, $R^5$ and $R^6$ are the same or different and are each independently H or $OR^9$, provided at least 2 of $R^3$, $R^4$, $R^5$ and $R^6$ are H; and
$R^9$ is H or $C_1-C_4$ alkyl.

11. A compound of claim 1 wherein $Q^1$ is

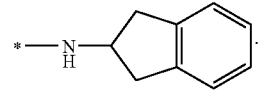

12. A compound of claim 1 wherein n is 1.

13. A compound of claim 1 wherein $R^1$ is H and $R^2$ is $CH_3$; or $R^1$ and $R^2$ are each $CH_3$.

14. A compound of claim 1 wherein n is 0 or 1; $Q^1$ is

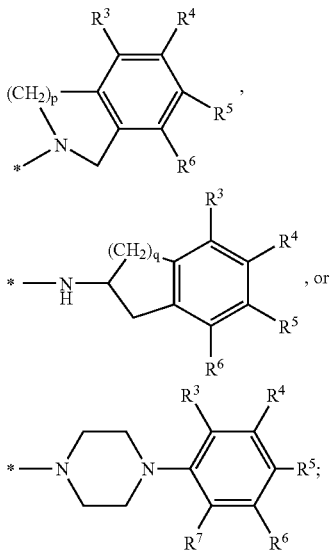

p is 2 or 3; q is 2; and $R^3$, $R^4$, $R^5$ $R^6$ and $R^7$ are the same or different and are each independently H or OH, provided that at least one of $R^3$, $R^4$, $R^5$, $R^6$ and $R^7$ is OH.

15. A compound or claim 1 wherein n is 0 or 1; $R^1$ is H or $C_1$-$C_4$ alkyl; $R^2$ is $C_1$-$C_4$ alkyl; $Q^1$ is *-NR-$Q^2$-A; and A is

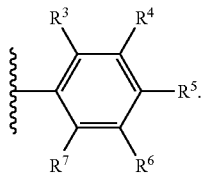

16. A compound of claim 15 wherein $R^1$ is H and $R^2$ is $CH_3$; or $R^1$ and $R^2$ are each $CH_3$.

17. A compound of claim 15 wherein R is H, $CH_3$, $CH_2CH_3$, or phenyl substituted by OH.

18. A compound of claim 15 wherein $Q^2$ is a direct bond or is —$CH_2$—, —$(CH_2)_2$—, —$(CH_2)_4$—, —$CH_2$—$C(CH_3)_2$—, or —$CH_2$—CH(OH)—.

19. A compound of claim 15 wherein A is

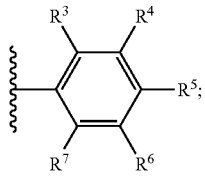

$R^3$, $R^4$, $R^5$, $R^6$ and $R^7$ are the same or different and are each independently H, $C_1$-$C_4$ alkyl, $OR^9$, Cl, F, $CF_3$, $COOR^9$, $SO_2$($C_1$-$C_4$)alkyl, or phenyl substituted by OH or hydroxy($C_1$-$C_4$)alkyl; provided at least 2 of $R^3$, $R^4$, $R^5$, $R^6$ and $R^7$ are H; and $R^8$ and $R^9$ are the same or different and are each independently H or $C_1$-$C_4$ alkyl.

20. A compound of claim 19 wherein $R^3$, $R^4$, $R^5$, $R^6$ and $R^7$ are the same or different and are each independently H, $CH_3$, $C(CH_3)_3$, OH, $OCH_3$, $OCH_2CH_3$, Cl, F, $CF_3$, $COOCH_3$, $SO_2$—$CH_2CH_3$, or phenyl substituted by OH or by —$CH_2$—OH; provided at least 2 of $R^3$, $R^4$, $R^5$, $R^6$ and $R^7$ are H.

21. The (R,R)-stereoisomer of a compound of claim 1.

22. A compound of claim 1 wherein the $(CH^p)_n$—C(=O) $Q^1$ group is substituted on the meta position of the benzene ring to which it is attached.

23. 2-(3-{(2R)-2-[(2R)-2-(6-Amino-pyridin-3-yl)-2-hydroxy-ethylamino]-propyl}-phenyl)-N-benzyl-acetamide;

2-(3-{(2R)-2-[(2R)-2-(6-amino-pyridin-3-yl)-2-hydroxy-ethylamino]-propyl}-phenyl)-N-(2-methoxy-benzyl)-acetamide;

2-(3-{(2R)-2-[(2R)-2-(6-amino-pyridin-3-yl)-2-hydroxy-ethylamino]-propyl}-phenyl)-N-(2-ethoxy-benzyl)-acetamide;

2-(3-{(2R)-2-[(2R)-2-(6-amino-pyridin-3-yl)-2-hydroxy-ethylamino]-propyl}-phenyl)-N-(3-phenyl-propyl)-acetamide;

2-(3-{(2R)-2-[(2R)-2-(6-amino-pyridin-3-yl)-2-hydroxy-ethylamino]-propyl}-phenyl)-N-phenethyl-acetamide;

2-(3-{(2R)-2-[(2R)-2-(6-amino-pyridin-3-yl)-2-hydroxy-ethylamino]-propyl}-phenyl)-N-(3,4-dimethyl-benzyl)-acetamide;

2-(3-{(2R)-2-[(2R)-2-(6-amino-pyridin-3-yl)-2-hydroxy-ethylamino]-propyl}-phenyl)-N-indan-2-yl-acetamide;

2-(3-{(2R)-2-[(2R)-2-(6-amino-pyridin-3-yl)-2-hydroxy-ethylamino]-propyl}-phenyl)-N-(3,4-dichloro-benzyl)-acetamide;

2-(3-{2-[(2R)-2-(6-amino-pyridin-3-yl)-2-hydroxy-ethylamino]-propyl}-phenyl)-N-(4-hydroxy-3-methoxy-benzyl)-acetamide;

2-(4-{2-[(2R)-2-(6-amino-pyridin-3-yl)-2-hydroxy-ethylamino]-2-methyl-propyl}-phenyl)-N-(3-methoxy-benzyl)-acetamide;

2-(4-{2-[(2R)-2-(6-amino-pyridin-3-yl)-2-hydroxy-ethylamino]-2-methyl-propyl}-phenyl)-N-(2,6-dimethoxy-benzyl)-acetamide;

2-(3-{2-[(2R)-2-(6-amino-pyridin-3-yl)-2-hydroxy-ethylamino]-2-methyl-propyl}-phenyl)-N-(4-sulfamoyl-benzyl)-acetamide;

2-(3-{2-[(2R)-2-(6-amino-pyridin-3-yl)-2-hydroxy-ethylamino]-2-methyl-propyl}-phenyl)-N-(2-ethoxy-benzyl)-acetamide;

2-(3-{2-[(2R)-2-(6-amino-pyridin-3-yl)-2-hydroxy-ethylamino]-2-methyl-propyl}-phenyl)-N-indan-2-yl-acetamide;

2-(3-{2-[(2R)-2-(6-amino-pyridin-3-yl)-2-hydroxy-ethylamino]-2-methyl-propyl}-phenyl)-N-benzyl-acetamide;

2-(3-{2-[(2R)-2-(6-amino-pyridin-3-yl)-2-hydroxy-ethylamino]-2-methyl-propyl}-phenyl)-N-phenethyl-acetamide;

2-(3-{2-[(2R)-2-(6-amino-pyridin-3-yl)-2-hydroxy-ethylamino]-2-methyl-propyl}-phenyl)-N-(3-phenyl-propyl)-acetamide;

2-(3-{2-[(2R)-2-(6-amino-pyridin-3-yl)-2-hydroxy-ethylamino]-2-methyl-propyl}-phenyl)-N-(3,5-dichloro-benzyl)-acetamide;

2-(3-{2-[(2R)-2-(6-amino-pyridin-3-yl)-2-hydroxy-ethylamino]-2-methyl-propyl}-phenyl)-N-(3,4-dimethyl-benzyl)-acetamide;

2-(3-{2-[(2R)-2-(6-amino-pyridin-3-yl)-2-hydroxy-ethylamino]-2-methyl-propyl}-phenyl)-N-(3,4-dichloro-benzyl)-acetamide;

2-(3-{2-[(2R)-2-(6-amino-pyridin-3-yl)-2-hydroxy-ethylamino]-propyl}-phenyl)-N-(2-fluoro-5-trifluoromethyl-benzyl)-acetamide;
2-(3-{2-[(2R)-2-(6-amino-pyridin-3-yl)-2-hydroxy-ethylamino]-propyl}-phenyl)-N-(3-trifluoromethoxy-benzyl)-acetamide;
2-(3-{2-[(2R)-2-(6-amino-pyridin-3-yl)-2-hydroxy-ethylamino]-propyl}-phenyl)-N-(3-fluoro-4-trifluoromethyl-benzyl)-acetamide;
2-(3-{2-[(2R)-2-(6-amino-pyridin-3-yl)-2-hydroxy-ethylamino]-propyl}-phenyl)-N-(3,4,5-trimethoxy-benzyl)-acetamide;
-(3-{2-[(2R)-2-(6-amino-pyridin-3-yl)-2-hydroxy-ethylamino]-propyl}-phenyl)-N-(4-trifluoromethoxy-benzyl)-acetamide;
2-(3-{2-[(2R)-2-(6-amino-pyridin-3-yl)-2-hydroxy-ethylamino]-propyl}-phenyl)-N-(4-fluoro-2-trifluoromethyl-benzyl)-acetamide;
2-(3-{2-[(2R)-2-(6-amino-pyridin-3-yl)-2-hydroxy-ethylamino]-propyl}-phenyl)-N-(5-fluoro-2-trifluoromethyl-benzyl)-acetamide;
2-(3-{(2R)-2-[2-(6-aminopyridin-3-yl)-2-hydroxyethylamino]-2-methylpropyl}phenyl)-N-(4'-hydroxybiphenyl-3-ylmethyl)acetamide;
2-(3-{(2R)-2-[2-(6-aminopyridin-3-yl)-2-hydroxyethylamino]-2-methylpropyl}phenyl)-N-(4'-hydroxybiphenyl-4-ylmethyl)acetamide;
2-(3-{(2R)-2-[(2R)-2-(6-aminopyridin-3-yl)-2-hydroxyethylamino]propyl}phenyl)-N-(4'-hydroxy-biphenyl-3-ylmethyl)acetamide;
2-(3-{(2R)-2-[(2R)-2-(6-aminopyridin-3-yl)-2-hydroxyethylamino]propyl}phenyl)-N-(4-hydroxynaphthalen-1-ylmethyl)acetamide;
3-{2-[(2R)-2-(6-aminopyridin-3-yl)-2-hydroxyethylamino]-2-methylpropyl}-N-(4'-hydroxybiphenyl-3-ylmethyl)benzamide;
3-{(2R)-2-[2-(6-amino-pyridin-3-yl)-2-hydroxy-ethylamino]-2-methyl-propyl}-N-[2-(4-hydroxy-phenyl)-2-methyl-propyl]-benzamide;
3-{2-[(2R)-2-(6-amino-pyridin-3-yl)-2-hydroxyethylamino]-2-methylpropyl}-N-[2-(4-hydroxy-2,5-dimethylphenyl)ethyl]benzamide;
3-{2-[(2R)-2-(6-amino-pyridin-3-yl)-2-hydroxyethylamino]-2-methylpropyl}-N-[2-(4-hydroxy-2,3-dimethylphenyl)ethyl]benzamide;
3-{2-[(2R)-2-(6-amino-pyridin-3-yl)-2-hydroxyethylamino]-2-methylpropyl}-N-[2-(4-hydroxy-2-methylphenyl)ethyl]benzamide;
3-{(2R)-2-[(2R)-2-(6-aminopyridin-3-yl)-2-hydroxyethylamino]propyl}-N-[2-(4-hydroxy-2,5-dimethylphenyl)ethyl]benzamide;
3-{(2R)-2-[(2R)-2-(6-aminopyridin-3-yl)-2-hydroxyethylamino]propyl}-N-[2-(4-hydroxy-2,3-dimethylphenyl)ethyl]benzamide;
3-{(2R)-2-[(2R)-2-(6-aminopyridin-3-yl)-2-hydroxyethylamino]propyl}-N-[2-(4-hydroxy-2-methylphenyl)ethyl]benzamide;
2-[3-(2-{[(2R)-2-(6-aminopyridin-3-yl)-2-hydroxyethyl]amino}-2-methyl-propyl)phenyl]-N-(3-hydroxy-4-methoxy-phenyl)acetamide;
2-[3-(2-{[(2R)-2-(6-aminopyridin-3-yl)-2-hydroxyethyl]amino}-2-methyl-propyl)phenyl]-N-(3-hydroxy-phenyl)acetamide;
2-[3-(2-{[(2R)-2-(6-aminopyridin-3-yl)-2-hydroxyethyl]amino}-2-methyl-propyl)phenyl]-N-(2-chloro-4-hydroxy-phenyl)acetamide;
2-[3-(2-{[(2R)-2-(6-aminopyridin-3-yl)-2-hydroxyethyl]amino}-2-methyl-propyl)phenyl]-N-(4-hydroxy-3-methoxy-benzyl)acetamide;
2-[3-(2-{[(2R)-2-(6-aminopyridin-3-yl)-2-hydroxyethyl]amino}-2-methyl-propyl)phenyl]-N-[5-(ethylsulfonyl)-2-hydroxyphenyl]acetamide;
2-[3-(2-{[(2R)-2-(6-aminopyridin-3-yl)-2-hydroxyethyl]amino}-2-methyl-propyl)phenyl]-N-(2-hydroxy-5-methyl-phenyl)acetamide;
2-[3-(2-{[(2R)-2-(6-aminopyridin-3-yl)-2-hydroxyethyl]amino}-2-methyl-propyl)phenyl]-N-(5-chloro-2-hydroxy-benzyl)acetamide;
2-[3-(2-{[(2R)-2-(6-aminopyridin-3-yl)-2-hydroxyethyl]amino}-2-methyl-propyl)phenyl]-N-(4-hydroxy-1,1'-biph-enyl-3-yl)acetamide;
2-[3-(2-{[(2R)-2-(6-aminopyridin-3-yl)-2-hydroxyethyl]amino}-2-methyl-propyl)phenyl]-N-[2-hydroxy-2-(3-hydroxyphenyl)ethyl]-N-methyl-acetamide;
2-[3-(2-{[(2R)-2-(6-aminopyridin-3-yl)-2-hydroxyethyl]amino}-2-methyl-propyl)phenyl]-N-ethyl-N-(3-hydroxy-phenyl)acetamide;
2-[3-(2-{[(2R)-2-(6-aminopyridin-3-yl)-2-hydroxyethyl]amino}-2-methyl-propyl)phenyl]-N-[2-(3-ethoxy-4-hydroxyphenyl)ethyl]acetamide;
2-[3-(2-{[(2R)-2-(6-aminopyridin-3-yl)-2-hydroxyethyl]=amino}-2-methyl-propyl)phenyl]-N-{[4'-(hydroxymeth-yl)-1,1'-biphenyl-3-yl]methyl}acetamide;
2-[3-(2-{[(2R)-2-(6-aminopyridin-3-yl)-2-hydroxyethyl]amino}-2-methyl-propyl)phenyl]-N-(2,4-dichloro-6-hydroxybenzyl)acetamide;
2-[3-(2-{[(2R)-2-(6-aminopyridin-3-yl)-2-hydroxyethyl]amino}-2-methyl-propyl)phenyl]-N-[(3-fluoro-4'-hydroxy-1,1'-biphenyl-4-yl)meth-yl]acetamide;
2-[3-(2-{[(2R)-2-(6-aminopyridin-3-yl)-2-hydroxyethyl]amino}-2-methyl-propyl)phenyl]-N-[(4'-hydroxy-3-methyl-1,1'-biphenyl-4-yl)methyl]acetamide;
2-[3-(2-{[(2R)-2-(6-aminopyridin-3-yl)-2-hydroxyethyl]amino}-2-methyl-propyl)phenyl]-N-(2-chloro-5-hydroxy-benzyl)-N-ethylacetamide;
2-[3-(2-{[(2R)-2-(6-aminopyridin-3-yl)-2-hydroxyethyl]amino}-2-methyl-propyl)phenyl]-N-[(2'-hydroxy-1,1'-biphenyl-2-yl)methyl]acetamide;
2-[3-(2-{[(2R)-2-(6-aminopyridin-3-yl)-2-hydroxyethyl]amino}-2-methyl-propyl)phenyl]-N-[3-hydroxy-5-(trifluoro-methyl)benzyl]-N-methylacetamide;
2-[3-(2-{[(2R)-2-(6-aminopyridin-3-yl)-2-hydroxyethyl]amino}-2-methyl-propyl)phenyl]-N-(3-chloro-5-hydroxy-benzyl)-N-ethylacetamide;
2-[3-(2-{[(2R)-2-(6-aminopyridin-3-yl)-2-hydroxyethyl]amino}-2-methyl-propyl)phenyl]-N-(3-chloro-5-hydroxy-benzyl)acetamide;
2-[3-(2-{[(2R)-2-(6-aminopyridin-3-yl)-2-hydroxyethyl]amino}-2-methyl-propyl)phenyl]-N-(4-hydroxy-3,5-dimethylbenzyl)acetamide;
2-[3-(2-{[(2R)-2-(6-aminopyridin-3-yl)-2-hydroxyethyl]amino}-2-methyl-propyl)phenyl]-N-[2-(2-hydroxyphen-yl)ethyl]acetamide;
2-[3-(2-{[(2R)-2-(6-aminopyridin-3-yl)-2-hydroxyethyl]amino}-2-methyl-propyl)phenyl]-N-benzyl-N-(4-hydroxyphenyl)acetamide;
2-[3-(2-{[(2R)-2-(6-aminopyridin-3-yl)-2-hydroxyethyl]amino}-2-methyl-propyl)phenyl]-N-[2-(4-hydroxyphenyl)-ethyl]acetamide;
2-[3-(2-{[(2R)-2-(6-aminopyridin-3-yl)-2-hydroxyethyl]amino}-2-methyl-propyl)phenyl]-N-(4-hydroxybenzyl)acetamide;

2-[3-(2-{[(2R)-2-(6-aminopyridin-3-yl)-2-hydroxyethyl]-amino}-2-methyl-propyl)phenyl]-N-(2-hydroxybenzyl)acetamide;
2-[3-(2-{[(2R)-2-(6-aminopyridin-3-yl)-2-hydroxyethyl]-amino}-2-methyl-propyl)phenyl]-N-(3-hydroxybenzyl)acetamide;
2-[3-(2-{[(2R)-2-(6-aminopyridin-3-yl)-2-hydroxyethyl]-amino}-2-methyl-propyl)phenyl]-N-[2-(3-hydroxyphenyl)-ethyl]acetamide;
2-[3-(2-{[(2R)-2-(6-aminopyridin-3-yl)-2-hydroxyethyl]-amino}-2-methyl-propyl)phenyl]-N-[2-(4-hydroxy-3-meth-oxyphenyl)ethyl]acetamide;
methyl 4-({[3-(2-{[(2R)-2-(6-aminopyridin-3-yl)-2-hydroxyethyl]-amino}-2-methyl-propyl)phenyl]acetyl}amino)-3-hydroxybenzoate;
2-[3-(2-{[(2R)-2-(6-aminopyridin-3-yl)-2-hydroxyethyl]-amino}-2-methyl-propyl)phenyl]-N-(5-tert-butyl-2-hydroxy-phenyl)acetamide;
2-[3-(2-{[(2R)-2-(6-aminopyridin-3-yl)-2-hydroxyethyl]-amino}-2-methyl-propyl)phenyl]-N-(3-hydroxy-4-methyl-phenyl)acetamide;
2-[3-((2R)-2-{[(2R)-2-(6-aminopyridin-3-yl)-2-hydroxyeth-yl]amino}propyl)phenyl]-N-[2-(4-hydroxyphenyl)ethyl]acetamide;
2-[3-((2R)-2-{[(2R)-2-(6-aminopyridin-3-yl)-2-hydroxyethyl]amino}propyl)phenyl]-N-(4-hydroxybenzyl)acetamide;
2-[3-((2R)-2-{[(2R)-2-(6-aminopyridin-3-yl)-2-hydroxyethyl]amino}propyl)phenyl]-N-(2-hydroxybenzyl)acetamide;
2-[3-((2R)-2-{[(2R)-2-(6-aminopyridin-3-yl)-2-hydroxyethyl]amino}propyl)phenyl]-N-(3-hydroxybenzyl)acetamide;
2-[3-((2R)-2-{[(2R)-2-(6-aminopyridin-3-yl)-2-hydroxyethyl]amino}propyl)phenyl]-N-[2-(3-hydroxyphenyl)ethyl]acetamide;
2-[3-((2R)-2-{[(2R)-2-(6-aminopyridin-3-yl)-2-hydroxyethyl]amino}propyl)phenyl]-N-[2-(4-hydroxy-3-methoxyphenyl)ethyl]acetamide;
2-[3-((2R)-2-{[(2R)-2-(6-aminopyridin-3-yl)-2-hydroxyethyl]amino}propyl)phenyl]-N-(5-tert-butyl-2-hydroxy-phenyl)acetamide;
2-[3-((2R)-2-{[(2R)-2-(6-aminopyridin-3-yl)-2-hydroxyethyl]amino}propyl)phenyl]-N-(3-hydroxy-4-methylphenyl)acetamide;
2-[3-((2R)-2-{[(2R)-2-(6-aminopyridin-3-yl)-2-hydroxyethyl]amino}propyl)phenyl]-N-(3-hydroxy-4-methoxy-phenyl)acetamide;
2-[3-((2R)-2-{[(2R)-2-(6-aminopyridin-3-yl)-2-hydroxyethyl]amino}propyl)phenyl]-N-(4-hydroxy-3-methoxy-benzyl)acetamide;
2-[3-((2R)-2-{[(2R)-2-(6-aminopyridin-3-yl)-2-hydroxyethyl]amino}propyl)phenyl]-N-[5-(ethylsulfonyl)-2-hydroxyphenyl]acetamide;
2-[3-((2R)-2-{[(2R)-2-(6-aminopyridin-3-yl)-2-hydroxyethyl]amino}propyl)phenyl]-N-(2-hydroxy-5-methylphenyl)acetamide;
2-[3-((2R)-2-{[(2R)-2-(6-aminopyridin-3-yl)-2-hydroxyethyl]amino}propyl)phenyl]-N-(3-hydroxy-2-methylphenyl)acetamide;
2-[3-((2R)-2-{[(2R)-2-(6-aminopyridin-3-yl)-2-hydroxyethyl]amino}propyl)phenyl]-N-(5-chloro-2-hydroxybenzyl)-acetamide;
2-[3-((2R)-2-{[(2R)-2-(6-aminopyridin-3-yl)-2-hydroxyethyl]amino}propyl)phenyl]-N-[2-hydroxy-2-(3-hydroxyphenyl)ethyl]-N-methyl-acetamide;
2-[3-((2R)-2-{[(2R)-2-(6-aminopyridin-3-yl)-2-hydroxyethyl]amino}propyl)phenyl]-N-[2-(3-ethoxy-4-hydroxy-phenyl)ethyl]acetamide;
2-[3-((2R)-2-{[(2R)-2-(6-aminopyridin-3-yl)-2-hydroxyethyl]amino}propyl)phenyl]-N-[2-(3-hydroxy-4-methoxy-phenyl)ethyl]acetamide;
2-[3-((2R)-2-{[(2R)-2-(6-aminopyridin-3-yl)-2-hydroxyethyl]amino}propyl)phenyl]-N-ethyl-N-[2-(4-hydroxyphen-yl)ethyl]acetamide;
2-[3-((2R)-2-{[(2R)-2-(6-aminopyridin-3-yl)-2-hydroxyethyl]amino}propyl)phenyl]-N-(2-chloro-4-hydroxybenzyl)-N-ethylacetamide;
2-[3-((2R)-2-{[(2R)-2-(6-aminopyridin-3-yl)-2-hydroxyethyl]amino}propyl)phenyl]-N-(5-hydroxy-1,2,3,4-tetrahydronaphthalen-1-yl)acetamide;
2-[3-((2R)-2-{[(2R)-2-(6-aminopyridin-3-yl)-2-hydroxyethyl]amino}propyl)phenyl]-N-(4-hydroxyphenyl)acetamide;
2-[3-((2R)-2-{[(2R)-2-(6-aminopyridin-3-yl)-2-hydroxyethyl]amino}propyl)phenyl]-N-[4-(4-hydroxyphenyl)butyl]acetamide;
2-[3-((2R)-2-{[(2R)-2-(6-aminopyridin-3-yl)-2-hydroxyethyl]amino}propyl)phenyl]-N-[(4'-hydroxy-1,1'-biphenyl-4-yl)meth-yl]acetamide;
2-[3-((2R)-2-{[(2R)-2-(6-aminopyridin-3-yl)-2-hydroxyethyl]amino}propyl)phenyl]-N-{[4'-(hydroxymethyl)-1,1'-biphenyl-3-yl]methyl}acetamide;
2-[3-((2R)-2-{[(2R)-2-(6-aminopyridin-3-yl)-2-hydroxyethyl]amino}propyl)phenyl]-N-(2,4-dichloro-6-hydroxy-benzyl)acetamide;
2-[3-((2R)-2-{[(2R)-2-(6-aminopyridin-3-yl)-2-hydroxyethyl]amino}propyl)phenyl]-N-[(3-fluoro-4'-hydroxy-1,1'-biphenyl-4-yl)methyl]acetamide;
2-[3-((2R)-2-{[(2R)-2-(6-aminopyridin-3-yl)-2-hydroxyethyl]amino}propyl)phenyl]-N-[(4'-hydroxy-3-methyl-1,1'-biphenyl-4-yl)methyl]acetamide;
2-[3-((2R)-2-{[(2R)-2-(6-aminopyridin-3-yl)-2-hydroxyethyl]amino}propyl)phenyl]-N-(2-chloro-5-hydroxybenzyl)-N-ethylacetamide;
2-[3-((2R)-2-{[(2R)-2-(6-aminopyridin-3-yl)-2-hydroxyethyl]amino}propyl)phenyl]-N-[(2'-hydroxy-1,1'-biphenyl-2-yl)methyl]acetamide;
2-[3-((2R)-2-{[(2R)-2-(6-aminopyridin-3-yl)-2-hydroxyethyl]amino}propyl)phenyl]-N-[3-hydroxy-5-(trifluoro-methyl)benzyl]-N-methylacetamide;
2-[3-((2R)-2-{[(2R)-2-(6-aminopyridin-3-yl)-2-hydroxyethyl]amino}propyl)phenyl]-N-(3-chloro-5-hydroxybenzyl)-N-ethylacetamide;
2-[3-((2R)-2-{[(2R)-2-(6-aminopyridin-3-yl)-2-hydroxyethyl]amino}propyl)phenyl]-N-(3-chloro-5-hydroxybenzyl)acetamide;
2-[3-((2R)-2-{[(2R)-2-(6-aminopyridin-3-yl)-2-hydroxyethyl]amino}propyl)phenyl]-N-(4-hydroxy-3,5-dimeth-ylbenzyl)acetamide;
2-[3-((2R)-2-{[(2R)-2-(6-aminopyridin-3-yl)-2-hydroxyethyl]amino}propyl)phenyl]-N-(3,5-dichloro-2-hydroxy-benzyl)acetamide;
3-(2-{[(2R)-2-(6-aminopyridin-3-yl)-2-hydroxyethyl]-amino}-2-methyl-propyl)-N-[2-(4-hydroxyphenyl)ethyl]benzamide;
3-(2-{[(2R)-2-(6-aminopyridin-3-yl)-2-hydroxyethyl]-amino}-2-methyl-propyl)-N-(4-hydroxybenzyl)benzamide;
3-(2-{[(2R)-2-(6-aminopyridin-3-yl)-2-hydroxyethyl]-amino}-2-methyl-propyl)-N-(2-hydroxybenzyl)benzamide;

3-(2-{[(2R)-2-(6-aminopyridin-3-yl)-2-hydroxyethyl]-amino}-2-methyl-propyl)-N-[2-(3-hydroxyphenyl)ethyl]benzamide;

3-(2-{[(2R)-2-(6-aminopyridin-3-yl)-2-hydroxyethyl]-amino}-2-methyl-propyl)-N-[2-(4-hydroxy-3-methoxyphenyl)ethyl]benzamide;

3-(2-{[(2R)-2-(6-aminopyridin-3-yl)-2-hydroxyethyl]-amino}-2-methyl-propyl)-N-(3-hydroxy-4-methylphenyl)benzamide;

3-(2-{[(2R)-2-(6-aminopyridin-3-yl)-2-hydroxyethyl]-amino}-2-methyl-propyl)-N-[2-(4-hydroxy-3,5-dimethoxyphenyl)ethyl]benzamide;

3-(2-{[(2R)-2-(6-aminopyridin-3-yl)-2-hydroxyethyl]-amino}-2-methyl-propyl)-N-(3-hydroxy4-methoxyphenyl)benzamide;

3-(2-{[(2R)-2-(6-aminopyridin-3-yl)-2-hydroxyethyl]-amino}-2-methyl-propyl)-N-(3-hydroxyphenyl)benzamide;

3-(2-{[(2R)-2-(6-aminopyridin-3-yl)-2-hydroxyethyl]-amino}-2-methyl-propyl)-N-(4-hydroxy-3-methoxybenzyl)benzamide;

3-(2-{[(2R)-2-(6-aminopyridin-3-yl)-2-hydroxyethyl]-amino}-2-methyl-propyl)-N-[5-(ethylsulfonyl)-2-hydroxyphenyl]benzamide;

3-(2-{[(2R)-2-(6-aminopyridin-3-yl)-2-hydroxyethyl]-amino}-2-methyl-propyl)-N-(3-hydroxy-2-methylphenyl)benzamide;

3-(2-{[(2R)-2-(6-aminopyridin-3-yl)-2-hydroxyethyl]-amino}-2-methyl-propyl)-N-(5-chloro-2-hydroxy-benzyl)benzamide;

3-(2-{[(2R)-2-(6-aminopyridin-3-yl)-2-hydroxyethyl]-amino}-2-methyl-propyl)-N-(4-hydroxy-1,1'-biphenyl-3-yl)benzamide;

3-(2-{[(2R)-2-(6-aminopyridin-3-yl)-2-hydroxyethyl]-amino}-2-methyl-propyl)-N-[2-hydroxy-2-(3-hydroxyphenyl)ethyl]-N-methylbenz-amide;

3-(2-{[(2R)-2-(6-aminopyridin-3-yl)-2-hydroxyethyl]-amino}-2-methyl-propyl)-N-(2-hydroxybenzyl)-N-methylbenzamide;

3-(2-{[(2R)-2-(6-aminopyridin-3-yl)-2-hydroxyethyl]-amino}-2-methyl-propyl)-N-(3,5-dichloro-2-hydroxybenzyl)benzamide;

3-(2-{[(2R)-2-(6-aminopyridin-3-yl)-2-hydroxyethyl]-amino}-2-methyl-propyl)-N-[2-(2-hydroxyphenyl)ethyl]benzamide;

3-(2-{[(2R)-2-(6-aminopyridin-3-yl)-2-hydroxyethyl]-amino}-2-methyl-propyl)-N-[2-(3-ethoxy-4-hydroxyphenyl)ethyl]benzamide;

3-(2-{[(2R)-2-(6-aminopyridin-3-yl)-2-hydroxyethyl]-amino}-2-methyl-propyl)-N-[2-(3-hydroxy-4-methoxyphenyl)ethyl]benzamide;

2-[3-(2-{[(2R)-2-(6-aminopyridin-3-yl)-2-hydroxyethyl]-amino}-2-methyl-propyl-benzoyl]-2,3,4,5-tetrahydro-1H-2-benzazepin-8-ol;

3-(2-{[(2R)-2-(6-aminopyridin-3-yl)-2-hydroxyethyl]-amino}-2-methyl-propyl)-N-[(4'-hydroxy-3-methyl-1,1'-biphenyl-4-yl)methyl]-benzamide;

3-(2-{[(2R)-2-(6-aminopyridin-3-yl)-2-hydroxyethyl]-amino}-2-methyl-propyl)-N-[(3'hydroxy-1,1'-biphenyl-2-yl)-methyl]benzamide;

3-((2R)-2-{[(2R)-2-(6-aminopyridin-3-yl)-2-hydroxyethyl]-amino}propyl)-N-(5-chloro-2-hydroxy-benzyl)benzamide;

3-((2R)-2-{[(2R)-2-(6-aminopyridin-3-yl)-2-hydroxyethyl]-amino}propyl)-N-[2-hydroxy-2-(3-hydroxyphenyl)ethyl]-N-methylbenzamide;

3-((2R)-2-{[(2R)-2-(6-aminopyridin-3-yl)-2-hydroxyethyl]-amino}propyl)-N-(2-hydroxybenzyl)-N-methyl-benzamide;

3-((2R)-2-{[(2R)-2-(6-aminopyridin-3-yl)-2-hydroxyethyl]-amino}propyl)-N-[2-(3-ethoxy-4-hydroxyphenyl)ethyl]benzamide;

3-((2R)-2-{[(2R)-2-(6-aminopyridin-3-yl)-2-hydroxyethyl]-amino}propyl)-N-[2-(3-hydroxy-4-methoxyphenyl)ethyl]benzamide;

2-[3-((2R)-2-{[(2R)-2-(6-aminopyridin-3-yl)-2-hydroxyethyl]-amino}propyl)benzoyl]-2,3,4,5-tetrahydro-1H-2-benzazepin-8-ol;

3-((2R)-2-{[(2R)-2-(6-aminopyridin-3-yl)-2-hydroxyethyl]-amino}propyl)-N-ethyl-N-[2-(4-hydroxyphenyl)ethyl]benzamide;

3-((2R)-2-{[(2R)-2-(6-aminopyridin-3-yl)-2-hydroxyethyl]-amino}propyl)-N-(2-chloro-4-hydroxy-benzyl)-N-ethylbenzamide;

3-((2R)-2-{[(2R)-2-(6-aminopyridin-3-yl)-2-hydroxyethyl]-amino}propyl)-N-(5-hydroxy-1,2,3,4-tetrahydronaphthalen-1-yl)benzamide;

2-{4-[3-((2R)-2-{[(2R)-2-(6-amino-pyridin-3-yl)-2-hydroxyethyl]amino}propyl)benzoyl]piperazin-1-yl}phenol;

3-((2R)-2-{[(2R)-2-(6-aminopyridin-3-yl)-2-hydroxyethyl]-amino}propyl)-N-(4-hydroxyphenyl)benzamide;

3-((2R)-2-{[(2R)-2-(6-aminopyridin-3-yl)-2-hydroxyethyl]-amino}propyl)-N-[4-(4-hydroxyphen-yl)butyl]benzamide;

3-((2R)-2-{[(2R)-2-(6-aminopyridin-3-yl)-2-hydroxyethyl]-amino}propyl)-N-[(4'-hydroxy-1,1'-biphenyl-4-yl)methyl]benzamide;

3-((2R)-2-{[(2R)-2-(6-aminopyridin-3-yl)-2-hydroxyethyl]-amino}propyl)-N-{[4'-(hydroxymethyl)-1,1'-biphenyl-3-yl]methyl}benzamide;

3-((2R)-2-{[(2R)-2-(6-aminopyridin-3-yl)-2-hydroxyethyl]-amino}propyl)-N-(2,4-dichloro-6-hydroxybenzyl)benzamide;

3-((2R)-2-{[(2R)-2-(6-aminopyridin-3-yl)-2-hydroxyethyl]-amino}propyl)-N-[(3-fluoro-4'-hydroxy-1,1'-biphenyl-4-yl)methyl]benzamide;

3-((2R)-2-{[(2R)-2-(6-aminopyridin-3-yl)-2-hydroxyethyl]-amino}propyl)-N-[(4'-hydroxy-3-methyl-1,1'-biphenyl-4-yl)methyl]benzamide;

3-((2R)-2-{[(2R)-2-(6-aminopyridin-3-yl)-2-hydroxyethyl]-amino}propyl)-N-(2-chloro-5-hydroxy-benzyl)-N-ethylbenzamide;

3-((2R)-2-{[(2R)-2-(6-aminopyridin-3-yl)-2-hydroxyethyl]-amino}propyl)-N-[(2'-hydroxy-1,1'-biphenyl-2-yl)methyl]benzamide;

3-((2R)-2-{[(2R)-2-(6-aminopyridin-3-yl)-2-hydroxyethyl]-amino}propyl)-N-[(4'-hydroxy-1,1'-biphenyl-2-yl)meth-yl]benzamide;

3-((2R)-2-{[(2R)-2-(6-aminopyridin-3-yl)-2-hydroxyethyl]-amino}propyl)-N-[3-hydroxy-5-(trifluoro-methyl)benzyl]-N-methylbenzamide;

3-((2R)-2-{[(2R)-2-(6-aminopyridin-3-yl)-2-hydroxyethyl]-amino}propyl)-N-(3-chloro-5-hydroxy-benzyl)-N-ethylbenzamide;

3-((2R)-2-{[(2R)-2-(6-aminopyridin-3-yl)-2-hydroxyethyl]-amino}propyl)-N-(3-chloro-5-hydroxy-benzyl)benzamide;

3-((2R)-2-{[(2R)-2-(6-aminopyridin-3-yl)-2-hydroxyethyl]-amino}propyl)-N-[(4'-hydroxy-1,1'-biphenyl-3-yl)methyl]benzamide;

3-((2R)-2-{[(2R)-2-(6-aminopyridin-3-yl)-2-hydroxy-ethyl]-amino}propyl)-N-(4-hydroxy-3,5-dimeth-yl-benzyl)benzamide;
3-((2R)-2-{[(2R)-2-(6-aminopyridin-3-yl)-2-hydroxy-ethyl]-amino}propyl)-N-(3,5-dichloro-2-hydroxyben-zyl)benzamide;
3-((2R)-2-{[(2R)-2-(6-aminopyridin-3-yl)-2-hydroxy-ethyl]-amino}propyl)-N-[2-(2-hydroxyphenyl)-ethyl]benzamide;
3-((2R)-2-{[(2R)-2-(6-aminopyridin-3-yl)-2-hydroxy-ethyl]-amino}propyl)-N-(3-hydroxy4-methoxy-phe-nyl)benzamide;
3-((2R)-2-{[(2R)-2-(6-aminopyridin-3-yl)-2-hydroxy-ethyl]-amino}propyl)-N-(3-hydroxyphenyl)benza-mide;
3-((2R)-2-{[(2R)-2-(6-aminopyridin-3-yl)-2-hydroxy-ethyl]-amino}propyl)-N-(4-hydroxy-3-methoxy-ben-zyl)benzamide;
3-((2R)-2-{[(2R)-2-(6-aminopyridin-3-yl)-2-hydroxy-ethyl]-amino}propyl)-N-[5-(ethylsulfonyl)-2-hydrox-yphenyl]benzamide;
3-((2R)-2-{[(2R)-2-(6-aminopyridin-3-yl)-2-hydroxy-ethyl]-amino}propyl)-N-(2-hydroxy-5-methyl-phenyl)benzamide;
3-((2R)-2-{[(2R)-2-(6-aminopyridin-3-yl)-2-hydroxy-ethyl]-amino}propyl)-N-(3-hydroxy-2-methyl-phenyl)benzamide;
3-((2R)-2-{[(2R)-2-(6-aminopyridin-3-yl)-2-hydroxy-ethyl]-amino}propyl)-N-[2-(4-hydroxyphen-yl)ethyl]benzamide;
3-((2R)-2-{[(2R)-2-(6-aminopyridin-3-yl)-2-hydroxy-ethyl]-amino}propyl)-N-(4-hydroxybenzyl)benza-mide;
3-((2R)-2-{[(2R)-2-(6-aminopyridin-3-yl)-2-hydroxy-ethyl]-amino}propyl)-N-(2-hydroxybenzyl)benza-mide;
3-((2R)-2-{[(2R)-2-(6-aminopyridin-3-yl)-2-hydroxy-ethyl]-amino}propyl)-N-(3-hydroxybenzyl)benza-mide; or
3-((2R)-2-{[(2R)-2-(6-aminopyridin-3-yl)-2-hydroxy-ethyl]-amino}propyl)-N-[2-(3-hydroxyphen-yl)ethyl]benzamide.

24. A process for preparing a compound of claim 1 comprising the steps of
(a) coupling an acid of formula (3):

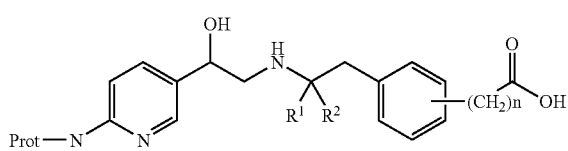

(3)

wherein Prot is a protecting group, with an amine of formula

NRH—Q²—A, (4.1)

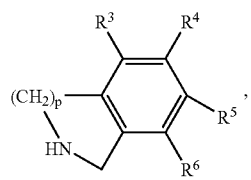

(4.2)

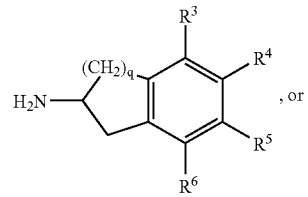

(4.3)

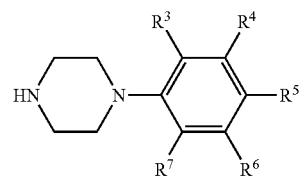

(4.4)

to form a compound of formula (2),

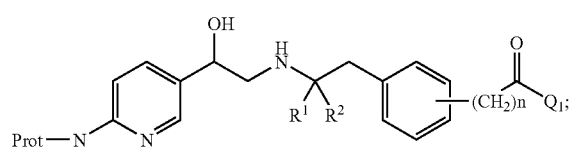

(2)

(b) removing the protecting group "Prot" from the compound of formula (2) to form the compound of claim 1; and
(3) isolating the compound of claim 1.

25. A pharmaceutical composition comprising a compound of claim 1 or a pharmaceutically acceptable salt thereof and a pharmaceutically acceptable excipient or additive.

26. A method of treating asthma, chronic bronchoconstriction, acute bronchoconstriction, bronchitis, small airways obstruction, emphysema, obstructive airways disease, inflammatory airways disease or bronchiectasis in a mammal, which method comprises administering to said mammal in need thereof a therapeutically effective amount of a compound of claim 1 or a pharmaceutically acceptable salt thereof or a pharmaceutical composition comprising a compound of claim 1 or a pharmaceutically acceptable salt thereof and a pharmaceutically acceptable excipient or additive.

27. A method of claim 26 wherein said asthma is atopic asthma, non-atopic asthma, allergic asthma, atopic bronchial IgE-mediated asthma, bronchial asthma, essential asthma, true asthma, intrinsic asthma caused by pathophysiologic disturbances, extrinsic asthma caused by environmental factors, essential asthma of unknown or inapparent cause, non-atopic asthma, bronchitic asthma, emphysematous asthma, exercise-induced asthma, allergen induced asthma, cold air induced asthma, occupational asthma, infective asthma caused by bacterial, fungal, protozoal, or viral infection, non-allergic asthma, incipient asthma, wheezy infant syndrome or bronchiolytis.

28. A method of claim 26 wherein said obstructive airways disease or said inflammatory airways disease is chronic eosinophilic pneumonia, chronic obstructive pulmonary disease (COPD), COPD that includes chronic bronchitis, pulmonary emphysema or dyspnea associated or not associated with COPD, COPD that is characterized by irreversible, progressive airways obstruction, adult respiratory distress syndrome (ARDS), exacerbation of airways hyper-reactivity consequent to other drug therapy or airways disease that is associated with pulmonary hypertension.

29. A method of claim 26 wherein said bronchitis is chronic bronchitis, acute bronchitis, acute laryngotracheal bronchitis, arachidic bronchitis, catarrhal bronchitis, croupus bronchitis, dry bronchitis, infectious asthmatic bronchitis, productive bronchitis, staphylococcus or streptococcal bronchitis or vesicular bronchitis.

30. A method of claim 26 wherein said bronchiectasis is cylindric bronchiectasis, sacculated bronchiectasis, fusiform bronchiectasis, capillary bronchiectasis, cystic bronchiectasis, dry bronchiectasis or follicular bronchiectasis.

31. A method of any one of claims 26-30 wherein said mammal is a human.

32. A pharmaceutical composition comprising a combination of a compound of claim 1 or a pharmaceutically acceptable salt thereof and
  (a) a 5-lipoxygenase (5-LO) inhibitos or a 5-lipoxygenase activating protein (FLAP) antagonist;
  (b) a leukotriene antagonist (LTRA);
  (c) a histamine receptor antagonist;
  (d) an $\alpha_1$- or $\alpha_2$-adrenoceptor agonist vasoconstrictor sympathomimetic agent;
  (e) a muscarinic M3 receptor antagonist or an anticholinergic agents;
  (f) a PDE inhibitors;
  (g) Theophylline;
  (h) Sodium cromoglycate;
  (i) a COX inhibitor;
  (j) an oral or inhaled glucocorticosteroid;
  (k) a monoclonal antibody active against endogenous inflammatory entities;
  (l) an anti-tumor necrosis factor (anti-TNF-$\alpha$) agent;
  (m) an adhesion molecule inhibitor including VLA-4 antagonists,
  (n) a kinin-$B_1$- or kinin-$B_2$-receptor antagonist;
  (o) an immunosuppressive agent;
  (p) an inhibitors of matrix metalloprotease (MMP);
  (q) a tachykinin $NK_1$, $NK_2$ or $NK_3$ receptor antagonist;
  (r) an elastase inhibitor;
  (s) an adenosine A2a receptor agonist;
  (t) an inhibitor of urokinase;
  (u) a compound that acts on a dopamine receptor;
  (v) a modulators of the NF$\kappa\beta$ pathway;
  (w) an agents that can be classed as a mucolytics or anti-tussive; or
  (x) an antibiotic.

33. A pharmaceutical composition of claim 32 wherein said leukotriene antagonist is an antagonist of $LTB_4$, $LTC_4$, $LTD_4$, or $LTE_4$.

34. A pharmaceutical composition of claim 32 wherein said histamine receptor antagonist is an H1 antagonist or an H3 antagonist.

35. A pharmaceutical composition of claim 32 wherein said PDE inhibitor is a PDE3, PDE4 or PDE5 inhibitor.

36. A pharmaceutical composition of claim 32 wherein said COX inhibitor is a non-selective or selective COX-1 inhibitor, or is a non-selective or selective COX-2 inhibitor.

37. A pharmaceutical composition of claim 32 wherein said adhesion molecule inhibitor is a VLA-4 antagonist.

38. A pharmaceutical composition of claim 32 wherein said compound that acts on a dopamine receptor is a D2 agonist.

39. A pharmaceutical composition of claim 32 wherein said modulator of the NF$\kappa\beta$ pathway is an IKK inhibitor.

* * * * *